US 12,412,574 B1

(12) United States Patent
Ryan et al.

(10) Patent No.: US 12,412,574 B1
(45) Date of Patent: Sep. 9, 2025

(54) CONVERSATION-BASED SKILL COMPONENT FOR ASSESSING A USER'S STATE

(71) Applicant: Amazon Technologies, Inc., Seattle, WA (US)

(72) Inventors: Katherine M Ryan, Seattle, WA (US); Avani Parakh, Seattle, WA (US); Chao Wang, Newton, MA (US); Viktor Rozgic, Belmont, MA (US); Siddhartha Reddy Jonnalagadda, Bothell, WA (US); Elizabeth Shriberg, Berkeley, CA (US); Alexandros Potamianos, Santa Monica, CA (US)

(73) Assignee: Amazon Technologies, Inc., Seattle, WA (US)

( * ) Notice: Subject to any disclaimer, the term of this patent is extended or adjusted under 35 U.S.C. 154(b) by 269 days.

(21) Appl. No.: 17/956,137

(22) Filed: Sep. 29, 2022

(51) Int. Cl.
*G10L 15/22* (2006.01)
*G10L 15/06* (2013.01)
*G10L 15/16* (2006.01)

(52) U.S. Cl.
CPC ............ *G10L 15/22* (2013.01); *G10L 15/063* (2013.01); *G10L 15/16* (2013.01); *G10L 2015/0638* (2013.01); *G10L 2015/223* (2013.01)

(58) Field of Classification Search
CPC ....... G10L 15/22; G10L 15/063; G10L 15/16; G10L 2015/0638; G10L 2015/223
See application file for complete search history.

(56) References Cited

U.S. PATENT DOCUMENTS

| | | | |
|---|---|---|---|
| 11,191,466 B1* | 12/2021 | Heneghan | A61B 5/01 |
| 11,633,103 B1* | 4/2023 | Nudd | G06F 17/18 |
| | | | 704/9 |
| 12,050,854 B1* | 7/2024 | Shan | G06F 40/40 |
| 2018/0174020 A1* | 6/2018 | Wu | G06N 3/044 |
| 2021/0345925 A1* | 11/2021 | Davis | A61B 5/7435 |
| 2022/0230632 A1* | 7/2022 | Maitra | A61B 5/7267 |
| 2022/0310079 A1* | 9/2022 | Kalns | G10L 13/02 |
| 2023/0274743 A1* | 8/2023 | Scherer | G06F 3/167 |
| | | | 704/275 |
| 2023/0360772 A1* | 11/2023 | Manteau-Rao | G06F 3/167 |
| 2024/0021196 A1* | 1/2024 | Bolzoni | G06F 16/285 |

OTHER PUBLICATIONS

"Psychology + Technology = One smart Woebot", Woebot Health, https://woebothealth.com/what-powers-woebot/, retrieved from the Internet on Oct. 18, 2022.

* cited by examiner

*Primary Examiner* — Stella L. Woo
(74) *Attorney, Agent, or Firm* — Pierce Atwood LLP

(57) ABSTRACT

The present application provides techniques for implementing a skill component, configured to perform an assessment of a user, as part of a speech processing system. The system may receive a natural language user input requesting assistance. The skill component may, using one or more machine learning models, determine at least one characteristic of the natural language input (e.g., lexical embedding, acoustic embedding, topic, tone, etc.). The skill component may determine state data for a present session, where the state data indicates a topic of the natural language user input and/or a user state associated with the natural language user input. The skill component may determine past state data of one or more past sessions, and generate a question to the user based on the state data for the natural language user input and the past state data.

20 Claims, 16 Drawing Sheets

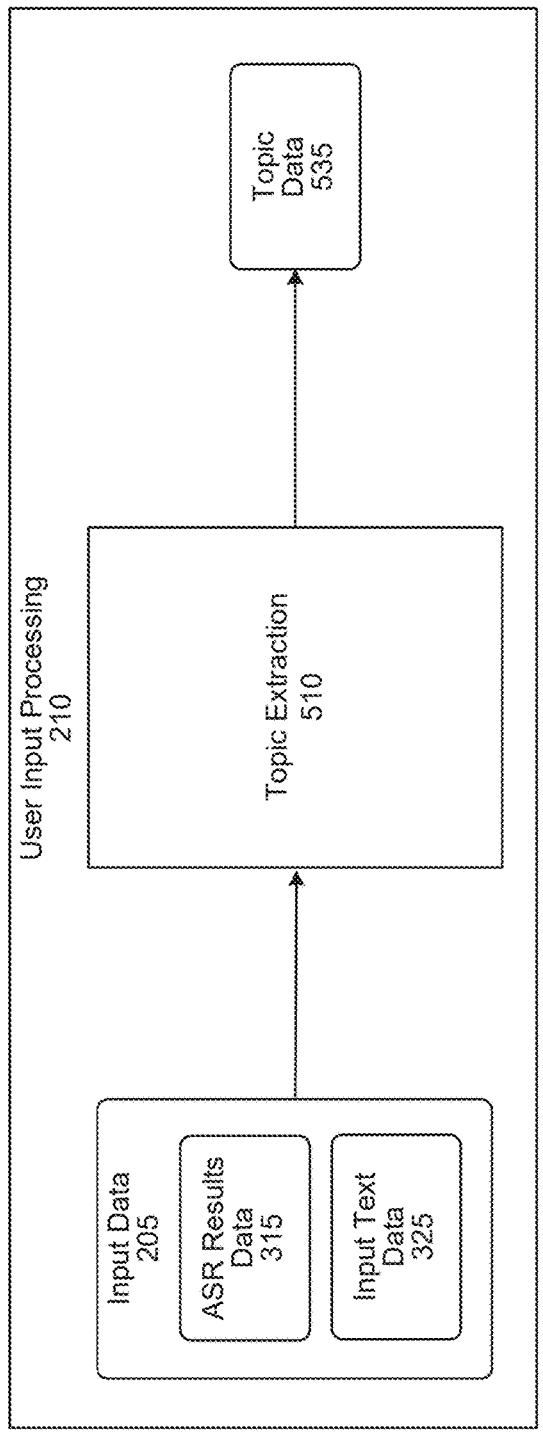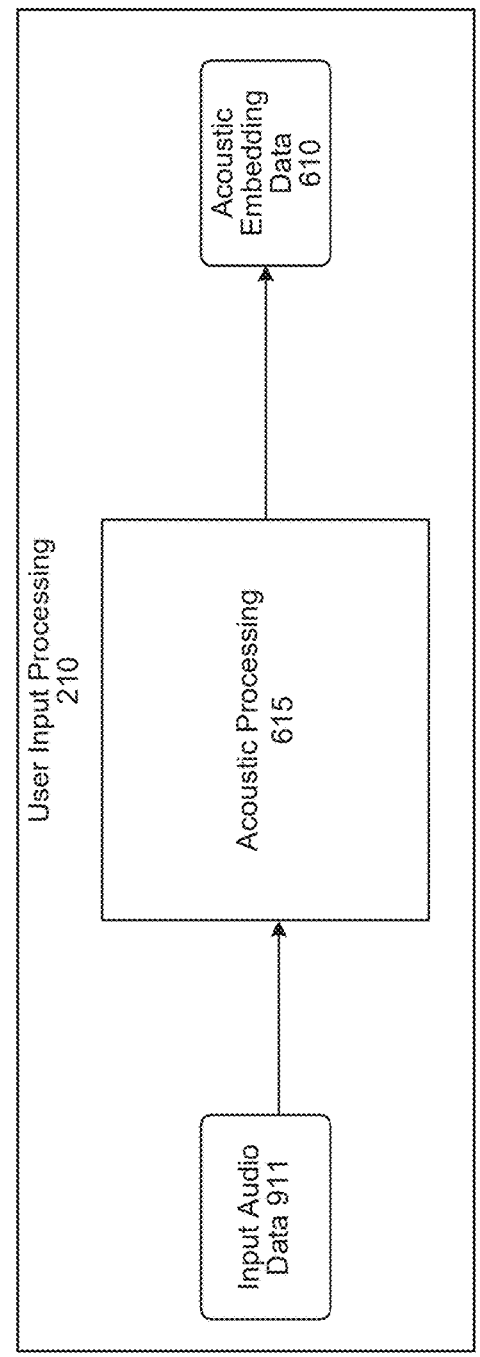

CONVERSATION-BASED SKILL COMPONENT FOR ASSESSING A USER'S STATE

BACKGROUND

Speech recognition systems have progressed to the point where humans can interact with computing devices using their voices. Such systems employ techniques to identify the words spoken by a human user based on the various qualities of a received audio input. Speech recognition combined with natural language understanding processing techniques enable speech-based user control of a computing device to perform tasks based on the user's spoken commands. Speech recognition and natural language understanding processing techniques may be referred to collectively or separately herein as speech processing. Speech processing may also involve converting a user's speech into text data which may then be provided to various text-based software applications.

Speech processing may be used by computers, hand-held devices, telephone computer systems, kiosks, and a wide variety of other devices to improve human-computer interactions.

BRIEF DESCRIPTION OF DRAWINGS

For a more complete understanding of the present disclosure, reference is now made to the following description taken in conjunction with the accompanying drawings.

FIG. 5 is a conceptual diagram illustrating example processing that may be performed by a topic extraction component of the system, according to embodiments of the present disclosure.

FIG. 6 is a conceptual diagram illustrating example processing that may be performed by an acoustic processing component of the system, according to embodiments of the present disclosure.

DETAILED DESCRIPTION

Figure 1:
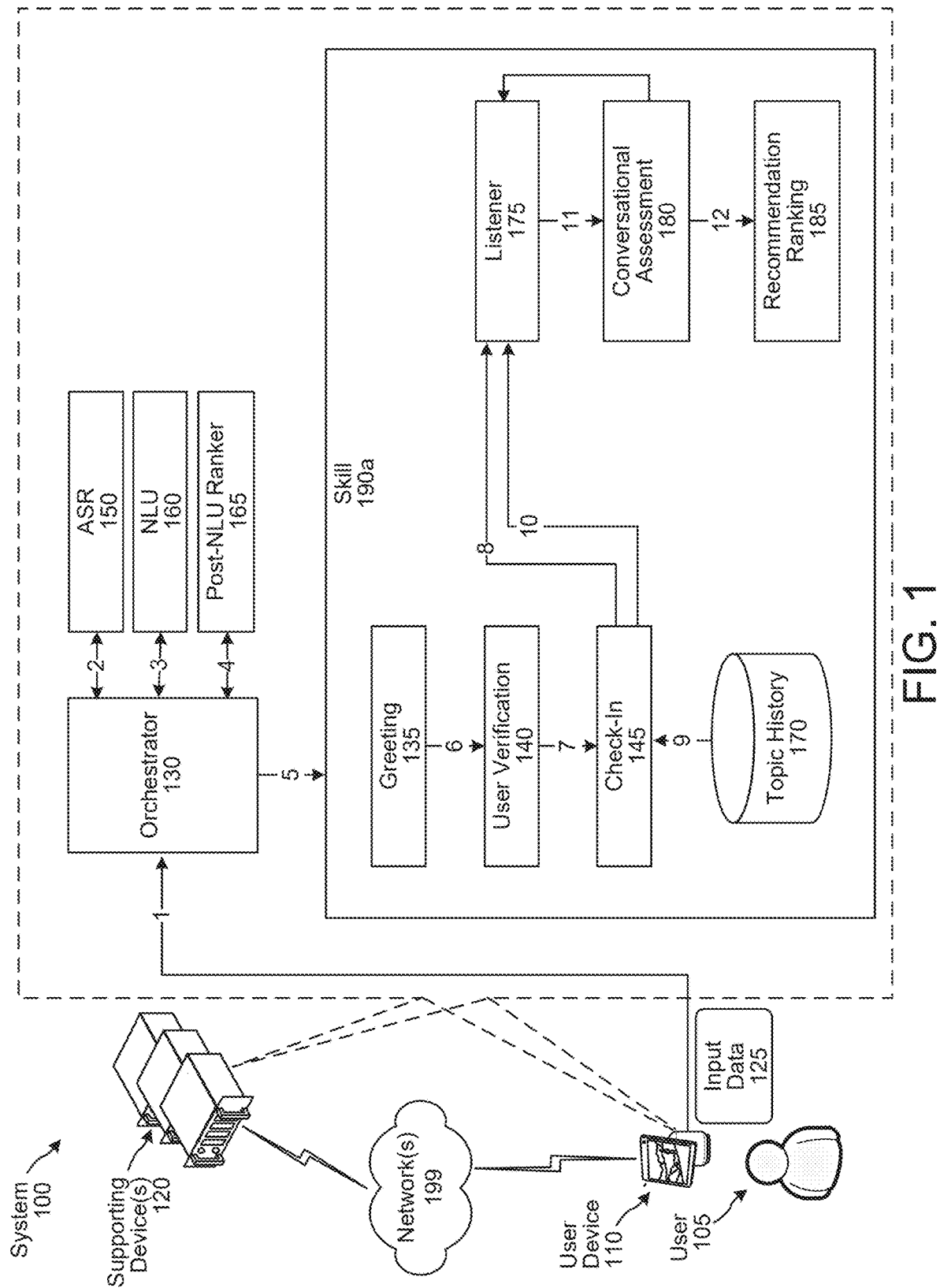
FIG. 1 is a conceptual diagram illustrating a system for processing a user input related to a skill component configured to perform a conversational assessment of a user's state, according to embodiments of the present disclosure.

Automatic speech recognition (ASR) is a field of computer science, artificial intelligence, and linguistics concerned with transforming audio data associated with speech into text representative of that speech. Similarly, natural language understanding (NLU) is a field of computer science, artificial intelligence, and linguistics concerned with enabling computers to derive meaning from text input containing natural language. ASR and NLU are often used together as part of a speech processing system, sometimes referred to as a spoken language understanding (SLU) system. Natural Language Generation (NLG) includes enabling computers to generate output text or other data in words a human can understand, such as sentences or phrases. Text-to-speech (TTS) is a field of computer science concerning transforming textual and/or other data into audio data that is synthesized to resemble human speech. ASR, NLU, NLG, and TTS may be used together as part of a speech-processing/virtual assistant system.

The present disclosure provides techniques for implementing a speech processing system that analyzes information provided through conversational interactions that are natural for humans (e.g., using generated natural language outputs). The system may use data generated based on the interactions to assist the user in understanding the user's status over time, as well as recommend actions for the user to take to improve aspects the user may desire to improve. For example, if data the user provides suggests a state (e.g., mental health state) that could benefit from breathing exercises, online resources, such as websites, or speaking with a health professional, the system can make such recommendations or interactions available to the user.

Skill component of the system may provide various services to a user, such as conversational assessment, appointment scheduling with professionals, reminders regarding provider-prescribed medications, etc. A user may engage with the skill component in multiple ways, such as requesting specific tasks (e.g., scheduling an appointment) or starting an exercise session and/or conversation with the system. A user may use communications functionality, of the skill component, to speak with a professional provider, and allow for the provider to configure the skill component with recommended activities, exercises, resources, or reminders.

A skill component in accordance with embodiments of the present disclosure may be configured to analyze user speech, in response to user authorization, for audio characteristics that are indicative of a particular health state, for example, a tone of the user, an intensity of a tone, etc. The skill component may also be configured to send notifications to the user on a periodic-basis, if such are authorized by the user, where a notification may act as a "check-in" and request the user to provide an input.

In an aspect of the present disclosure, a system may receive, from a user device, a natural language user input. The system may determine that the natural language user input is to be processed using the skill component. The skill component may thereafter generate a question(s) or statement(s) related to a machine assessment, and the user device may present the question(s) or statement(s) to the user.

After the user device presents the question or statement, the system may receive another natural language user input responsive to the question or statement. In the situation where this natural language user input is a spoken natural language user input (e.g., one or more utterances), the system may generate ASR results data corresponding to the spoken natural language user input. The system may also generate a lexical embedding of the natural language user input (e.g., an embedding representation of the words in the natural language input). The system may also (e.g., using a trained machine learning component) determine a tone of the user with respect to the natural language user input. The system may further determine a topic of the natural language user input.

The skill component may use a trained machine learning model to process the ASR results data (in the situation where the natural language user input is spoken), the lexical embedding, the tone, and the topic to generate state data for the present turn of the skill component session.

As used herein, a "session" refers to data transmissions between the skill component and a user [e.g., through a user device(s)] that all relate to a single "conversation" between the skill component and the user that may have originated with a single user input initiating the session. The session or conversation can be limited to a continuous series of interactions with the user, within a specific time frame, by specific start and/or ending commands or phrases, or similarly delineated. Thus, the data transmissions of a session may be associated with a same session identifier, which may be used by components of the skill component to track information across the session. Subsequent user inputs of the same session may or may not start with speaking of a wakeword. Each user input of a session may be associated with a different user input identifier such that multiple user input identifiers may be associated with a single session identifier.

As used herein, a "turn" of a session, or "session turn," refers to a user input and the corresponding skill component generated response to the user input. A session identifier may correspond to multiple session turns, where each session turn may be associated with a corresponding session turn identifier.

The skill component may determine past state including the state data of one or more past turns of the present dialog by accessing stored past state data associated with the user e.g., via a user profile of the user.

The skill component may use one or more trained machine learning models to process the state data and the past state data to generate an output to the user, where the output may be one or more of empathetic, grounding (i.e., asking a confirmatory question with respect to the system's understanding of the natural language user input), or structured to elicit further information from the user. In some embodiments, the skill component may receive any number of different sets of questions each corresponding to a different survey, where each set of questions include questions corresponding to different topics, and the skill component may select an appropriate survey and generate the output based on one of the questions of the survey corresponding to the same or a similar topic as the natural language user input.

In some embodiments, the skill component may process the state data to determine the natural language user input corresponds to a topic, process the past state data to determine a past topic of the dialog, determine a difference between the topics, and, in response to the difference, generate the output to the natural language user input to request confirmation of the lexical embedding determined for the natural language user input.

When the natural language user input is a spoken input, the skill component may generate an acoustic embedding of the spoken natural language user input, and the skill component may generate the state data further using the acoustic embedding.

In another aspect of the present disclosure, the system may receive a natural language user input, and determine the natural language user input is a request for initiating communications with another person, such as a professional service provider. The system may determine at least one characteristic of the natural language user input. The skill component may, using the at least one characteristic, determine state data indicating a topic of the natural language user input and/or a level associated with the natural language user input. The skill component may also determine past state data for one or more past turns of the present dialog, and, using the state data and the past state data, generate a question related to the request for assistance.

In some embodiments, the natural language user input may be spoken, the system may perform ASR processing to generate ASR results data for the spoken natural language user input, and the at least one characteristic may include a lexical embedding of the spoken natural language user input.

In some embodiments, the past state data may indicate a topic of a past natural language user input of the present dialog, and the skill component may determine a difference between the topic of the present natural language user input and the topic of the past natural language user input, and generate the question based on the difference.

In some embodiments, the at least one characteristic may include a tone of the natural language user input, which may be derived using audio data (i.e., when the input is spoken) and/or the words in the natural language input.

In some embodiments, the question may be formulated as an empathetic phrase.

In some embodiments, the skill component may determine the user state satisfies a condition, and may generate the question based on the user state satisfying the condition.

In some embodiments, the skill component may receive a set of questions for obtaining information related to the request for assistance, and may determine the question, from among the set of question, based on the topic of the instant natural language user input.

In some embodiments, the natural language user input may be spoken, the system generate an acoustic embedding of the spoken natural language user input, and the at least one characteristic may include the acoustic embedding.

A system according to the present disclosure will ordinarily be configured to incorporate user permissions and only perform activities disclosed herein if approved by a user. As such, the systems, devices, components, and techniques described herein would be typically configured to restrict processing where appropriate and only process user data in a manner that ensures compliance with all appropriate laws, regulations, standards, and the like. The system and techniques can be implemented on a geographic basis to ensure compliance with laws in various jurisdictions and entities in which the components of the system and/or user are located.

FIG. 1 illustrates a system 100 for processing a user input related to a skill component configured to perform a conversational assessment of a user's state, according to embodiments of the present disclosure. The system 100 may include a user device 110, local to the user 105, in communication with a supporting device(s) 120 via a network(s) 199. The network(s) 199 may include the Internet and/or any other wide- or local-area network, and may include wired, wireless, and/or cellular network hardware. As illustrated in FIG. 1, the supporting device(s) 120 may include an orchestrator component 130, an ASR component 150, an NLU component 160, a post-NLU ranker component 165, and a skill component 190a configured to perform a conversational assessment of a state of the user 105. Although the figures illustrate the components in a particular arrangement, one skilled in the art will appreciate that different combinations and/or arrangements of the components are possible depending on the system's configuration without departing from the present disclosure. Moreover, it is noted that one or more of the components of the supporting device(s) 120 noted above may be implemented by the user device 110.

In some embodiments, the supporting device(s) 120 may include all of the components illustrated in the dashed box in FIG. 1. In some embodiments, the user device 110 may include all of the components illustrated in the dashed box in FIG. 1. In some embodiments, the supporting device(s) 120 and the user device 110 may each include at least one of the components illustrated in the dashed box in FIG. 1.

Referring to FIG. 1, the user 105 may provide a user input to the user device 110, and the user device 110 may generate and send, to the supporting device(s) 120, input data 125 corresponding to the user input. For example, the user 105 may speak an utterance (e.g., a spoken natural language user input) and the user device 110 may receive the utterance as input (analog) audio and generate (digitized) input audio data corresponding to the audio, where the input audio data forms at least a portion of the input data 125. For further example, the user 105 may provide a typed natural language user input as input text, and the user device 110 may generate input text data corresponding to the input text, wherein the input text data forms at least a portion of the input data 125. Other types of user inputs may also be processed using the techniques described herein. Some user inputs may be converted to a different form for further processing. For example, the input data 125 may include image data representing a gesture (e.g., pointing to an object, showing a number, etc.) performed by the user 105 and the supporting device(s) 120 may process the image data to determine data (e.g., text data, intent data, entity data, etc.) representing a meaning of the gesture input.

The user device 110 may send the input data 125 to the supporting device(s) 120 via an application that is installed on the user device 110 and associated with the supporting device(s) 120. An example of such an application is the Amazon Alexa application that may be installed on a smart phone, tablet, or the like.

The supporting device(s) 120 may receive (step 1), at the orchestrator component 130, the input data 125 representing the user input. In situations where the input data 125 is or includes input audio data of a spoken natural language user input, the orchestrator component 130 may send (step 2) the input audio data to the ASR component 150. The ASR component 150 may process the input audio data to generate ASR results data corresponding to the spoken natural language user input, which the ASR component 150 may send (step 2) to the orchestrator component 130. The ASR results data may include one or more ASR hypotheses, where an ASR hypothesis is a digital natural language representation (e.g., text or tokenized representation) of the spoken natural language input. Example processing of the ASR component 150 is described in detail herein below with respect to FIG. 10.

The orchestrator component 130 may send (step 3) the ASR results data to the NLU component 160. Alternatively, in situations where the input data 125 is or includes input text data of a typed natural language user input, the orchestrator component 130 may send the input text data to the NLU component 160 at step 3, without sending and receiving data to and from the ASR component at step 2. The NLU component 160 may be configured to process the ASR results data (or input text data) to generate NLU results data. The NLU results data may include one or more NLU hypotheses, each representing a respective semantic interpretation of the natural language user input as represented in the ASR results data (or input text data). For example, a NLU hypothesis may include an intent determined by the NLU component 160 to represent the natural language user input. A NLU hypothesis may optionally also include one or more entity types and corresponding entity values corresponding to entities determined by the NLU component 160 as being referred to in the natural language user input. Example processing of the NLU component 160 is described herein below with respect to FIG. 9. The NLU component 160 may send (step 3) the NLU results data to the orchestrator component 130.

The orchestrator component 130 may send (step 4) the NLU results data to a post-NLU ranker component 165. The post-NLU ranker component 165 is configured to process the NLU results data and other data to determine a skill component 190 to process with respect to the instant user input. Example components and processing of the post-NLU ranker component 165 are described in detail herein below with respect to FIG. 9. The post-NLU ranker component 165 may send (step 4), to the orchestrator component 130, a skill identifier corresponding to the skill that is to process with respect to the instant user input. In some embodiments, the post-NLU ranker component 165 may send an n-best list of skill identifiers associated with corresponding confidence values.

In the example of FIG. 1, the instant user input may be "I feel depressed," "I want to start a coping skill," "I want to do my mental health check-in," "I am feeling anxious today," "Start my breathing exercise," etc., and the NLU results data may therefore include a "mental health" intent or a "request for assistance" intent. Consequently, the skill identifier, output by the post-NLU ranker component 165, may be that of the skill component 190a.

Upon receiving the identifier of the skill component 190a from the post-NLU ranker component 165, the orchestrator component 130 may send (step 5) the NLU results data to the skill component 190a.

Upon receiving the NLU results data, a greeting component 135, of the skill component 190a, may generate a natural language output corresponding to a greeting for the user 105. The greeting component 135 may use one or more NLG techniques to generate the natural language output. In some embodiments, the greeting component 135 may store text or token data corresponding to a standardized natural language greeting welcoming the user. In such embodiments, upon the skill component 190a receiving NLU results data, the greeting component 135 may send the text or token data to a TTS component 980 of the supporting device(s) 120, and the TTS component 980 may process, as described in detail herein below with respect to FIG. 9, to generate output audio data including the greeting in the form of synthesized speech. The output audio data may then be output to the user 105 via the user device 110. Alternatively, the greeting component 135 may store, or may otherwise have access to a storage including, the foregoing output audio data, and the greeting component 135 may cause the output audio data to be presented to the user 105 via the user device 110 upon the skill component 190a receiving the NLU results data at step 5. In some embodiments, the greeting component 135 may cause the standardized greeting to be displayed as an image, text, etc., using a display of or associated with the user device 110, in addition to or instead of causing output of the greeting as synthesized speech. An example of the standardized greeting is "Good morning. I am your virtual companion. I am excited to engage with you today." In other cases, a greeting personalized to the user 105, or context of the user input, may be presented. For example, the greeting may include the user's name, an appropriate greeting based on the time of day, an indication of the last time the user interacted with the skill component 190a (e.g., "It is good to speak with you again"), etc.

After the greeting component 135 causes the greeting to be output, a user verification component 140, of the skill component 190a, may be called (step 6) to verify the identity of the user 105. The user verification component 140 may verify the identity of the user 105 using one or more verification techniques, such as a spoken or typed passcode, voice recognition, and/or facial recognition. In some embodiments, the user verification component 140 may send, to a user recognition component 995 of the supporting device(s) 120, a request for a user identifier, corresponding to the user 105, as determined by the user recognition component 995. In response to receiving the request, the user recognition component 995 may process, as described in detail herein below with respect to FIGS. 12 and 13, to determine the user identifier of the user, and may send the user identifier to the user verification component 140.

Upon verifying the identity of the user 105 (i.e., upon receiving the user identifier), the skill component 190a may create a new session (i.e., may generate a session identifier and commence associating data of the session with the session identifier). The session identifier may be associated with any of the operations described herein until the skill component 190a ends the session.

After the user 105 is verified, and optionally after the new session is created (i.e., in the scenario where the present user input is a first user input of the instant session), a check-in component 145, of the skill component 190a, may be called (step 7), by the user verification component 140 or another system component, to determine if a conversational assessment of the user 105 is to be performed. The check-in component 145 may be configured by an assistance (e.g., health care) provider or by the user 105. For example, the user 105 may input, to the system 100, a preference indicating when (e.g., never, every time the user 105 commences a new session with the skill component 190a, daily, weekly, monthly, etc.) a conversational assessment of the user 105 is to be performed. Similarly, for example, an assistance (e.g., health care) provider (e.g., primary care physician, psychologist, psychiatrist, etc.) may indicate, to the system 100 and with permission of the user 105, when and/or how often a conversational assessment of the user 105 is to be performed.

The check-in component 145 may determine whether a conversational assessment, of the user 105, is to be performed based on an instruction provided by an assistance (e.g., health care) provider, a preference of the user 105, the content of the user input (e.g., where the user indicates a mood or state of stress, sadness, or similar state) and/or the instant user input specifically requesting a conversational assessment.

If the check-in component 145 determines that a conversational assessment of the user 105 is not to be performed presently, then the check-in component 145 may cause (step 8) a listener component 175, of the skill component 190a, to execute. Generally, the listener component 175 may cause an open-ended question to be output to the user 105 in an effort to gain information for use in processing by one or more components of the skill component 190a illustrated in FIG. 8.

Conversely, if the check-in component 145 determines that a conversational assessment of the user 105 is to be performed, the check-in component 145 may query (step 9) a topic history storage 170, of the skill component 190a, for topic history data associated with the user identifier of the user 105 and/or the device identifier of the user device 110. The topic history storage 170 may store topic history data from one or more past sessions involving the skill component 190a and one or more users of the system 100. Topic history data, for a given past session, may be associated with a user identifier of the user that engaged in the past session and/or a device identifier of the user device used to perform the past session, and may include information about one or more topics (e.g., problems with sleeping, isolation, anxiety, depression, loneliness, personal struggles, etc.) discussed during the past session, and may include one or more pairs of data, where each pair includes an answer provided by the user during the past session in response to one or more corresponding outputs of the skill component 190a, and a topic corresponding to the output/answer.

In response to the check-in component 145 determining that a conversational assessment of the user 105 is to be performed, the check-in component 145 may send (step 10), to the listener component 175, an indication that a conversational assessment is to be performed along with any topic history data received in response to the query at step 9.

In response to receiving the foregoing indication, and optionally topic history data, from the check-in component 145, the listener component 175 may initiate a conversation with the user 105 for the purpose of performing the conversational assessment. Specifically, in response to receiving the indication and optionally the topic history data, the listener component 175 may generate (e.g., using NLG processing) a question that elicits information to perform the conversational assessment. In situations where the listener component 175 receives topic history data at step 10, the listener component 175 may generate the question to correspond to one or more topics represented in the topic history data. For example, the topic information may include a topic, and the listener component 175 may generate a question to confirm the topic. For example, if the topic history data indicates a "trouble sleeping" topic, then the listener component 175 may generate (e.g., using NLG processing) the question to ask if the user 105 is still having trouble sleeping.

If the listener component 175 does not receive any topic history data at step 10, such as when the user input, received at step 1 is the initial user input of the present session between the skill component 190*a* and the user 105, then the listener component 175 may generate (e.g., using NLG processing) the question to be an open-ended question, such as "how are you doing today," or may turn a prior user input into a question (e.g., if the user input received at step 1 indicates the user 105 is feeling sad, the listener component 175 could generate a question asking why or how long the user has felt sad).

In some embodiments, the listener component 175 may cause the question to be output as synthesized speech to the user 105 using the user device 110. For example, the listener component 175 may generate the question as text or token data, and may cause the text or token data to be sent to the TTS component 980. The TTS component 980 may process, as described in detail herein below with respect to FIG. 9, to generate output audio data including the question in the form of synthesized speech, and the output audio data may be output to the user 105 via the user device 110. In some embodiments, the listener component 175 may cause the question to be displayed as an image, text, etc., using a display of or associated with the user device 110, in addition to or instead of causing output of the question as synthesized speech.

After the listener component 175 causes the question to be presented to the user 105, the user 105 may provide a responsive user input to the question via the user device 110, which the user device 110 may send to the orchestrator component 130 as input data. For example, the user device 110 may receive audio of a responsive spoken natural language user input, where the responsive spoken natural language user input may include one or more sentences. The user device 110 may generate input audio data corresponding to the audio of the spoken responsive natural language user input, and send the input audio data to the orchestrator component 130 as or as part of the input data. For further example, the user device 110 may receive typed text of a responsive natural language user input, where this responsive natural language user input may include one or more sentences. In this example, the user device 110 may generate input text data corresponding to the typed text, and send the input text data to the orchestrator component 130 as or as part of the input data. In addition to sending the input audio data or input text data, the user device 110 may generate the input data to include an indication that the input data corresponds to a response to the question output by the listener component 175. In the example where the input data is or includes input audio data, the orchestrator component 130 may send the input audio data to the ASR component 150, and the ASR component 150 may process, as described in detail herein below with respect to FIG. 9, to generate ASR results data.

In response to the input data including the indication that the input data corresponds to a response to the question output by the listener component 175, the orchestrator component 130 may forego causing NLU processing to be performed on the ASR results data, or input text data in the situation that a typed natural language user input is provided in response to the question. Instead, the orchestrator component 130 may send the ASR results data, or the input text data, to the listener component 175 along with an indication that the ASR results data, or input text data, corresponds to a response to the question output by the listener component 175.

In response to receiving the ASR results data, or input text data, and the foregoing indication, the listener component 175 may send (step 11), to the conversational assessment component 180, the ASR results data, or input text data, and the topic history data to the extent said topic history data is received at step 10 by the listener component 175. The listener component 175 and conversational assessment component 180 may operate in coordination with one another to use prompts and questions to encourage the user 105 to identify (e.g., mental health) topics, and/or guide the user 105 to next steps. In this iterative process, the listener 175 drives the output of questions and prompts to the user via the user device 110 and the conversational assessment component 180 drives the identification of the next prompt or question as well as the compiling of the response data. The conversational assessment component 180 is described in detail herein below with respect to FIG. 2. Once the conversational assessment component 180 has finished performing the conversational assessment, as described herein below, the conversational assessment component 180 may send (step 12), to a recommendation ranking component 185 of the skill component 190*a*, recommendation data including a n-best list of recommendations based on the conversational assessment. The recommendation ranking component 185 may use the recommendation data to determine one or more further actions to be taken by the user 105 and/or skill component 190*a*, as is described in detail herein below with respect to FIG. 8.

Figure 2:
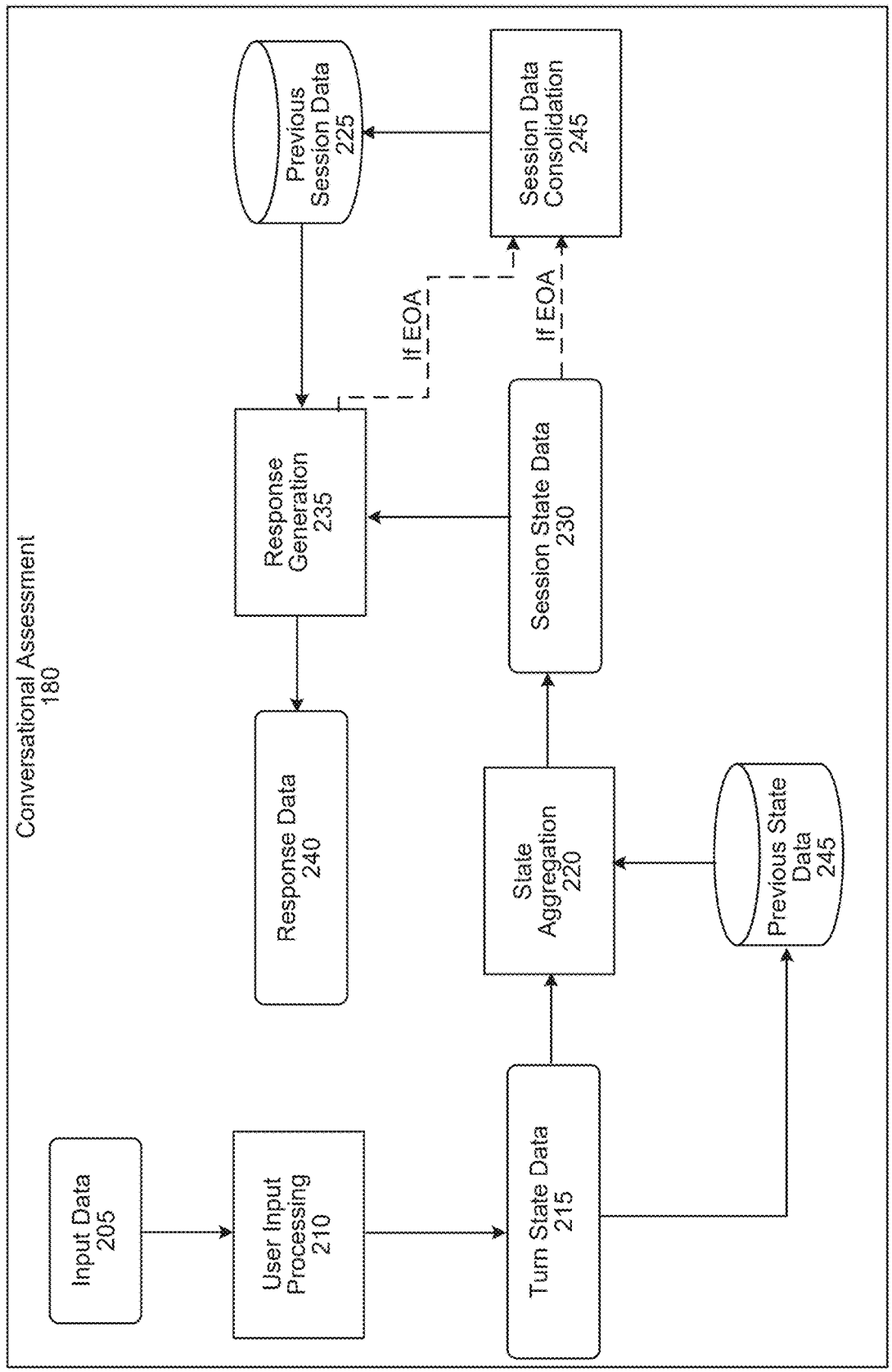
FIG. 2 is a conceptual diagram illustrating example components and processing of a conversational assessment component, according to embodiments of the present disclosure.

FIG. 2 is a conceptual diagram illustrating example components and processing of the conversational assessment component 180, according to embodiments of the present disclosure. The conversational assessment component 180 may perform a conversational assessment with the user 105 to elicit information from the user 105 and determine a state (e.g., mental health level) for the user 105. In some embodiments, the conversational assessment component 180 may perform a voice-based conversational mental health level assessment and may use a combination of open-ended questions and questions from stored mental health questionnaires, such as an nine-item Patient Health Questionnaire (PHQ-9) or a seven-item Generalized Anxiety Disorder (GAD-7) screening.

Conventionally, when administering PHQ-9, the individual taking the questionnaire is instructed to, using the below response scale, indicate how often, over the last two weeks, the individual has been affected by the following problems: (1) little interest or pleasure in doing things; (2) feeling down, depressed, or hopeless; (3) trouble failing asleep, staying asleep, or sleeping too much; (4) feeling tired or having little energy; (5) poor appetite or overeating; (6) feeling bad about oneself, or that the individual feels as if the individual is a failure or has let the individual or a its family down; (7) trouble concentrating on things, such as reading the newspaper or watching television; (8) moving or speaking so slowly that other people have notices, or the opposite, being so fidgety or restless that the individual has been moving around a lot more than usual; and (9) thoughts that the individual would be better off dead or of hurting the individual in some way. In some embodiments, question 9 above may be omitted from the conversational assessment performed by the conversational assessment component 180, as a user that answers yes to question 9 needs assistance for suicide risk, something that the skill component 190*a* may not be configured to provide.

PHQ-9 has a response scale of: not at all (0 points); several days (+1 point); more than half the days (+2 points); and nearly every day (+3 points). The individual's total PHQ-9 score is obtained by adding the score of all question responses. A total score of 0-4 represents the individual has a minimal level of depressive disorder, 5-9 represents the individual has a mild case of depressive disorder, 10-14 represents the individual has a moderate case of depressive disorder, 15-19 represents the individual has a moderately severe case of depressive disorder, and 20+represents the individual has a severe case of depressive disorder.

Conventionally, when administering GAD-7, the individual taking the questionnaire is instructed to indicate how often, over the last two weeks, the individual has been affected by the following problems: (1) feeling nervous, anxious, or on edge; (2) not being able to stop or control worrying; (3) worrying too much about different things; (4) trouble relaxing; (5) being so restless that it is hard to sit still; (6) becoming easily annoyed or irritable; and (7) feeling afraid as if something awful might happen.

GAD-7 has a response scale of: not at all (0 points); several days (+1 point); more than half the days (+2 points); and nearly every day (+3 points). The individual's total GAD-7 score is obtained by adding the score of all question responses. A total score of 0-4 represents the individual has a minimal case of generalized anxiety disorder, 5-9 represents the individual has a mild case of generalized anxiety disorder, 10-14 represents the individual has a moderate case of generalized anxiety disorder, and 15+represents the individual has a severe case of generalized anxiety disorder.

The conversational assessment component 180 may actively assess the state (e.g., mental health level) of a user using runtime generated confidence scores based on the user's responses to questions generated by the conversational assessment component 180. In generating questions to the user 105, and when determining when to conclude the present conversational assessment, the conversational assessment component 180 may leverage one or more user states (e.g., mental health levels) and/or one or more topics from past sessions. In some embodiments, the number of possible conversational assessment questions may be limited, but the conversational assessment component 180 may use paraphrasing, contextual referencing, and empathetic speech characteristics to improve naturalness of the user experience.

Referring to FIG. 2, a user input processing component 210 of the conversational assessment component 180 may receive input data 205. As mentioned above, the input data 205 may be ASR results data generated for a spoken natural language user input responsive to a question output by the listener component 175, or may be input text data of a typed natural language user input responsive to the question output by the listener component 175. The user input processing component 210 may, perform or caused to be performed, one or more of NLU processing, topic determination processing, acoustic embedding processing, tone detection processing, and state assessment processing.

Figure 3:
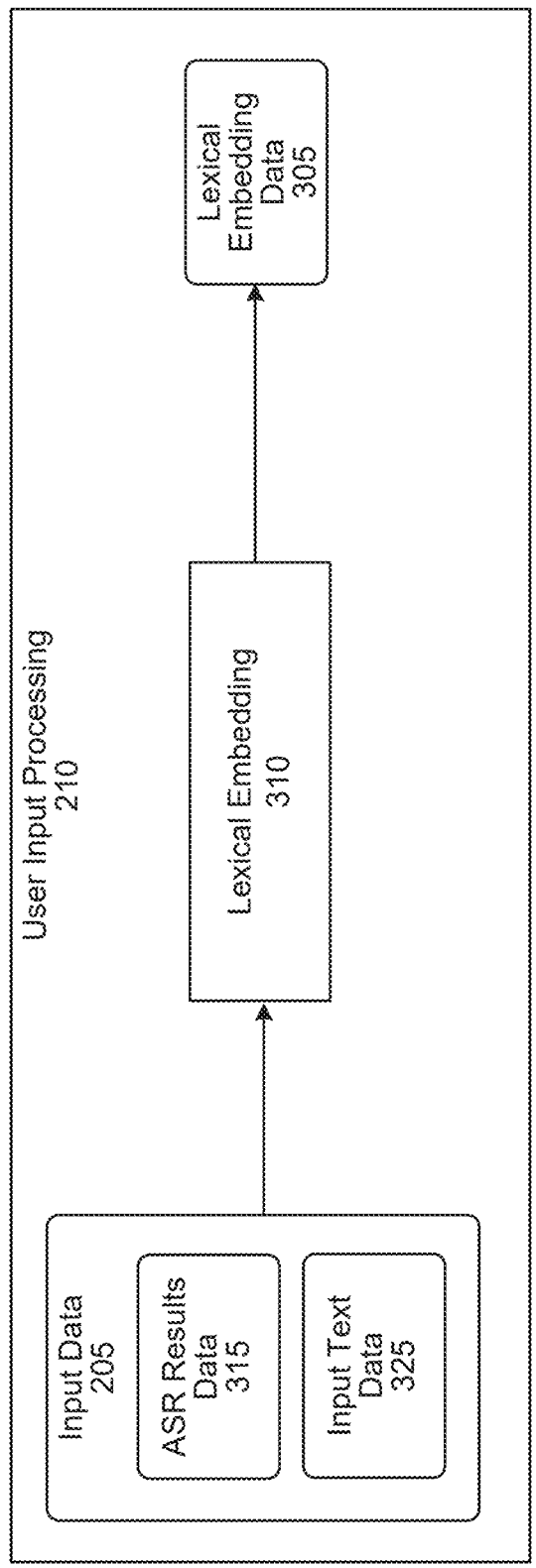
FIG. 3 is a conceptual diagram illustrating example processing that may be performed by a natural language understanding (NLU) component of the system, according to embodiments of the present disclosure.

The user input processing component 210 may include a lexical embedding component 310, illustrated in FIG. 3. Alternatively, the supporting device(s) 120 may implement the lexical embedding component 310 separate from the user input processing component 210.

With reference to FIG. 3, the lexical embedding component 310 may receive the input data 205, in the form of the ASR results data 315 or input text data 325, and output lexical embedding data 305 corresponding to the user input as represented in the input data 205.

It is noted that the lexical embedding component 310 is configured differently from the NLU component 160, which is described in detail herein below with respect to FIG. 9. That is, the lexical embedding component 310 is not configured to perform, among other things, intent classification processing and named entity recognition processing as described with respect to the NLU component 160. Rather, the lexical embedding component 310 is configured to generate an embedding representation of the word sequence of the ASR results data 315 or the input text data.

The lexical embedding component 310 may be configured using different approaches, all of which are within the scope of the present disclosure. In some embodiments, the lexical embedding component 310 may utilize one or more machine learning techniques. In some embodiments, the lexical embedding component 310 may implement a Bidirectional Encoder Representations from Transformers (BERT) model to generate the lexical embedding data 305. The lexical embedding component 310 may generate a single lexical embedding data 305 (i.e., a single embedding representation) for the input data 205, regardless of whether the user input of the input data 205 includes one sentence or more than one sentence.

The structure of the lexical embedding component 310, and the structure of the lexical embedding data 305 output therefrom, may depend on the type of state assessment being performed by the conversational assessment component 180. For example, if the conversational assessment component 180 is assessing for depression and anxiety, the lexical embedding data 305 may be a user input-level embedding generated using a large language model (e.g., BERT). From this type of lexical embedding data, with or without combination with an acoustic embedding of the user input, higher level semantic data (e.g., tone, emotion, and topic) may be derived and used to perform a state assessment as described elsewhere herein.

In some embodiments, one or more lexical descriptors (e.g., language complexity, specific language constructs, use of pronouns, and distribution of pauses) may be generated and used to perform the state assessment. These one or more lexical descriptors may be derived from text of a user input and/or word timing information for a user input.

Figure 4:
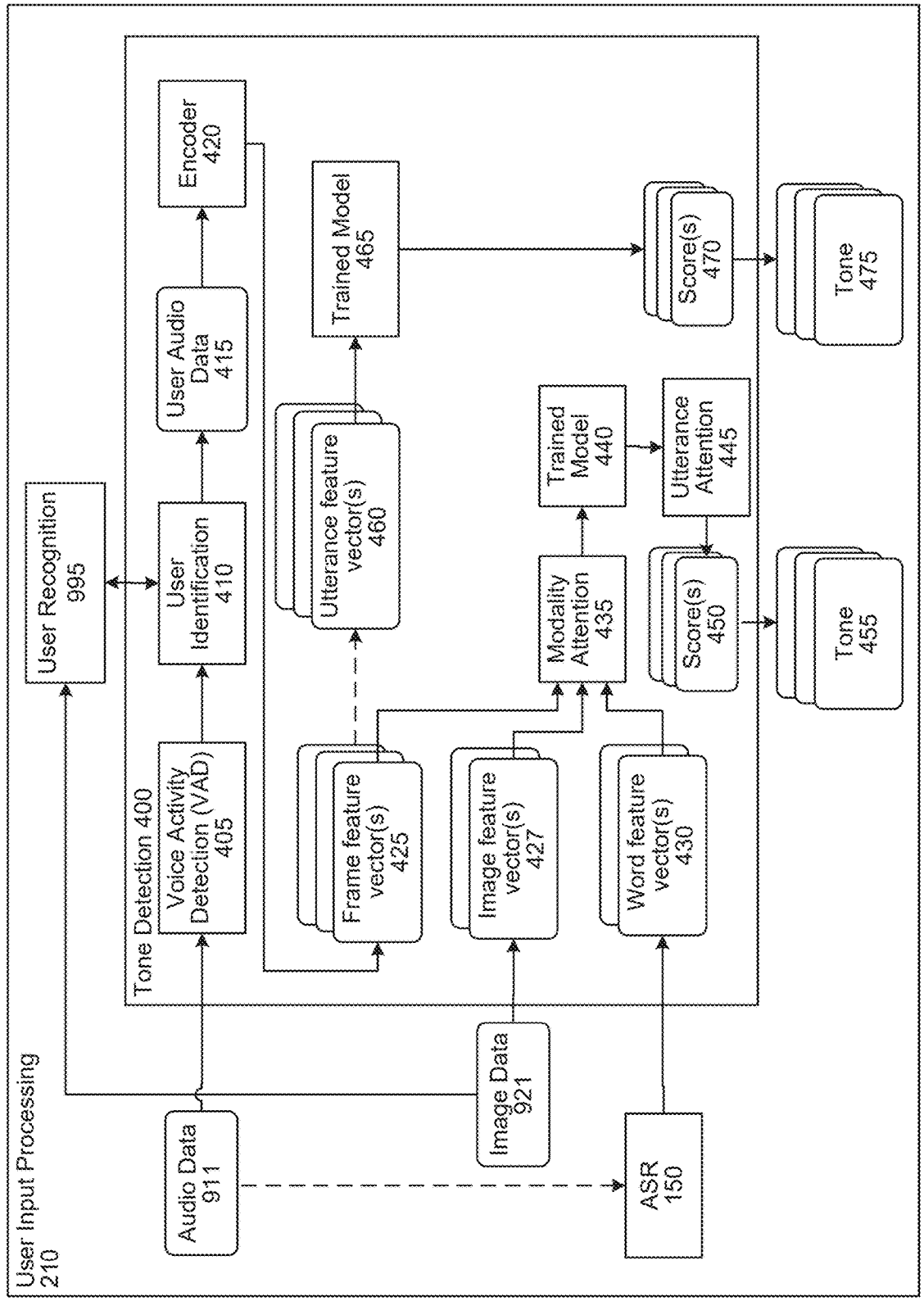
FIG. 4 is a conceptual diagram illustrating a tone detection component, according to embodiments of the present disclosure.

The user input processing component 210 may additionally or alternatively include a tone detection component 400, illustrated in FIG. 4, or the user input processing component 210 may additionally or alternatively communicate with the tone detection component 400 as otherwise implemented by the supporting device(s) 120.

With reference to FIG. 4, the tone detection component 400 may determine a user tone based on audio data 911 (e.g., the input audio data represented by the ASR results data 315 of the instant spoken natural language user input responsive to the question output by the listener component 175), image data 911, and other data. Although certain configurations/operations of the tone detection component 400 are illustrated in FIG. 4 and described herein, other techniques/configurations of tone detection may be used depending on system configuration.

The tone detection component 400 may include a voice activity detection (VAD) component 405, a user identification component 410, an encoder component 420, a modality attention layer 435, a trained model component 440, an utterance attention layer 445, and a trained model component 465. The audio data 911 captured by a user device 110 may be inputted into the VAD component 405. The VAD component 405 may determine if the audio data 911 includes speech spoken by a human or voice activity by a human, and may determine a portion of the audio data 911 that includes speech or voice activity. The VAD component 405 may send the portion of the audio data 911 including speech or voice activity to the user identification component 410. The VAD component 405 may employ voice activity detection techniques. Such techniques may determine whether speech is present in audio data based on various quantitative aspects of the audio data, such as the spectral slope between one or more frames of the audio data; the energy levels of the audio data in one or more spectral bands; the signal-to-noise ratios of the audio data in one or more spectral bands; or other quantitative aspects. In other examples, the VAD component 405 may implement a limited classifier configured to distinguish speech from background noise. The classifier may be implemented by techniques such as linear classifiers, support vector machines, and decision trees. In still other examples, the user device 110 may apply Hidden Markov Model (HMM) or Gaussian Mixture Model (GMM) techniques to compare the audio data to one or more acoustic models in storage, which acoustic models may include models corresponding to speech, noise (e.g., environmental noise or background noise), or silence. Still other techniques may be used to determine whether speech is present in audio data.

The user identification component 410 may communicate with the user recognition component 995 to determine user audio data 415 that corresponds to a particular user profile. The user recognition component 995 may recognize one or more users as described in connection with FIGS. 12 and 13. The user audio data 415 may be a portion of the audio data 911 that includes speech or one or more utterances from a particular user associated with the user profile. In other words, audio data representing a particular user's speech may be isolated and stored as the user audio data 415 for further analysis. In an example embodiment, the user may be associated with or using the user device 110, and may have provided permission to the system 100 to record and analyze his or her voice/conversations to determine a tone corresponding to the conversation.

The user audio data 415 may be input into the encoder component 420 to determine frame feature vector(s) 425. The encoder component 420 may be a bidirectional LSTM. The frame feature vector(s) 425 may represent audio frame level features extracted from the user audio data 415. One frame feature vector 425 may represent audio frame level features for an audio frame of 20 ms of the user audio data 415. The frame feature vector(s) 425 may be derived by spectral analysis of the user audio data 415. The tone detection component 400 may determine the portions of user audio data 415 that correspond to individual words and may extract acoustic features from the respective portions of audio using the encoder component 420.

In some embodiments, the frame feature vector(s) 425 may be used to determine utterance feature vector(s) 460 representing utterance-level features of one or more utterances represented in the user audio data 415. The utterance feature vector(s) 460 may be determined by performing statistics calculations, delta calculation and other processing on the frame feature vector(s) 425 for the audio frames corresponding to an utterance of interest. As such, the utterance feature vector(s) 460 may be a feature matrix whose dimensions are based on the number of audio frames corresponding to the utterance of interest and the dimension of the corresponding frame feature vector 425. The utterance feature vector(s) 460 may be a high-level function or other mathematical functions representing the utterance-level features.

The ASR component 150, as described above, may generate ASR results data, for example including text data representative of one or more utterances represented in the audio data 911. In some examples, the system sends audio data 911 to the ASR component 150 for processing. In other examples, the system sends user audio data 415 to the ASR component 150 for processing. The ASR output may be represented as word feature vector(s) 430, where each word feature vector 430 may correspond to a word in the text data determined by the ASR component 150 and may represent lexical information of the utterance. The word feature vector 430 may be a word embedding.

In an example embodiment, the tone detection component 400 determines that the user audio data 415 includes an entire utterance. That is, the tone detection component 400 may determine that a beginpoint of the user audio data 415 corresponds to a beginpoint of an utterance, and an endpoint of the user audio data 415 corresponds to an endpoint of the utterance. In this case, the frame feature vector(s) 425 and the word feature vector(s) 430 may represent all the words in one utterance.

The tone detection component 400 may also input image data 911 which may come from still images, an image feed of video data, or the like for example from one or more cameras of user device 110 or otherwise. The image data 911 may include a representation of a user which the system may analyze to determine the user's tone. Image data 911 may be processed by an encoder (not illustrated) to determine image feature vector(s) 427. Such an encoder may be included as part of tone detection component 400 or may be located separately, in which case image feature vector(s) 427 may be input into tone detection component 400 in addition to or instead of image data 911. The image data/feature vectors may be analyzed separately by tone detection component 400 if audio data/ASR data is unavailable. The image data/feature vectors may also be analyzed in conjunction with the audio data/ASR results data.

The tone detection component 400 may align a frame feature vector 425 with a corresponding word feature vector 430 such that the pair represents acoustic information and lexical information, respectively, for an individual word in the utterance represented in user audio data 415. The tone detection component 400 may similarly align one or more image feature vector(s) 427 with one or more frame feature vector(s) 425 and/or corresponding word feature vector(s) 430 so the appropriate image(s) are matched with the frames/ASR results data thus allowing the system to consider the audio, content and image of the user talking when performing tone analysis. The frame feature vectors 425, image feature vector(s) 427, and the word feature vectors 430 may be processed by the trained model 440 simultaneously.

The trained model 440 may process the frame feature vector(s) 425 and corresponding word feature vector(s) 430 using a machine learning model. In some embodiments, the tone detection component 400 includes a modality attention component 435 configured to determine how much acoustic information versus how much lexical information versus how much image information from the respective feature vectors 425/427/430 should be used by the trained model 440. In some cases the acoustic information corresponding to certain words may indicate a certain tone based on how the words were spoken by the user. In other cases the lexical information corresponding to certain words may indicate a certain tone based on the meaning or semantic of the word. For example, words "hey you" spoken with a certain level of anger, as indicated by the corresponding acoustic information, may indicate a tone of anger, while the same words "hey you" spoken with no level of anger or excitement, as indicated by the corresponding acoustic information, may indicate a tone of neutral. As a lexical example, the words "I am angry" may indicate a tone of anger based on the corresponding lexical information. The modality attention component 435 may assign a weight or percentage to the data represented by the acoustic feature vectors, the data represented by the image feature vectors, and the data represented by the lexical feature vectors to indicate the importance of each to the trained model 440.

The trained model 440 may be a neural network, for example a bi-directional LSTM. The output of the trained model 440 may be fed into an utterance attention component 445. The utterance attention component 445 may employ a neural network, for example a recurrent neural network, although the disclosure is not limited thereto. The utterance attention component 445 may be configured to emphasize relevant portions of an input utterance. The utterance attention component 445 may be configured to take in output data from the trained model 440 and produce an output for every time step (e.g., a 10 ms audio frame). The utterance attention component 445 may be configured to aggregate information from different time intervals/audio frames of the input audio data to determine how certain parts of the utterance affects determining of the tone. For example, an acoustic representation of a first word in the utterance may indicate a high arousal implying anger, in which case the utterance attention component 445 is configured to realize that the first word corresponds to an anger tone and that that should affect the processing of the other words in the utterance to ultimately determine a tone corresponding to the utterance.

The utterance attention component 445 may output score(s) 450 indicating a tone 455 for the user audio data 415. The tone detection component 400 may predict from multiple tone categories, including but not limited to, happiness, sadness, anger and neutral. In an example embodiment, the tone 455 may be determined after score(s) 450 have been determined for a particular period of time of input audio data. In an example embodiment, the tone categories may be broad such as positive, neutral, and negative or may be more precise such as angry, happy, distressed, surprised, disgust, sad, joyous, humorous, or the like.

In some embodiments, the tone detection component 400 is configured to determine a tone 475 at an utterance-level. The tone detection component 400 may use contextual information from the entire utterance to determine an overall tone of the speaker when speaking the utterance. The tone detection component 400 may also use information conveyed by individual words in the utterance to determine the tone of the speaker when speaking the utterance. For example, particular words may represent a particular tone or emotion because of its meaning (lexical information), while some words may represent a particular tone or emotion because of the way it is spoken by the user (acoustic information). In other embodiments, the tone detection component 400 may be configured to determine a tone on a word level (that is for each word within an utterance).

As illustrated in FIG. 4, the trained model component 465 may process the utterance feature vector(s) 460 using a fully-connected neural network trained using techniques known to one of skill in the art. The trained model component 465 may output score(s) 470 indicating a tone 475 for the user audio data 415.

The tone detection component 400 may predict one of three tone categories 455/475. In some examples, the tone categories 455/475 may be positive, neutral, and negative. However, the disclosure is not limited thereto, and in other examples the tone categories 455/475 may be angry, neutral (e.g., neutral/sad), and happy without departing from the disclosure. Additionally or alternatively, the tone detection component 400 may predict any number of tone categories 455/475 without departing from the disclosure. For example, the tone detection component 400 may predict one of four tone categories 455/475, such as angry, sad, neutral, joyous, humorous, and happy, although the disclosure is not limited thereto.

The machine learning model for the trained model component 440/465 may take many forms, including a neural network. The trained model component 440/465 may employ a convolutional neural network and/or may employ a fully-connected neural network. In some examples, a neural network may include a number of layers, from input layer 1 through output layer N. Each layer is configured to output a particular type of data and output another type of data. Thus, a neural network may be configured to input data of type data A (which is the input to layer 1) and output data of type data Z (which is the output from the last layer N). The output from one layer is then taken as the input to the next layer. For example, the output data (data B) from layer 1 is the input data for layer 2 and so forth such that the input to layer N is data Y output from a penultimate layer.

While values for the input data/output data of a particular layer are not known until a neural network is actually operating during runtime, the data describing the neural network describes the structure and operations of the layers of the neural network.

In some examples, a neural network may be structured with an input layer, middle layer(s), and an output layer. The middle layer(s) may also be known as the hidden layer(s). Each node of the hidden layer is connected to each node in the input layer and each node in the output layer. In some examples, a neural network may include a single hidden layer, although the disclosure is not limited thereto and the neural network may include multiple middle layers without departing from the disclosure. In this case, each node in a hidden layer will connect to each node in the next higher layer and next lower layer. Each node of the input layer represents a potential input to the neural network and each node of the output layer represents a potential output of the neural network. Each connection from one node to another node in the next layer may be associated with a weight or score. A neural network may output a single output or a weighted set of possible outputs.

In one aspect, the neural network may be constructed with recurrent connections such that the output of the hidden layer of the network feeds back into the hidden layer again for the next set of inputs. For example, each node of the input layer may connect to each node of the hidden layer, and each node of the hidden layer may connect to each node of the output layer. In addition, the output of the hidden layer may be fed back into the hidden layer for processing of the next set of inputs. A neural network incorporating recurrent connections may be referred to as a recurrent neural network (RNN).

Neural networks may also be used to perform ASR processing including acoustic model processing and language model processing. In the case where an acoustic model uses a neural network, each node of the neural network input layer may represent an acoustic feature of a feature vector of acoustic features, such as those that may be output after the first pass of performing speech recognition, and each node of the output layer represents a score corresponding to a subword unit (such as a phone, triphone, etc.)

and/or associated states that may correspond to the sound represented by the feature vector. For a given input to the neural network, it outputs a number of potential outputs each with an assigned score representing a probability that the particular output is the correct output given the particular input. The top scoring output of an acoustic model neural network may then be fed into an HMM which may determine transitions between sounds prior to passing the results to a language model.

In the case where a language model uses a neural network, each node of the neural network input layer may represent a past word and each node of the output layer may represent a potential next word as determined by the trained neural network language model. As a language model may be configured as a recurrent neural network which incorporates some history of words processed by the neural network, the prediction of the potential next word may be based on past words in an utterance and not just on the most recent word. The language model neural network may also output weighted predictions for the next word.

Processing by a neural network is determined by the learned weights on each node input and the structure of the network. Given a particular input, the neural network determines the output one layer at a time until the output layer of the entire network is calculated.

Connection weights may be initially learned by the neural network during training, where given inputs are associated with known outputs. In a set of training data, a variety of training examples are fed into the network. Each example typically sets the weights of the correct connections from input to output to 1 and gives all connections a weight of 0. As examples in the training data are processed by the neural network, an input may be sent to the network and compared with the associated output to determine how the network performance compares to the target performance. Using a training technique, such as back propagation, the weights of the neural network may be updated to reduce errors made by the neural network when processing the training data. In some circumstances, the neural network may be trained with an entire lattice to improve speech recognition when the entire lattice is processed.

In some embodiments, the tone detection component 400 may be configured to output a finite list of tones (e.g., stressed, angry, sad, concerned, etc.).

The user input processing component 210 may additionally or alternatively include a topic extraction component 510, illustrated in FIG. 5, or the user input processing component 210 may additionally or alternatively communicate with the topic extraction component 400 as otherwise implemented by the supporting device(s) 120.

With reference to FIG. 5, the topic extraction component 510 may receive the input data 205, in the form of the ASR results data 315 or input text data 325, and output topic data 535 corresponding to the user input as represented in the input data 205. The topic extraction component 510 may be configured to in a variety of manners, all of which are within the scope of the present disclosure provided the topic extraction component 510 is configured to take as input the input data 205 and generate therefore topic data 535 corresponding to a topic of the user input.

In some embodiments, the topic extraction component 510 may use a machine learning model (e.g., a neural network) to determine the topic data 535. In some embodiments, the training data for the neural network may include one or more sessions and/or dialogs of one or more users, and the neural network may be trained to extract, from the session(s) and/or dialog(s) topics usable to perform a conversational assessment. In some embodiments, the ground truth for the neural network may come from sessions and/or dialogs, of one or more users, that are manually annotated with topic labels. In some embodiments, the topic labels may be sources from a fixed list of topics relevant to health care providers when assessing mental health. Table 1 below provides an example listing of topic types and corresponding topics of concern upon which the topic extraction component 510 may be trained, in some embodiments.

TABLE 1

Topic types with corresponding topics of concern.

| Topic Type | | Topics of Concern |
|---|---|---|
| Diagnostic indicators | Somatic | Sleep, Weight, Fatigue, Irritability, Concentration |
| | Affective | Mood, Self-esteem, Hopelessness, Stress, Worry |
| | Other | Suicidal thoughts |
| Health and Life Dimensions | | Work, Relationships, Finances, Physical activity, Addiction, Non-MH medical conditions, Grief, Post-partum |

The topic labels, upon which the neural network of the topic extraction component 510 is configured, may at least in part be formed by mining and annotating publicly available clinical interviews, media (e.g., movie) dialogs, and/or other dialog sources.

In some embodiments, the neural network may be configured using a multi-label classification problem, such that the neural network may be configured to detect, with reference to the examples in Table 1, a somatic-sleep topic, a somatic-fatigue topic, an affective-stress topic, etc.

Questions of mental health assessment surveys, such as PHQ-9 and GAD-7, may be associated with corresponding topics. In situations where the instant user input is received in response to the listener component 175 outputting a question from a mental health assessment survey, the topic data 535 may be generated to be the established topic of the question, and the neural network of the topic extraction component 510 need not process the input data 205 to determine the topic data 535.

In some embodiments, where the user input is not answering a question obtained from an established survey with corresponding topics, the topic extraction component 510 may process the lexical embedding data 305 to determine the topic data 535.

The user input processing component 210 may additionally or alternatively include an acoustic processing component 615, illustrated in FIG. 6, or the user input processing component 210 may additionally or alternatively communicate with the acoustic processing component 615 as otherwise implemented by the supporting device(s) 120.

In situations wherein the instant user input is a spoken natural language user input, the acoustic processing component 615 may process input audio data 911, of the spoken natural language user input, to generate acoustic embedding data 610 representing acoustic characteristics of the spoken natural language user input.

The present disclosure is not limited to any particular manner of configuring the acoustic processing component 615 to process the input audio data 911 and generate the acoustic embedding data 610. In some embodiments, the acoustic processing component 615 may be configured to identify sounds that may represent user happiness, sadness, anger, fear, etc., and may represent one or more of these sounds in the acoustic embedding data 610 to the extent one or more of the sounds are present in the input audio data 911.

For example, a snap or clap may indicate user happiness, the sound of a surface being hit may indicate user frustration or anger, and the fluctuation in tone of speech may indicate user fear.

Figure 7:
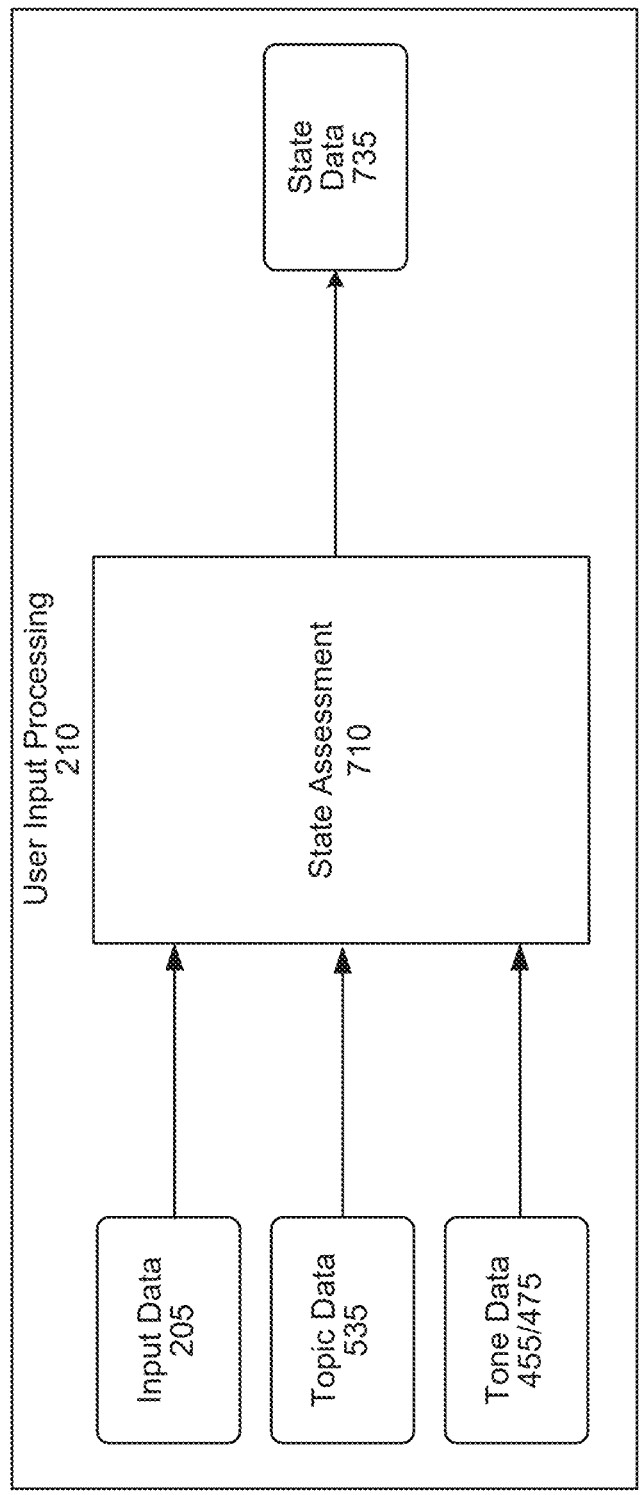
FIG. 7 is a conceptual diagram illustrating example processing that may be performed by a state assessment component of the system, according to embodiments of the present disclosure.

The user input processing component 210 may additionally or alternatively include a state assessment component 710, as shown in FIG. 7. The state assessment component 710 may be configured to determine a state (e.g., a mental health level), and associated confidence score, for the user 105 based on data received and generated for the present turn of the session between the conversational assessment component 180 and the user 105.

As illustrated in FIG. 7, the state assessment component 710 may receive as input the input data 205 (i.e., the ASR results data 315 or the input text data 325), the topic data 535, and the tone data 455/475, and state data 735 representing a state (e.g., mental health level) of the user 105 specific to the present turn of the session. The state data 735 may also include a confidence value [e.g., numerical (e.g., on a scale of 0 to 1) or binned score (e.g., low, medium, or high)] corresponding to the confidence of the state assessment component 710 in generating the state (e.g., mental health level) for the user 105 for the present turn of the session.

The state component 710 may incorporate a machine learning model to determine the state data 735. The machine learning model may be trained using responses to clinical surveys, such as PHQ-9 and GAD-7. As noted elsewhere herein, different responses to PHQ-9 and GAD-7 questions correspond to different scores. In some embodiments, the machine learning model may initially calculate the state (e.g., mental health level) of the user 105 as the score of the user's response to a PHQ-9 or GAD-7 question output by the listener component 175.

The state assessment component 710 may implement fuzzy matching or other techniques to correlate the response of the user 105, to a PHQ-9 or GAD-7 question, to a corresponding score in instances where the user's response does exactly match the accepted answer for a score. For example, the state assessment component 710 may use fuzzy matching to correlate a user response of "not at all" to the accepted answer of "no days."

The state assessment component 710 may adjust the aforementioned initial score for the present turn of the session based on the topic data 535. For example, one or more topics, determinable by the topic extraction component 510, may be considered not risky (e.g., in terms of mental health), and may result in the initial score being reduced. Conversely, one or more topics, determinable by the topic extraction component 510, may be considered risky (e.g., in terms of mental health), and may result in the initial score being increased.

The state assessment component 710 may additionally or alternatively adjust the score for the present turn of the session based on the tone data 455/475. For example, one or more tones (e.g., happy), determinable by the tone detection component 400, may be considered not risky (e.g., in terms of mental health), and may result in the score being reduced. Conversely, one or more tones (e.g., anger, sad, and the like), determinable by the tone detection component 400, may be considered risky (e.g., in terms of mental health), and may result in the score being increased.

In some embodiments, a machine learning model, of the state assessment component 710, may produce a confidence score for the state data 735. The confidence score may be a number between 0 and 1 that indicates a confidence of the output from the machine learning model. In some embodiments, the state component 710 may generate the confidence score using cross-question selection coherence and an answer-to-option matching score.

In some embodiments, the ground truth, for the machine learning model of the state assessment component 710, may be derived from self-reporting assessments of users and/or professional-administered assessments. The training data may be annotated to identify a most informative answer to open-ended prompts and/or multiple-choice questions. In some embodiments, a cross-prompt/question late fusion method may be utilized. The fusion model may learn relevant aspects of per user input prediction and cross-user input coherence. Depending on which questions/prompts are most informative, additive scoring methodology, from self-reporting questionnaires, may be leveraged in fusion.

Referring to FIG. 2, the user input processing component 210 may generate turn state data 215. The turn state data 215 is a representation of user input derivatives. The turn state data 215 may include the ASR results data 315 or the input text data 325 (depending on the form of the natural language user input), the lexical embedding data 305, the topic data 535, the acoustic embedding data 610, the tone data 455/475, and the state data 735. Thus, it will be appreciated that the turn state data 215 is specific to the present session turn. The turn state data 215 may be considered to represent one or more characteristics of the instant user input, where the lexical embedding of the user input is one characteristic, the acoustic embedding of the user input is another characteristic, the topic of the user input is yet another characteristic, etc.

The turn state data 215 may be sent to a previous state data storage 245 for use in processing a subsequent turn of the conversational assessment. The turn state data 215 may also be sent to a state aggregation component 220 of the conversational assessment component 180.

The state aggregation component may receive the turn state data 215, and may aggregate the turn state data 215, for the present turn of the session, along with the turn state data, generated with respect to one or more past turns of the session (i.e., in the case where the instant user input is not the initial user input of the session), to generate session state data 230. In such situations, the state aggregation component 220 may receive the turn state data, generated with respect to the one or more past turns of the session, from a previous state data storage 245. The state aggregation component 220 may execute a function to determine, at the time of the present turn, a session state that takes into account turn state data generated for one or more past turns of the session. In some embodiments, the session state data 230 may include a topic distribution for the session, the states (e.g., mental health levels) for the different turns of the session (i.e., assuming the present user input is not the initial user input of the session), and an action informativeness indication that represents whether the conversational assessment component 180 is presently able to make a recommendation to the user 105 (e.g., with respect to the user's mental health).

In the situation where the session state data 230 includes an action informativeness indication representing an end of the assessment (or "EOA" as illustrated in FIG. 2) has been reached, the session state data 230 may be sent to a session data consolidation component 245. The session data consolidation component 245 may execute a function to consolidate the entirety of the turn state data 215, for the session, into session data that is stored in a past session data storage 225.

The past session data storage 225 may store one or more instances of past session data for a user and/or device. As such, within the past session data storage 225, an instance of past session data may be associated with a user identifier of the user that engaged in the session and/or a device identifier of the user device that was used to perform the session. one or more past sessions of the user 105, up to the present session.

A response generation component 235, of the conversational assessment component 180, may receive the session state data 230. The response generation component 235 may also receive past session state data from the past session data storage 225. For example, the response generation component 235 may query the past session data storage 225 for past session data associated with the user identifier of the user 105 and/or the device identifier of the user device 110.

The response generation component 235 may use the session state data 230 and the past session data to determine response data 240 for presentation to the user 105. The response data 240 may be generated based on factors such as, for example, elicitation, grounding, empathy, and context.

The response generation component 235 may implement a trained machine learning model (e.g., a neural network) configured to process the session state data 230 and the past session data to determine whether the response data 240 is to include a question querying the user 105 for additional information. For example, this trained machine learning model, of the response generation component 235, may determine the response data 240 is to include the output "Last time you shared that sleep was a problem for you. Has your sleep been better, worse, or the same since last time?" To determine such, this trained machine learning model may take as input one or more questionnaire response-topic pairs from one or more past conversatinal assessments performed between the user 105 and the conversational assessment component 180, as represented in past session data received from the past session data storage 225. The response generation component 235 need not have access to audio of the past response(s) to make this determination. In response to the "elicitation" trained machine learning model determining the session state data 230 indicates the instant user input did not respond to the question output by the listener component 175, the elicitation trained machine learning model may determine the response data 240 is to include a free-speech prompt to ask about the impact of the issue of the question (e.g., "How has that been affecting your day to day life?"). When the response data 240 includes such a prompt, the conversational assessment component 180 may cause a command to be sent to the ASR component 150, where the command instructs the ASR component 150 to adjust its endpointing thresholds to ensure the entirety of a long-form response to the free-speech prompt is captured.

The response generation component 235 may additionally or alternatively implement a trained machine learning model (e.g., a neural network) configured to process the session state data 230 and the past session data to determine whether the response data 240 is to include a "grounding" question, that is a question that requests the user 105 repeat all or some of what the user 105 said (i.e., in the present spoken natural language user input) to get confirmation that the system properly understood the spoken natural language user input. For example, the response generation component 235 may determine a grounding question is to be output when the user's response to the question output by the listener component 175 is unclear (e.g., the user's response is "I'd say it's most of the time," but the system can interpret this as "half the days" or "nearly every day," where the state assessment component 710 is configured to handle these interpretations differently when generating the state (e.g., mental health level)). Continuing the foregoing example, the grounding question could be "Do you mean more than half the days, or nearly every day?" In some embodiments, the "grounding" trained machine learning model, of the response generation component 235, may determine a grounding question is to be output when the user input is a response to an established mental health survey question, such as that of PHQ-9 or GAD-7, and a trained answer-to-option machine learning model determines a matching uncertainty, of the user input to an established response to the question, exceeds a threshold. As another example, the session state data 230 may indicate the topic extraction component 510 was unable to determine which to two topics (e.g., overwhelmed or trouble sleeping) the instant user input corresponds to. Continuing this example, the response data 240 may correspond to "I am hearing that you are feeling overwhelmed, and having trouble sleeping. Is that right?"

The response generation component 235 may additionally or alternatively implement a trained machine learning model (e.g., a neural network) configured to determine whether the response data 240 is to include an empathetic phrase, such as "I see," "I understand," "mm-hmm," or "I'm sorry to hear that." The response generation component 235 may generate response data 240 to include speech synthesis markup language (SSML) for use by the TTS component 980 to generate synthesized speech to have an empathetic tone or speaking style, such as reduced pitch variability, lower overall pitch, slower rate of speaking, and/or breathier voice quality.

The response generation component 235 may generate the response data 240 with an empathetic tone to encourage the user 105 to continue speaking, especially when the user 105 may be discussing a difficult topic. The response generation component 235 may generate the response data 240 to summarize the input data 205. In some embodiments, the "empathetic" trained machine learning model, of the response generation component 235, may determine whether the response data 240 is to be empathetic based at least in part on the tone data 455/475 determined by the tone detection component 400 for the instant session turn.

In some embodiments, the response data 240 may be generated based on the output of two or more of the foregoing trained machine learning models of the response generation component. For example, the response data 240 may be generated to be a grounding question in an empathetic tone and/or including an empathetic phrase.

The response data 240 may be generated, in some embodiments, based on the confidence scores output by the individual models of the response generation component 235. For example, the response data 240 may be generated to correspond to the output of any model's output that is associated with a confidence score satisfying a threshold confidence score (e.g., a minimum or maximum threshold score depending on how the models are configured).

In some embodiments, the response generation component 235 may implement a single trained machine learning model configured to determine whether the response data 240 is to include an empathetic and/or grounding and/or elicitation output.

The machine learning model(s), of the response generation component 235, may be trained using annotated data collected from (e.g., spoken) responses to health care provider-administered mental health assessment questionnaires (e.g., PHQ-9/GAD-7) and/or (e.g., spoken) responses to health care provider-administered open-ended mental health assessment questions. Additionally or alternatively, the training data may include clinical diagnoses, annotated topics in responses to open-ended questions, mental health assessment participant demographic information, and/or speech data. Patient data will ordinarily not be used for training unless advance informed consent is provided.

The response generation component 235 may determine an end of the conversational assessment has been reached based on the determination(s) of the one or more trained machine learning models of the response generation component 235. The response generation component 235 may additionally or alternatively determine an end of the assessment has been reached based on the session state data 230. For example, the session state data 230 represent the present turn user input is "That is all for now," "Thank you for helping me" or some other like user input indicating the user 105 wishes to end the conversational assessment. Upon determining the end of the assessment (EOA) has been reached, the response generation component 235 may send the response data 240, generated for the present session turn, along with the session state data 230, to the session data consolidation component 245 for consolidation into past session data and storage in the past session data storage 225.

The conversational assessment component 180 may send the response data 240 to the listener component 175, which may cause the response data 240 to be presented to the user 105. For example, the response data 240 may include a natural language text or token representation of an output, and the listener component 175 may cause the text or token data to be sent to the TTS component 980, where the TTS component 980 processes to generate output audio data including the response in the form of synthesized speech, and the output audio data may be output to the user 105 via the user device 110. In some embodiments, the listener component 175 may cause the response to be displayed as an image, text, etc., using a display of or associated with the user device 110, in addition to or instead of causing output of the response as synthesized speech.

Figure 8:
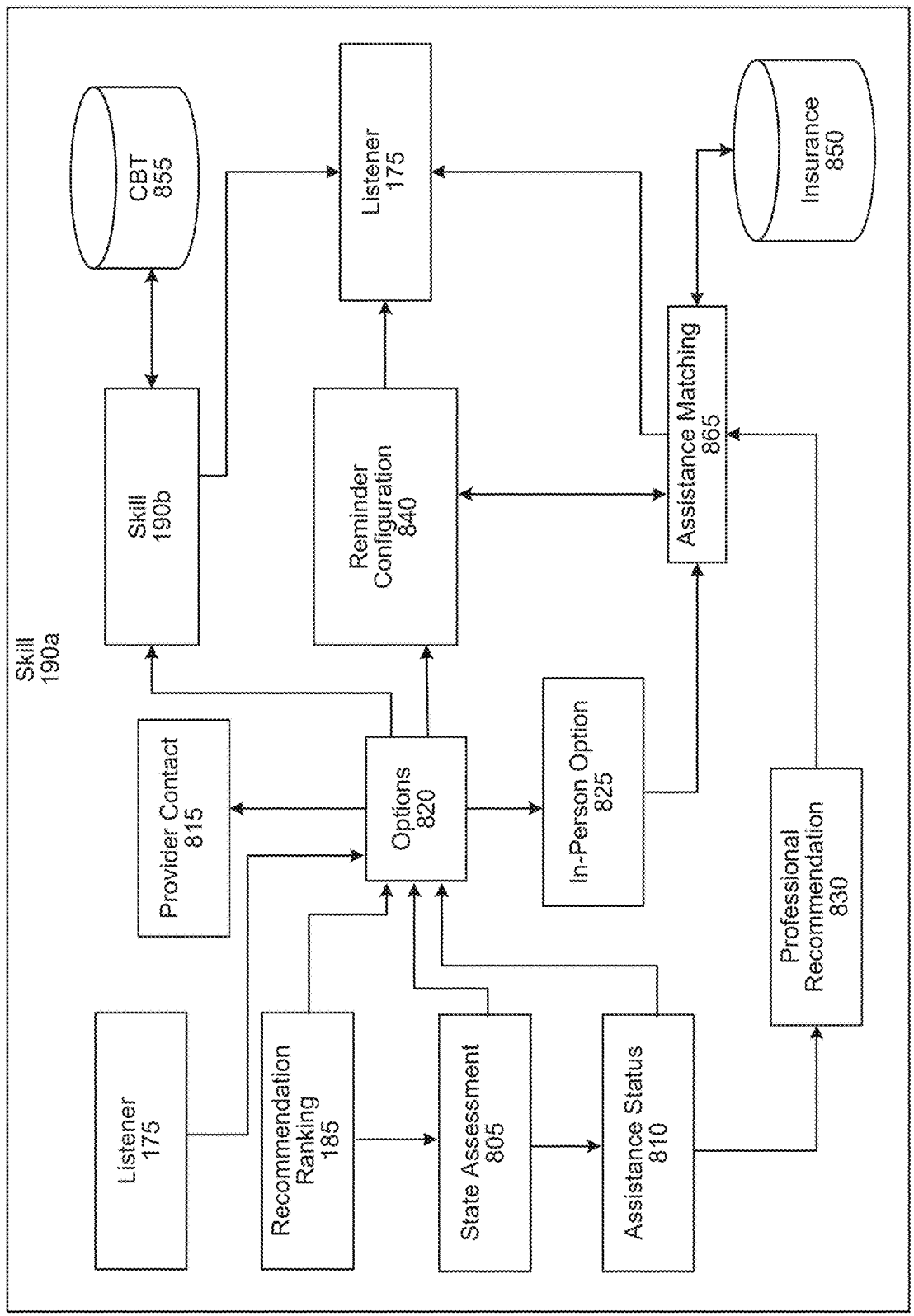
FIG. 8 is a conceptual diagram illustrating example components of, and processing that may be performed by, the skill component of FIG. 1, according to embodiments of the present disclosure.

FIG. 8 is a conceptual diagram illustrating example components of and processing that may be performed by the skill component 190a following the conversational assessment, or separate from a conversational assessment (e.g., in situations where the check-in component 145 determines a conversational assessment is not to be performed and causes the listener component 175 to process as described herein above with respect to step 8 in FIG. 1). As described in reference to FIG. 2, the conversational assessment component 180 may perform a conversational assessment of the user 105 to determine one or more recommendations for the user 105, such as performing coping exercises or contacting an assistant provider (e.g., therapist).

A recommendation ranking component 185, of the skill component 190a as illustrated in FIGS. 1 and 8) may receive (step 12 in FIG. 1) recommendation data from the conversational assessment component 180, where the recommendation data includes the one or more recommendations for the user 105. The recommendation ranking component 185 may rank the recommendations, in the recommendation data, based on various factors such as, but not limited to, preferences of the user 105, preferences of the assistance (e.g., health care) provider of the user 105, insurance information of the user 105, feedback of the user 105 received with respect to output of one or more past recommendations from one or more past conversational assessments, and/or usage rates of coping exercises. In some embodiments, the recommendation ranking component 185 may implement a trained machine learning model (e.g., neural network) that takes as input the recommendation data and one or more instances of the foregoing data, and outputs a ranked list of the recommendations in the recommendation data.

A state assessment component 805, of the skill component 190a, may determine a state (e.g., mental health level) of the user 105 with respect to one or more (e.g., mental health) conditions (e.g., anxiety, depression, etc.). For example, based on the state (e.g., mental health level) determined for the user 105 at the conversational assessment level by the conversational assessment component 180, the state assessment component 805 may determine if the user 105 has a low, moderate, or severe case of a condition (e.g., anxiety, depression, etc.).

If the state assessment component 805 determines the user 105 to have a severe condition, the state assessment component 805 may cause an assistance status component 810 to process and determine a current assistance (e.g., therapy) status of the user 105. If the state assessment component 805 determines the user has a moderate, or other less than severe, condition, then the state assessment component 805 may cause an options component 820 to determine a recommendation, from the ranked recommendations output from the recommendation ranking component 185, that the skill component 190a is to perform to assist the user 105.

The assistance status component 810 may determine the present assistance (e.g., therapy) status for the user 105. The assistance status component 810 may access user profile data (e.g., in the profile storage 970) of the user 105. The user profile data may indicate the assistance (e.g., therapy) status of the user 105, as well as the provider of the assistance (e.g., therapy). If the user 105 is presently receiving assistance (e.g., is presently in therapy), then the assistance status component 810 may cause the options component 820 to present an audio and/or display output to the user 105 that recommends the user 105 contact the assistance (e.g., therapy) provider. If the user 105 responds with a user input indicating the assistance (e.g., therapy) provider is to be contacted, the options component 820 may invoke a provider contact component 815, which may be a two-way interface between the skill component 190a and one or more assistance (e.g., health care) provider systems. Normally, only Health Insurance Portability and Accountability Act (HIPAA) data will be exchanged between the skill component 190a and an assistance (e.g., health care) provider system via the provider contact component 915. Via the provider contact component 815, the skill component 190a may send (i.e., with advanced informed user permission), to an assistance (e.g., health care) provider system, results of the conversational assessment performed by the conversational assessment component 180, topics discussed during the conversational assessment, outcomes of check-ins of the user with the skill component 190a, and/or summaries of (e.g., mental health) activities (e.g., coping activities) the user 105 has performed using the skill component 190a. An assistance (e.g., health care) provider system may send, to the skill component 190a and via the provider contact component 815, a command to recommend the user 105 use a specific (e.g., coping) skill component, a command to configure a reminder to the user 105 (e.g., regarding medication refill and use), and/or a command to configure a check-in for the user 105.

If the user 105 is not presently receiving assistance (e.g., is not presently in therapy), or in some embodiments, the user 105 is not presently receiving assistance (e.g., therapy) for the condition the state (e.g., mental health level) assessment data identified as severe, the assistance status component 810 may cause a professional recommendation component 830 to determine one or more assistance providers, such as a therapist, psychologist, or coach, for the user 105 based on the state (e.g., mental health level) assessment output by the state (e.g., mental health level) assessment component 805, the user profile data of the user 105, and/or one or more topics discussed during the conversational assessment. The professional recommendation component 830 may store or have access to a storage of assistance (e.g., health care) provider profiles, and may query said storage for one or more providers based on factors such as geographic location of the user 105, specialization, and area of expertise (e.g., treating depression).

The profile data, of the one or more identified providers, identified by the professional recommendation component 830 may be sent to an assistance matching component 865 to further identify a provider for the user 105. The assistance matching component 865 may determine an assistance (e.g., health care) provider for the user 105 based on one or more preferences of the user 105, as represented in the user's user profile data. Example preferences may be based on, for example, gender of the assistance (e.g., health care) provider, age of the assistance (e.g., health care) provider, and geographic location of the assistance (e.g., health care) provider.

In some instances, the options component 820 may determine the user 105 should practice a coping exercise and cause a coping skill component 190b to process. In some embodiments, the user 105 may request a coping exercise in a user input aside from a conversational assessment, and the listener component 175 may call the options component 820 in response to receiving the user input. In some embodiments, the user profile data of the user 105 may include an indication that the user 105 should perform coping exercises. The coping skill component 190b may retrieve different coping exercises from a cognitive behavior therapy (CBT) storage 855. The CBT storage 855 may store different types of coping exercises that the user 105 may perform to assist with mental health therapy. The coping skill component 190b may retrieve general coping exercises from the CBT storage 855, and then may personalize the coping exercises for the user 105 based on the user profile data and state (e.g., mental health level) assessment data. In some embodiments, the functionality of the coping skill component 190b may be implemented by the skill component 190a The options component 820 may determine the user 105 would like to schedule a reminder, a routine, or check-in, such as with their assistance (e.g., health care) provider, and activate a reminder configuration component 840. The reminder configuration component 840 may provide the user 105 with an interface, such as a voice user interface or a graphical user interface, to schedule reminders, such as a reminder to check-in with an assistance (e.g., health care) provider or a medication reminder.

The reminder configuration component 840 of the skill component 190a may provide for the user 105 to schedule check-in reminders, such as with an assistance (e.g., health care) provider, a coach, or a friend, and the check-in reminder may be scheduled on a regular or random basis. The reminders may be for specific activities, such as practicing coping exercises, and for taking medication. Check-ins and reminders may be explicitly configured by either the user 105 or an assistance (e.g., health care) provider for the user 105. Additionally, check-ins and reminders may be implicitly set up or recommended by the skill component 190a based on appointment timings in an electronic calendar of the user 105, routines of the user 105, and learned user preferences.

In addition to reminding the user 105 to take medications, the reminder configuration component 840 may be configured to assist with prescription management for the user 105. The reminder configuration component 840 may be used to manage prescriptions using reminders and confirmation of medication pick up. The reminder configuration component 840 may provide refill reminders and manage prescription refills using insurance payments. In some embodiments, the reminder configuration component 840 may interface with the provider contact component 815 to alert the provider when the user 105 may require a new prescription so that the provider may contact the user 105.

The reminder configuration component 840 may assist the user 105 in scheduling and rescheduling appointments. The reminder configuration component 840 may provide appointment scheduling with assistance (e.g., health care) providers across multiple provider networks. The reminder configuration component 840 may interface with the assistance matching component 865 and provide recommendations based on price, availability, out-of-pocket cost (i.e., based on the insurance policy of the user 105 as represented in an insurance storage 850), and/or other criteria for scheduling an appointment with a provider.

The options component 820 may determine the user 105 should be offered to speak with a person, such as a therapist, coach, or crisis line counselor. The options component 820 may activate an in-person option component 825 to offer for the user 105 to speak with an assistance provider (e.g., therapist, coach, or counselor). The in-person option component 825 may access the user profile data to determine if the user 105 has provided a preference for the type of in-person contact the user 105 prefers. The in-person option component 825 may provide the user 105 with an interface, such as a voice user interface or a graphical user interface, to select the type of in-person contact they would prefer. Similar to the professional recommendation component 830, the in-person option component 825 may determine one or more assistance (e.g., health care) providers, for the user 105 based on the state (e.g., mental health level) assessment data, the user profile data, and/or topic history data associated with the 105. The in-person option component 825 may request one or more assistance (e.g., health care) provider profiles, from a database of assistance (e.g., health care) provider profiles, based on factors such as geographic location, and area of expertise (e.g., treating depression). The one or more assistance (e.g., health care) provider profiles, identified by the in-person option component 825, may be sent to the assistance matching component 865 to further identify an assistance (e.g., health care) provider for the user 105.

The assistance matching component 865 may receive assistance (e.g., health care) provider data from either the in-person option component 825 or the professional recommendation component 830. The assistance matching component 865 may prompt the user 105 for health care profiler preferences, such as gender, age, race, specialization, or geographic location. The assistance matching component 865 may narrow the assistance (e.g., health care) provider data based on the user preference(s). The assistance matching component 865 may access an insurance database 850 to identify assistance (e.g., health care) providers that are part of an insurance network for the user 105. The assistance matching component 865 may provide one or more assistance (e.g., health care) providers' contact information to the user 105. In some embodiments, the assistance matching component 865 may respond to one or more questions from the user 105 about insurance coverage and the indicated assistance (e.g., health care) provider, such as out-of-pocket costs and an estimated number of sessions that are covered by the user's insurance.

If the in-person option component 825 offers to connect the user 105 with a crisis hotline, the assistance matching component 865 may identify one or more crisis hotlines that are in the locality of the user 105 and/or one or more crisis hotlines that specialize in the user's condition (e.g., mental health condition, such as depression, anxiety, etc.). In some instances, such as if the condition is identified as severe, the assistance matching component 865 may instantly connect the user 105 with an assistance (e.g., health care) provider, such as through a 24-hour crisis hotline. The skill component 190*a* may provide the assistance (e.g., health care) provider with information (e.g., the mental health level assessment data) about the user 105, if given permission by the user 105.

Upon completing the action identified by the options component 820 (e.g., setting a reminder, identifying an assistance provider), the listener component 175 may prompt the user 105 as to whether there are additional ways the skill component 190*a* may assist the user 105, such as asking the user 105 "can I assist you with anything else?" or "was I helpful?"

Figure 9:
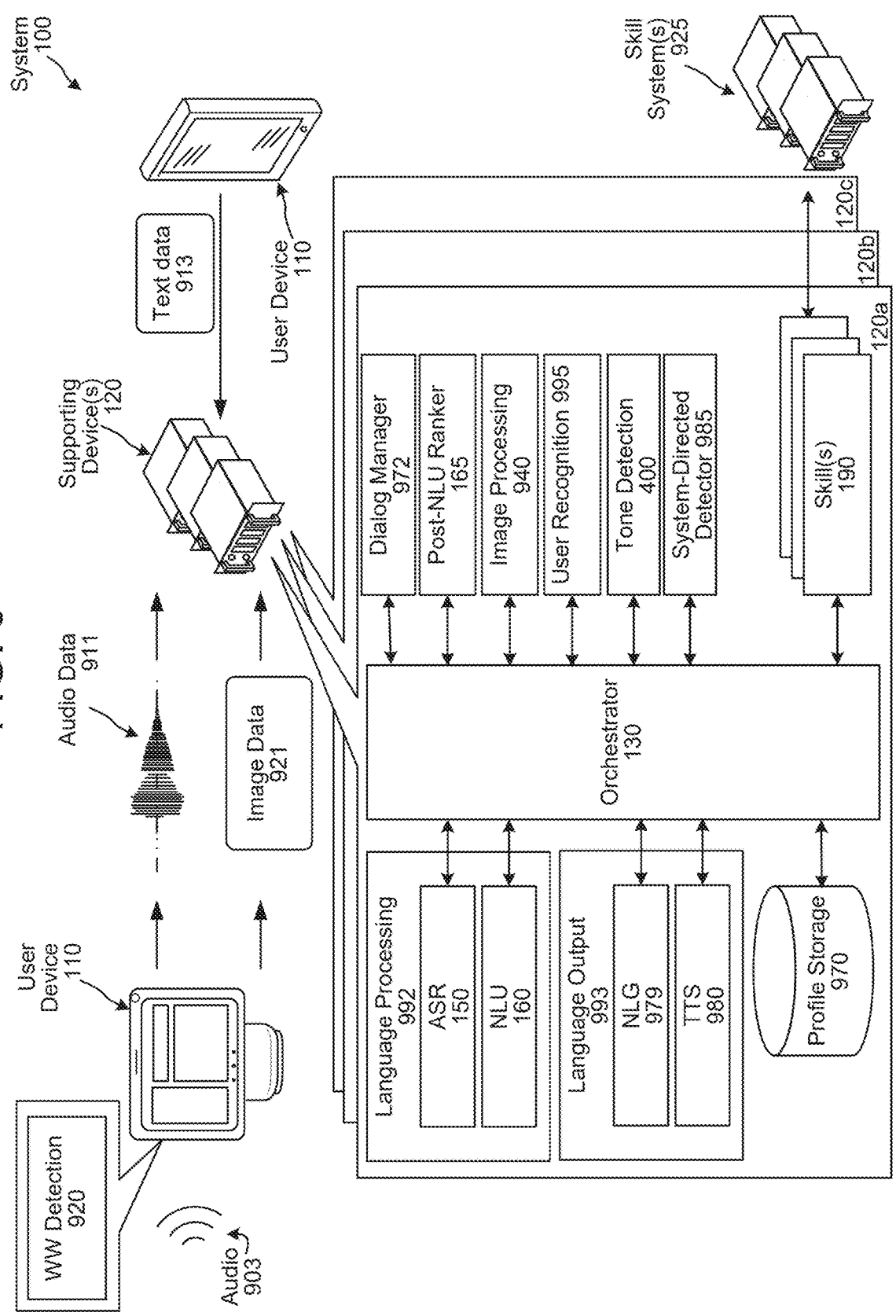
FIG. 9 is a conceptual diagram of components of the system, according to embodiments of the present disclosure.

The system 100 may operate using various components as described in FIG. 9. The various components may be located on same or different physical devices. Communication between various components may occur directly or across a network(s) 199. The user device 110 may include audio capture component(s), such as a microphone or array of microphones of a user device 110, captures audio 903 and creates corresponding audio data. Once speech is detected in audio data representing the audio 903, the user device 110 may determine if the speech is directed at the user device 110/supporting device(s) 120. In at least some embodiments, such determination may be made using a wakeword detection component 920. The wakeword detection component 920 may be configured to detect various wakewords. In at least some examples, each wakeword may correspond to a name of a different digital assistant. An example wakeword/digital assistant name is "Alexa." In another example, input to the system may be in form of text data 913, for example as a result of a user typing an input into a user interface of user device 110. Other input forms may include indication that the user has pressed a physical or virtual button on user device 110, the user has made a gesture, etc. The user device 110 may also capture images using camera(s) 1518 of the user device 110 and may send image data 921 representing those image(s) to the supporting device(s) 120. The image data 921 may include raw image data or image data processed by the user device 110 before sending to the supporting device(s) 120. The image data 921 may be used in various manners by different components of the system to perform operations such as determining whether a user is directing an utterance to the system, interpreting a user command, responding to a user command, etc.

The wakeword detector 920 of the user device 110 may process the audio data, representing the audio 903, to determine whether speech is represented therein. The user device 110 may use various techniques to determine whether the audio data includes speech. In some examples, the user device 110 may apply voice-activity detection (VAD) techniques. Such techniques may determine whether speech is present in audio data based on various quantitative aspects of the audio data, such as the spectral slope between one or more frames of the audio data; the energy levels of the audio data in one or more spectral bands; the signal-to-noise ratios of the audio data in one or more spectral bands; or other quantitative aspects. In other examples, the user device 110 may implement a classifier configured to distinguish speech from background noise. The classifier may be implemented by techniques such as linear classifiers, support vector machines, and decision trees. In still other examples, the user device 110 may apply hidden Markov model (HMM) or Gaussian mixture model (GMM) techniques to compare the audio data to one or more acoustic models in storage, which acoustic models may include models corresponding to speech, noise (e.g., environmental noise or background noise), or silence. Still other techniques may be used to determine whether speech is present in audio data.

Wakeword detection is typically performed without performing linguistic analysis, textual analysis, or semantic analysis. Instead, the audio data, representing the audio 903, is analyzed to determine if specific characteristics of the audio data match preconfigured acoustic waveforms, audio signatures, or other data corresponding to a wakeword.

Thus, the wakeword detection component 920 may compare audio data to stored data to detect a wakeword. One approach for wakeword detection applies general large vocabulary continuous speech recognition (LVCSR) systems to decode audio signals, with wakeword searching being conducted in the resulting lattices or confusion networks. Another approach for wakeword detection builds HMMs for each wakeword and non-wakeword speech signals, respectively. The non-wakeword speech includes other spoken words, background noise, etc. There can be one or more HMMs built to model the non-wakeword speech characteristics, which are named filler models. Viterbi decoding is used to search the best path in the decoding graph, and the decoding output is further processed to make the decision on wakeword presence. This approach can be extended to include discriminative information by incorporating a hybrid DNN-HMM decoding framework. In another example, the wakeword detection component 920 may be built on deep neural network (DNN)/recursive neural network (RNN) structures directly, without HMM being involved. Such an architecture may estimate the posteriors of wakewords with context data, either by stacking frames within a context window for DNN, or using RNN. Follow-on posterior threshold tuning or smoothing is applied for decision making. Other techniques for wakeword detection, such as those known in the art, may also be used.

Once the wakeword is detected by the wakeword detector 920 and/or input is detected by an input detector, the user device 110 may "wake" and begin transmitting audio data 911, representing the audio 903, to the supporting device(s) 120. The audio data 911 may include data corresponding to the wakeword; in other embodiments, the portion of the audio corresponding to the wakeword is removed by the user device 110 prior to sending the audio data 911 to the supporting device(s) 120. In the case of touch input detection or gesture based input detection, the audio data may not include a wakeword.

In some implementations, the system 100 may include more than one supporting device(s) 120. The supporting device(s) 120 may respond to different wakewords and/or perform different categories of tasks. Each supporting device(s) 120 may be associated with its own wakeword such that speaking a certain wakeword results in audio data be sent to and processed by a particular system. For example, detection of the wakeword "Alexa" by the wakeword detector 920 may result in sending audio data to supporting device(s) 120*a* for processing while detection of the wakeword "Computer" by the wakeword detector may result in sending audio data to supporting device(s) 120*b* for processing. The system may have a separate wakeword and system for different skills/systems (e.g., "Dungeon Master" for a game play skill/supporting device(s) 120*c*) and/or such skills/systems may be coordinated by one or more skill component(s) 190 of the supporting device(s) 120.

The user device 110 may also include a system-directed input detector 1185. (The supporting device(s) 120 may also include a system-directed input detector 985 which may operate in a manner similar to system-directed input detector 1185.) The system-directed input detector 1185 may be configured to determine whether an input to the system (for example speech, a gesture, etc.) is directed to the system or not directed to the system (for example directed to another user, etc.). The system-directed input detector 1185 may work in conjunction with the wakeword detector 920. If the system-directed input detector 1185 determines an input is directed to the system, the user device 110 may "wake" and begin sending captured data for further processing (for example, processing audio data using the language processing 992/1192, processing captured image data using image processing component 940/1140 or the like). If data is being processed the user device 110 may indicate such to the user, for example by activating or changing the color of an illuminated output (such as a light emitting diode (LED) ring), displaying an indicator on a display (such as a light bar across the display), outputting an audio indicator (such as a beep) or otherwise informing a user that input data is being processed. If the system-directed input detector 1185 determines an input is not directed to the system (such as a speech or gesture directed to another user) the user device 110 may discard the data and take no further action for processing purposes. In this way the system 100 may prevent processing of data not directed to the system, thus protecting user privacy. As an indicator to the user, however, the system may output an audio, visual, or other indicator when the system-directed input detector 1185 is determining whether an input is potentially device directed. For example, the system may output an orange indicator while considering an input, and may output a green indicator if a system-directed input is detected. Other such configurations are possible.

Upon receipt by the supporting device(s) 120, the audio data 911 may be sent to an orchestrator component 130. The orchestrator component 130 may include memory and logic that enables the orchestrator component 130 to transmit various pieces and forms of data to various components of the system, as well as perform other operations as described herein.

The orchestrator component 130 may send the audio data 911 to a language processing component 992. The language processing component 992 (sometimes also referred to as a spoken language understanding (SLU) component) includes an automatic speech recognition (ASR) component 150 and a natural language understanding (NLU) component 160. The ASR component 150 may transcribe the audio data 911 into text data. The text data output by the ASR component 150 represents one or more than one (e.g., in the form of an N-best list) ASR hypotheses representing speech represented in the audio data 911. The ASR component 150 interprets the speech in the audio data 911 based on a similarity between the audio data 911 and pre-established language models. For example, the ASR component 150 may compare the audio data 911 with models for sounds (e.g., acoustic units such as phonemes, senons, phones, etc.) and sequences of sounds to identify words that match the sequence of sounds of the speech represented in the audio data 911. The ASR component 150 sends the text data generated thereby to an NLU component 160, via, in some embodiments, the orchestrator component 130. The text data sent from the ASR component 150 to the NLU component 160 may include a single top-scoring ASR hypothesis or may include an N-best list including multiple top-scoring ASR hypotheses. An N-best list may additionally include a respective score associated with each ASR hypothesis represented therein. The ASR component 150 is described in greater detail below with regard to FIG. 10.

Figure 10:
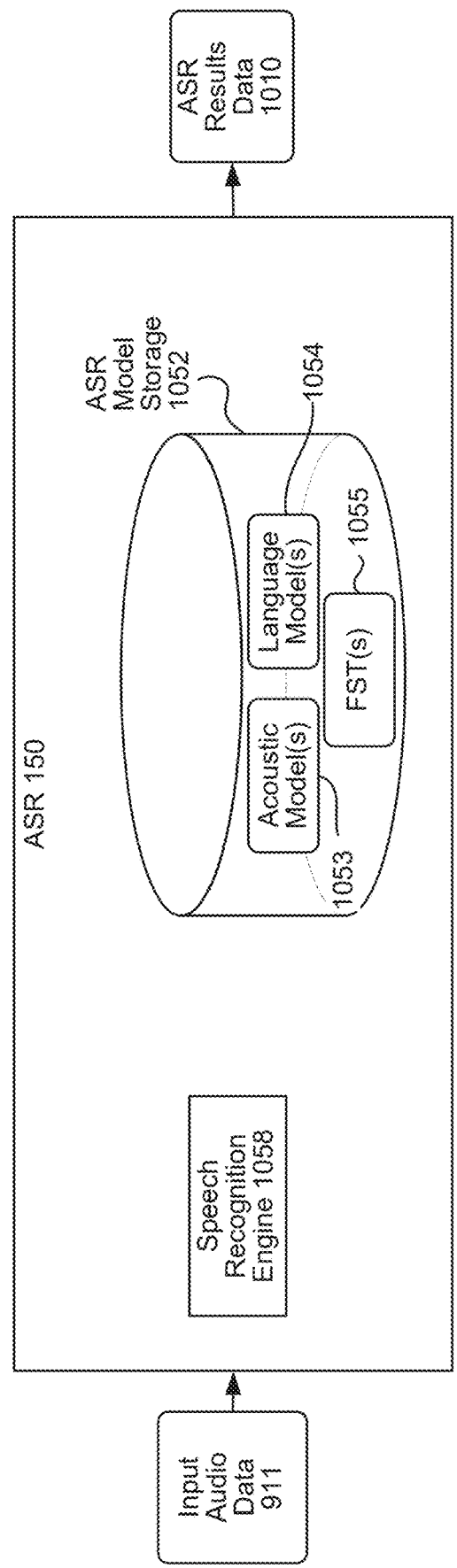
FIG. 10 is a conceptual diagram of an automatic speech recognition (ASR) component, according to embodiments of the present disclosure.

With reference to FIG. 10, the ASR component 150 may interpret a spoken natural language input based on the similarity between the spoken natural language input and pre-established language models 1054 stored in an ASR model storage 1052. For example, the ASR component 150 may compare the audio data with models for sounds (e.g., subword units or phonemes) and sequences of sounds to identify words that match the sequence of sounds spoken in the natural language input. Alternatively, the ASR component 150 may use a finite state transducer (FST) 1055 to implement the language model functions.

When the ASR component 150 generates more than one ASR hypothesis for a single spoken natural language input, each ASR hypothesis may be assigned a score (e.g., probability score, confidence score, etc.) representing a likelihood that the corresponding ASR hypothesis matches the spoken natural language input (e.g., representing a likelihood that a particular set of words matches those spoken in the natural language input). The score may be based on a number of factors including, for example, the similarity of the sound in the spoken natural language input to models for language sounds (e.g., an acoustic model 1053 stored in the ASR model storage 1052), and the likelihood that a particular word, which matches the sounds, would be included in the sentence at the specific location (e.g., using a language or grammar model 1054). Based on the considered factors and the assigned confidence score, the ASR component 150 may output an ASR hypothesis that most likely matches the spoken natural language input, or may output multiple ASR hypotheses in the form of a lattice or an N-best list, with each ASR hypothesis corresponding to a respective score.

The ASR component 150 may include a speech recognition engine 1058. The ASR component 150 receives audio data 911 (for example, received from a user device 110 having processed audio detected by a microphone by an acoustic front end (AFE) or other component). The speech recognition engine 1058 compares the audio data 911 with acoustic models 1053, language models 1054, FST(s) 1055, and/or other data models and information for recognizing the speech conveyed in the audio data. The audio data 911 may be audio data that has been digitized (for example by an AFE) into frames representing time intervals for which the AFE determines a number of values, called features, representing the qualities of the audio data, along with a set of those values, called a feature vector, representing the features/qualities of the audio data within the frame. In at least some embodiments, audio frames may be 10 ms each. Many different features may be determined, as known in the art, and each feature may represent some quality of the audio that may be useful for ASR processing. A number of approaches may be used by an AFE to process the audio data, such as mel-frequency cepstral coefficients (MFCCs), perceptual linear predictive (PLP) techniques, neural network feature vector techniques, linear discriminant analysis, semi-tied covariance matrices, or other approaches known to those of skill in the art.

The speech recognition engine 1058 may process the audio data 911 with reference to information stored in the ASR model storage 1052. Feature vectors of the audio data 911 may arrive at the supporting device(s) 120 encoded, in which case they may be decoded prior to processing by the speech recognition engine 1058.

The speech recognition engine 1058 attempts to match received feature vectors to language acoustic units (e.g., phonemes) and words as known in the stored acoustic models 1053, language models 9B54, and FST(s) 1055. For example, audio data 911 may be processed by one or more acoustic model(s) 1053 to determine acoustic unit data. The acoustic unit data may include indicators of acoustic units detected in the audio data 911 by the ASR component 150. For example, acoustic units can consist of one or more of phonemes, diaphonemes, tonemes, phones, diphones, triphones, or the like. The acoustic unit data can be represented using one or a series of symbols from a phonetic alphabet such as the X-SAMPA, the International Phonetic Alphabet, or Initial Teaching Alphabet (ITA) phonetic alphabets. In some implementations a phoneme representation of the audio data can be analyzed using an n-gram based tokenizer. An entity, or a slot representing one or more entities, can be represented by a series of n-grams.

The acoustic unit data may be processed using the language model 1054 (and/or using FST 1055) to determine ASR data 1010. The ASR data 1010 can include one or more hypotheses. One or more of the hypotheses represented in the ASR data 1010 may then be sent to further components (such as the NLU component 160) for further processing as discussed herein. The ASR data 1010 may include representations of text of an utterance, such as words, subword units, or the like.

The speech recognition engine 1058 computes scores for the feature vectors based on acoustic information and language information. The acoustic information (such as identifiers for acoustic units and/or corresponding scores) is used to calculate an acoustic score representing a likelihood that the intended sound represented by a group of feature vectors matches a language phoneme. The language information is used to adjust the acoustic score by considering what sounds and/or words are used in context with each other, thereby improving the likelihood that the ASR component 150 will output ASR hypotheses that make sense grammatically. The specific models used may be general models or may be models corresponding to a particular domain, such as music, banking, etc.

The speech recognition engine 1058 may use a number of techniques to match feature vectors to phonemes, for example using Hidden Markov Models (HMMs) to determine probabilities that feature vectors may match phonemes. Sounds received may be represented as paths between states of the HMM and multiple paths may represent multiple possible text matches for the same sound. Further techniques, such as using FSTs, may also be used.

The speech recognition engine 1058 may use the acoustic model(s) 1053 to attempt to match received audio feature vectors to words or subword acoustic units. An acoustic unit may be a senone, phoneme, phoneme in context, syllable, part of a syllable, syllable in context, or any other such portion of a word. The speech recognition engine 1058 computes recognition scores for the feature vectors based on acoustic information and language information. The acoustic information is used to calculate an acoustic score representing a likelihood that the intended sound represented by a group of feature vectors match a subword unit. The language information is used to adjust the acoustic score by considering what sounds and/or words are used in context with each other, thereby improving the likelihood that the ASR component 150 outputs ASR hypotheses that make sense grammatically.

The speech recognition engine 1058 may use a number of techniques to match feature vectors to phonemes or other acoustic units, such as diphones, triphones, etc. One common technique is using Hidden Markov Models (HMMs). HMMs are used to determine probabilities that feature vectors may match phonemes. Using HMMs, a number of states are presented, in which the states together represent a potential phoneme (or other acoustic unit, such as a triphone) and each state is associated with a model, such as a Gaussian mixture model or a deep belief network. Transitions between states may also have an associated probability, representing a likelihood that a current state may be reached from a past state. Sounds received may be represented as paths between states of the HMM and multiple paths may represent multiple possible text matches for the same sound. Each phoneme may be represented by multiple potential states corresponding to different known pronunciations of the phonemes and their parts (such as the beginning, middle, and end of a spoken language sound). An initial determination of a probability of a potential phoneme may be associated with one state. As new feature vectors are processed by the speech recognition engine 1058, the state may change or stay the same, based on the processing of the new feature vectors. A Viterbi algorithm may be used to find the most likely sequence of states based on the processed feature vectors.

The probable phonemes and related states/state transitions, for example HMM states, may be formed into paths traversing a lattice of potential phonemes. Each path represents a progression of phonemes that potentially match the audio data represented by the feature vectors. One path may overlap with one or more other paths depending on the recognition scores calculated for each phoneme. Certain probabilities are associated with each transition from state to state. A cumulative path score may also be calculated for each path. This process of determining scores based on the feature vectors may be called acoustic modeling. When combining scores as part of the ASR processing, scores may be multiplied together (or combined in other ways) to reach a desired combined score or probabilities may be converted to the log domain and added to assist processing.

The speech recognition engine 1058 may also compute scores of branches of the paths based on language models or grammars. Language modeling involves determining scores for what words are likely to be used together to form coherent words and sentences. Application of a language model may improve the likelihood that the ASR component 150 correctly interprets the speech contained in the audio data. For example, for an input audio sounding like "hello," acoustic model processing that returns the potential phoneme paths of "H E L O", "H A L O", and "Y E L O" may be adjusted by a language model to adjust the recognition scores of "H E L O" (interpreted as the word "hello"), "H A L O" (interpreted as the word "halo"), and "Y E L O" (interpreted as the word "yellow") based on the language context of each word within the spoken utterance.

The speech processing system 992 may further include a NLU component 160. The NLU component 160 may receive the text data from the ASR component. The NLU component 160 may attempts to make a semantic interpretation of the phrase(s) or statement(s) represented in the text data input therein by determining one or more meanings associated with the phrase(s) or statement(s) represented in the text data. The NLU component 160 may determine an intent representing an action that a user desires be performed and may determine information that allows a device (e.g., the user device 110, the supporting device(s) 120, a skill component 190, a skill system(s) 925, etc.) to execute the intent. For example, if the text data corresponds to "play the 5th Symphony by Beethoven," the NLU component 160 may determine an intent that the system output music and may identify "Beethoven" as an artist/composer and "5th Symphony" as the piece of music to be played. For further example, if the text data corresponds to "what is the weather," the NLU component 160 may determine an intent that the system output weather information associated with a geographic location of the user device 110. In another example, if the text data corresponds to "turn off the lights," the NLU component 160 may determine an intent that the system turn off lights associated with the user device 110 or the user 5. However, if the NLU component 160 is unable to resolve the entity—for example, because the entity is referred to by anaphora such as "this song" or "my next appointment"—the speech processing system 992 can send a decode request to another speech processing system 992 for information regarding the entity mention and/or other context related to the utterance. The speech processing system 992 may augment, correct, or base results data upon the audio data 911 as well as any data received from the other speech processing system 992.

The NLU component 160 may return NLU results data (which may include tagged text data, indicators of intent, etc.) back to the orchestrator component 130. The orchestrator component 130 may forward the NLU results data to a skill component(s) 190. If the NLU results data includes a single NLU hypothesis, the NLU component 160 and the orchestrator component 130 may direct the NLU results data to the skill component(s) 190 associated with the NLU hypothesis. If the NLU results data includes an N-best list of NLU hypotheses, the NLU component 160 and the orchestrator component 130 may direct the top scoring NLU hypothesis to a skill component(s) 190 associated with the top scoring NLU hypothesis. The system may also include a post-NLU ranker 965 which may incorporate other information to rank potential interpretations determined by the NLU component 160. The user device 110 may also include its own post-NLU ranker 1165, which may operate similarly to the post-NLU ranker 965.

A skill component may be software running on the supporting device(s) 120 that is akin to a software application. That is, a skill component 190 may enable the supporting device(s) 120 to execute specific functionality in order to provide data or produce some other requested output. As used herein, a "skill component" may refer to software that may be placed on a machine or a virtual machine (e.g., software that may be launched in a virtual instance when called). A skill component may be software customized to perform one or more actions as indicated by a business entity, device manufacturer, user, etc. What is described herein as a skill component may be referred to using many different terms, such as an action, bot, app, application, or the like. The supporting device(s) 120 may be configured with more than one skill component 190. For example, a weather service skill component may enable the supporting device(s) 120 to provide weather information, a car service skill component may enable the supporting device(s) 120 to book a trip with respect to a taxi or ride sharing service, a restaurant skill component may enable the supporting device(s) 120 to order a pizza with respect to the restaurant's online ordering system, etc. A skill component 190 may operate in conjunction between the supporting device(s) 120 and other devices, such as the user device 110, in order to complete certain functions. Inputs to a skill component 190 may come from speech processing interactions or through other interactions or input sources. A skill component 190 may include hardware, software, firmware, or the like that may be dedicated to a particular skill component 190 or shared among different skill components 190.

A skill support system(s) 925 may communicate with a skill component(s) 190 within the supporting device(s) 120 and/or directly with the orchestrator component 130 or with other components. A skill support system(s) 925 may be configured to perform one or more actions. An ability to perform such action(s) may sometimes be referred to as a "skill." That is, a skill may enable a skill support system(s) 925 to execute specific functionality in order to provide data or perform some other action requested by a user. For example, a weather service skill may enable a skill support system(s) 925 to provide weather information to the supporting device(s) 120, a car service skill may enable a skill support system(s) 925 to book a trip with respect to a taxi or ride sharing service, an order pizza skill may enable a skill support system(s) 925 to order a pizza with respect to a restaurant's online ordering system, etc. Additional types of skills include home automation skills (e.g., skills that enable a user to control home devices such as lights, door locks, cameras, thermostats, etc.), entertainment device skills (e.g., skills that enable a user to control entertainment devices such as smart televisions), video skills, flash briefing skills, as well as custom skills that are not associated with any pre-configured type of skill.

The supporting device(s) 120 may be configured with a skill component 190 dedicated to interacting with the skill support system(s) 925. Unless expressly stated otherwise, reference to a skill, skill device, or skill component may include a skill component 190 operated by the supporting device(s) 120 and/or skill operated by the skill support system(s) 925. Moreover, the functionality described herein as a skill or skill may be referred to using many different terms, such as an action, bot, app, or the like. The skill component 190 and or skill support system(s) 925 may return output data to the orchestrator component 130.

Dialog processing is a field of computer science that involves communication between a computing system and a human via text, audio, and/or other forms of communication. While some dialog processing involves only simple generation of a response given only a most recent input from a user (i.e., single-turn dialog), more complicated dialog processing involves determining and optionally acting on one or more goals expressed by the user over multiple turns of dialog, such as making a restaurant reservation and/or booking an airline ticket. These multi-turn "goal-oriented" dialog systems typically need to recognize, retain, and use information collected during more than one input during a back-and-forth or "multi-turn" interaction with the user.

The supporting device(s) 120 may include a dialog manager component 972 that manages and/or tracks a dialog between a user and a device. As used herein, a "dialog" may refer to data transmissions (such as relating to multiple user inputs and system 100 outputs) between the system 100 and a user (e.g., through one or more user devices) that all relate to a single "conversation" between the system and the user that may have originated with a single user input initiating the dialog. Thus, the data transmissions of a dialog may be associated with a same dialog identifier, which may be used by components of the system 100 to track information across the dialog. Subsequent user inputs of the same dialog may or may not start with speaking of a wakeword. Each natural language input of a dialog may be associated with a different natural language input identifier such that multiple natural language input identifiers may be associated with a single dialog identifier. Further, other non-natural language inputs (e.g., image data, gestures, button presses, etc.) may relate to a particular dialog depending on the context of the inputs. For example, a user may open a dialog with the system 100 to request a food delivery in a spoken utterance and the system may respond by displaying images of food available for order and the user may speak a response (e.g., "item 1" or "that one") or may gesture a response (e.g., point to an item on the screen or give a thumbs-up) or may touch the screen on the desired item to be selected. Non-speech inputs (e.g., gestures, screen touches, etc.) may be part of the dialog and the data associated therewith may be associated with the dialog identifier of the dialog.

The dialog manager component 972 may associate a dialog identifier with the dialog upon identifying that the user is engaging in a dialog with the user. The dialog manager component 972 may track a user input and the corresponding system generated response to the user input as a turn. The dialog identifier may correspond to multiple turns of user input and corresponding system generated response. The dialog manager component 972 may transmit data identified by the dialog identifier directly to the orchestrator component 130 or other component. Depending on system configuration the dialog manager 972 may determine the appropriate system generated response to give to a particular utterance or user input of a turn. Or creation of the system generated response may be managed by another component of the system (e.g., the language output component 993, NLG 979, orchestrator component 130, etc.) while the dialog manager 972 selects the appropriate responses. Alternatively, another component of the supporting device (s) 120 may select responses using techniques discussed herein. The text of a system generated response may be sent to a TTS component 980 for creation of audio data corresponding to the response. The audio data may then be sent to a user device (e.g., user device 110) for ultimate output to the user. Alternatively (or in addition) a dialog response may be returned in text or some other form.

The dialog manager 972 may receive the ASR hypothesis/hypotheses (i.e., text data) and make a semantic interpretation of the phrase(s) or statement(s) represented therein. That is, the dialog manager 972 determines one or more meanings associated with the phrase(s) or statement(s) represented in the text data based on words represented in the text data. The dialog manager 972 determines a goal corresponding to an action that a user desires be performed as well as pieces of the text data that allow a device (e.g., the user device 110, the supporting device(s) 120, a skill component 190, a skill system(s) 925, etc.) to execute the intent. If, for example, the text data corresponds to "what is the weather," the dialog manager 972 may determine that that the supporting device(s) 120 is to output weather information associated with a geographic location of the user device 110. In another example, if the text data corresponds to "turn off the lights," the dialog manager 972 may determine that the supporting device(s) 120 is to turn off lights associated with the user device 110 or the user 105.

The dialog manager 972 may send the results data to one or more skill component(s) 190. If the results data includes a single hypothesis, the orchestrator component 130 may send the results data to the skill component(s) 190 associated with the hypothesis. If the results data includes an N-best list of hypotheses, the orchestrator component 130 may send the top scoring hypothesis to a skill component(s) 190 associated with the top scoring hypothesis.

In some embodiments, the dialog manager X may track a dialog and invoke the skill component 190*a* (e.g., as being the in-focus skill component) during the dialog.

The supporting device(s) 120 includes a language output component 993. The language output component 993 includes a natural language generation (NLG) component 979 and a text-to-speech (TTS) component 980. The NLG component 979 can generate text for purposes of TTS output to a user. For example the NLG component 979 may generate text corresponding to instructions corresponding to a particular action for the user to perform. The NLG component 979 may generate appropriate text for various outputs as described herein. The NLG component 979 may include one or more trained models configured to output text appropriate for a particular input. The text output by the NLG component 979 may become input for the TTS component 980 (e.g., output text data 1410 discussed below). Alternatively or in addition, the TTS component 980 may receive text data from a skill component 190 or other system component for output.

The NLG component 979 may include a trained model. The NLG component 979 generates text data 1410 from dialog data received by the dialog manager 972 such that the output text data 1410 has a natural feel and, in some embodiments, includes words and/or phrases specifically formatted for a requesting individual. The NLG may use templates to formulate responses. And/or the NLG system may include models trained from the various templates for forming the output text data 1410. For example, the NLG system may analyze transcripts of local news programs, television shows, sporting events, or any other media program to obtain common components of a relevant language and/or region. As one illustrative example, the NLG system may analyze a transcription of a regional sports program to determine commonly used words or phrases for describing scores or other sporting news for a particular region. The NLG may further receive, as inputs, a dialog history, an indicator of a level of formality, and/or a command history or other user history such as the dialog history.

The NLG system may generate dialog data based on one or more response templates. Further continuing the example above, the NLG system may select a template in response to the question, "What is the weather currently like?" of the form: "The weather currently is $weather_information$." The NLG system may analyze the logical form of the template to produce one or more textual responses including markups and annotations to familiarize the response that is generated. In some embodiments, the NLG system may determine which response is the most appropriate response to be selected. The selection may, therefore, be based on past responses, past questions, a level of formality, and/or any other feature, or any other combination thereof. Responsive audio data representing the response generated by the NLG system may then be generated using the text-to-speech component 980.

The TTS component 980 may generate audio data (e.g., synthesized speech) from text data using one or more different methods. Text data input to the TTS component 980 may come from a skill component 190, the orchestrator component 130, or another component of the system. In one method of synthesis called unit selection, the TTS component 980 matches text data against a database of recorded speech. The TTS component 980 selects matching units of recorded speech and concatenates the units together to form audio data. In another method of synthesis called parametric synthesis, the TTS component 980 varies parameters such as frequency, volume, and noise to create audio data including an artificial speech waveform. Parametric synthesis uses a computerized voice generator, sometimes called a vocoder.

The user device 110 may include still image and/or video capture components such as a camera or cameras to capture one or more images. The user device 110 may include circuitry for digitizing the images and/or video for transmission to the supporting device(s) 120 as image data. The user device 110 may further include circuitry for voice command-based control of the camera, allowing a user 105 to request capture of image or video data. The user device 110 may process the commands locally or send audio data 911 representing the commands to the supporting device(s) 120 for processing, after which the supporting device(s) 120 may return output data that can cause the user device 110 to engage its camera.

Upon receipt by the supporting device(s) 120, the image data 921 may be sent to an orchestrator component 130. The orchestrator component 130 may send the image data 921 to an image processing component 940. The image processing component 940 can perform computer vision functions such as object recognition, modeling, reconstruction, etc. For example, the image processing component 940 may detect a person, face, etc. (which may then be identified using user recognition component 995). The device may also include an image processing component 1140 which operates similarly to image processing component 940.

In some implementations, the image processing component 940 can detect the presence of text in an image. In such implementations, the image processing component 940 can recognize the presence of text, convert the image data to text data, and send the resulting text data via the orchestrator component 130 to the language processing component 992 for processing by the NLU component 160.

Figure 12:
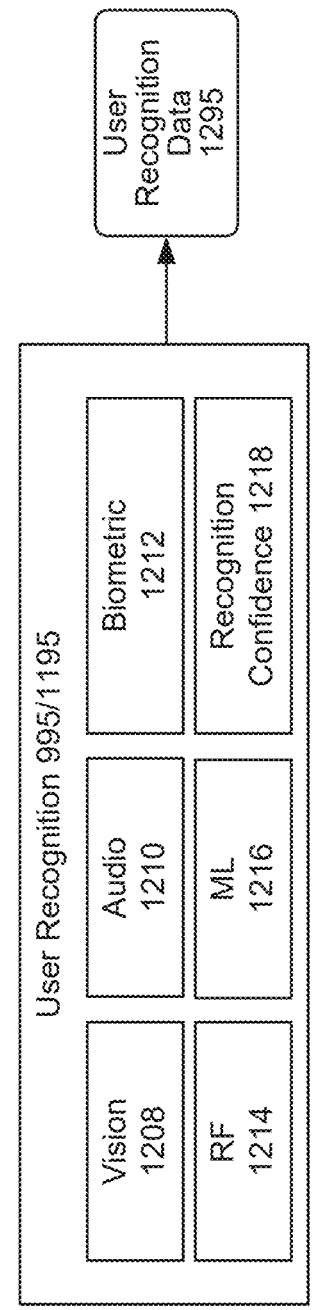
FIG. 12 is a schematic diagram of an illustrative architecture in which sensor data is combined to recognize one or more users, according to embodiments of the present disclosure.

The supporting device(s) 120 may include a user recognition component 995 that recognizes one or more users using a variety of data, as described in greater detail below with regard to FIGS. 12-13. However, the disclosure is not limited thereto, and the user device 110 may include a user recognition component 1195 instead of and/or in addition to user recognition component 995 of the supporting device(s) 120 without departing from the disclosure. User recognition component 1195 operates similarly to user recognition component 995.

The user-recognition component 995 may take as input the audio data 911 and/or text data output by the ASR component 150. The user-recognition component 995 may perform user recognition by comparing audio characteristics in the audio data 911 to stored audio characteristics of users. The user-recognition component 995 may also perform user recognition by comparing biometric data (e.g., fingerprint data, iris data, etc.), received by the system in correlation with the present user input, to stored biometric data of users assuming user permission and past authorization. The user-recognition component 995 may further perform user recognition by comparing image data (e.g., including a representation of at least a feature of a user), received by the system in correlation with the present user input, with stored image data including representations of features of different users. The user-recognition component 995 may perform additional user recognition processes, including those known in the art.

The user-recognition component 995 determines scores indicating whether user input originated from a particular user. For example, a first score may indicate a likelihood that the user input originated from a first user, a second score may indicate a likelihood that the user input originated from a second user, etc. The user-recognition component 995 also determines an overall confidence regarding the accuracy of user recognition operations.

Output of the user-recognition component 995 may include a single user identifier corresponding to the most likely user that originated the user input. Alternatively, output of the user-recognition component 995 may include an N-best list of user identifiers with respective scores indicating likelihoods of respective users originating the user input. The output of the user-recognition component 995 may be used to inform NLU processing as well as processing performed by other components of the system.

The system 100 (either on user device 110, supporting device(s) 120, or a combination thereof) may include profile storage for storing a variety of information related to individual users, groups of users, devices, etc. that interact with the system. As used herein, a "profile" refers to a set of data associated with a user, group of users, device, etc. The data of a profile may include preferences specific to the user, device, etc.; input and output capabilities of the device; internet connectivity information; user bibliographic information; subscription information, as well as other information.

The profile storage 970 may include one or more user profiles, with each user profile being associated with a different user identifier/user profile identifier. Each user profile may include various user identifying data. Each user profile may also include data corresponding to preferences of the user. Each user profile may also include preferences of the user and/or one or more device identifiers, representing one or more devices of the user. For instance, the user account may include one or more IP addresses, MAC addresses, and/or device identifiers, such as a serial number, of each additional electronic device associated with the identified user account. When a user logs into to an application installed on a user device 110, the user profile (associated with the presented login information) may be updated to include information about the user device 110, for example with an indication that the device is currently in use. Each user profile may include identifiers of skills that the user has enabled. When a user enables a skill component, the user is providing the supporting device(s) 120 with permission to allow the skill component to execute with respect to the user's natural language user inputs. If a user does not enable a skill component, the supporting device(s) 120 may not invoke the skill to execute with respect to the user's natural language user inputs.

The profile storage 970 may include one or more group profiles. Each group profile may be associated with a different group identifier. A group profile may be specific to a group of users. That is, a group profile may be associated with two or more individual user profiles. For example, a group profile may be a household profile that is associated with user profiles associated with multiple users of a single household. A group profile may include preferences shared by all the user profiles associated therewith. Each user profile associated with a group profile may additionally include preferences specific to the user associated therewith. That is, each user profile may include preferences unique from one or more other user profiles associated with the same group profile. A user profile may be a stand-alone profile or may be associated with a group profile.

The profile storage 970 may include one or more device profiles. Each device profile may be associated with a different device identifier. Each device profile may include various device identifying information. Each device profile may also include one or more user identifiers, representing one or more users associated with the device. For example, a household device's profile may include the user identifiers of users of the household.

The supporting device(s) 120 may also include a tone detection component 400 that may be configured to detect a tone of a user from audio data representing speech/utterances from the user, image data representing an image of the user, and/or the like as described in greater detail below with regard to FIG. 4. The tone detection component 400 may be included in supporting device(s) 120, as illustrated in FIG. 9, although the disclosure is not limited thereto and the tone detection component 400 may be included in other components without departing from the disclosure. For example the tone detection component 1175 may be included in the user device 110, as a separate component, etc. Tone detection component 1175 may operate similarly to tone detection component 400. The supporting device(s) 120 may use the tone detection component 400 to, for example, customize a response for a user based on an indication that the user is happy or frustrated.

Figure 11:
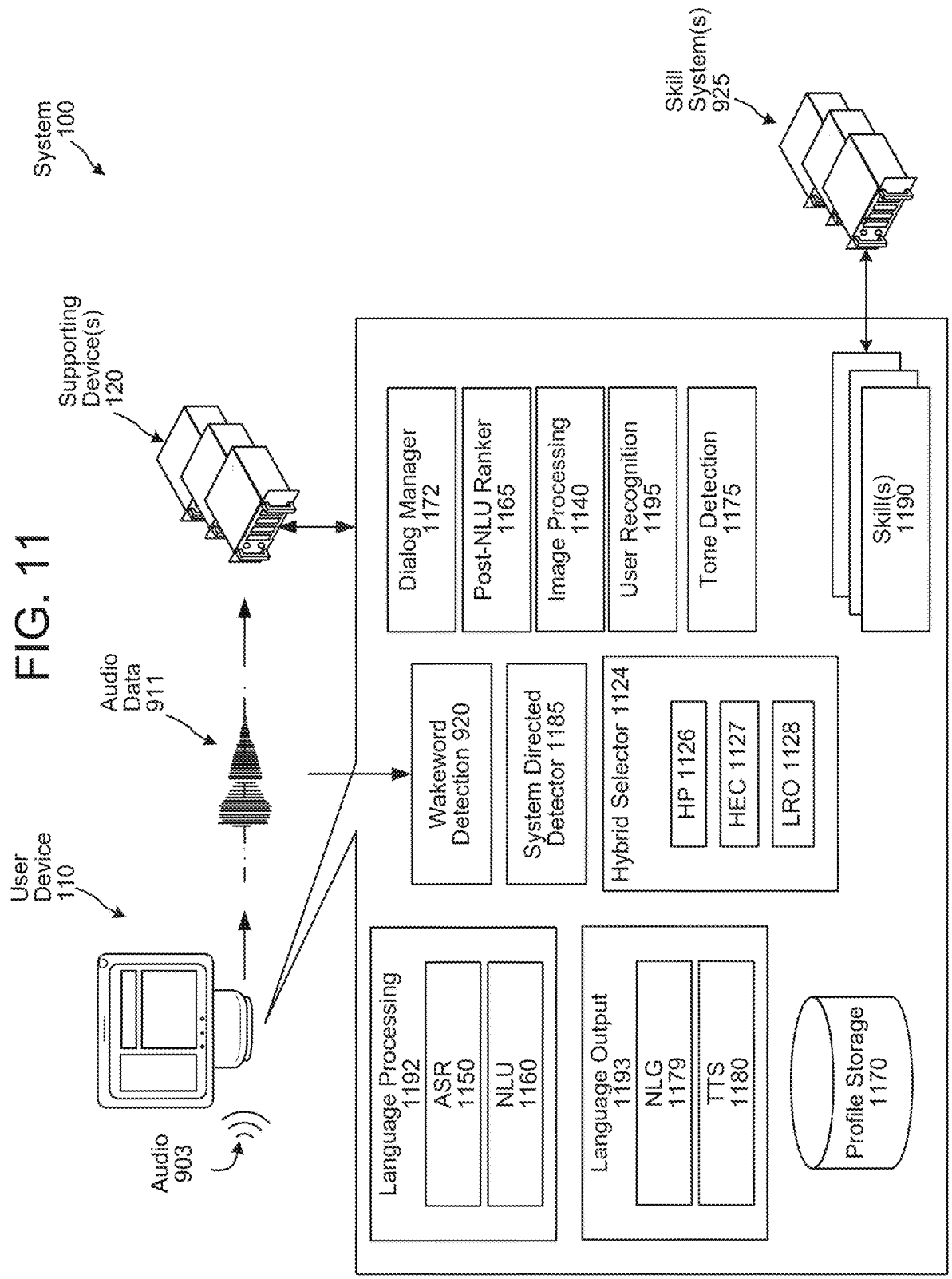
FIG. 11 is a conceptual diagram of components that may be included in a user device, according to embodiments of the present disclosure.

Although the components of FIG. 9 may be illustrated as part of supporting device(s) 120, user device 110, or otherwise, the components may be arranged in other device(s) (such as in user device 110 if illustrated in supporting device(s) 120 or vice-versa, or in other device(s) altogether) without departing from the disclosure. FIG. 11 illustrates such a user device 110.

In at least some embodiments, the supporting device(s) 120 may receive the audio data 911 from the user device 110, to recognize speech corresponding to a spoken input in the received audio data 911, and to perform functions in response to the recognized speech. In at least some embodiments, these functions involve sending directives (e.g., commands), from the supporting device(s) 120 to the user device 110 (and/or other devices) to cause the user device 110 to perform an action, such as output an audible response to the spoken input via a loudspeaker(s), and/or control secondary devices in the environment by sending a control command to the secondary devices.

Thus, when the user device 110 is able to communicate with the supporting device(s) 120 over the network(s) 199, some or all of the functions capable of being performed by the supporting device(s) 120 may be performed by sending one or more directives over the network(s) 199 to the user device 110, which, in turn, may process the directive(s) and perform one or more corresponding actions. For example, the supporting device(s) 120, using a remote directive that is included in response data (e.g., a remote response), may instruct the user device 110 to output an audible response (e.g., using TTS processing performed by an on-device TTS component 1180) to a user's question via a loudspeaker(s) of (or otherwise associated with) the user device 110, to output content (e.g., music) via the loudspeaker(s) of (or otherwise associated with) the user device 110, to display content on a display of (or otherwise associated with) the user device 110, and/or to send a directive to a secondary device (e.g., a directive to turn on a smart light). It is to be appreciated that the supporting device(s) 120 may be configured to provide other functions in addition to those discussed herein, such as, without limitation, providing step-by-step directions for navigating from an origin location to a destination location, conducting an electronic commerce transaction on behalf of the user 105 as part of a shopping function, establishing a communication session (e.g., a video call) between the user 105 and another user, and so on.

As noted with respect to FIG. 9, the user device 110 may include a wakeword detection component 920 configured to compare the audio data 911 to stored models used to detect a wakeword (e.g., "Alexa") that indicates to the user device 110 that the audio data 911 is to be processed for determining NLU results data (e.g., slot data that corresponds to a named entity, label data, and/or intent data, etc.). In at least some embodiments, a hybrid selector 1124, of the user device 110, may send the audio data 911 to the wakeword detection component 920. If the wakeword detection component 920 detects a wakeword in the audio data 911, the wakeword detection component 920 may send an indication of such detection to the hybrid selector 1124. In response to receiving the indication, the hybrid selector 1124 may send the audio data 911 to the supporting device(s) 120 and/or the ASR component 1150. The wakeword detection component 920 may also send an indication, to the hybrid selector 1124, representing a wakeword was not detected. In response to receiving such an indication, the hybrid selector 1124 may refrain from sending the audio data 911 to the supporting device(s) 120, and may prevent the ASR component 1150 from further processing the audio data 911. In this situation, the audio data 911 can be discarded.

The user device 110 may conduct its own speech processing using on-device language processing components, such as an SLU/language processing component 1192 (which may include an ASR component 1150 and an NLU 1160), similar to the manner discussed herein with respect to the SLU component 992 (or ASR component 150 and the NLU component 160) of the supporting device(s) 120. Language processing component 1192 may operate similarly to language processing component 992, ASR component 1150 may operate similarly to ASR component 150 and NLU component 1160 may operate similarly to NLU component 160. The user device 110 may also internally include, or otherwise have access to, other components such as one or more skill components 1190 capable of executing commands based on NLU results data or other results determined by the user device 110/supporting device(s) 120 (which may operate similarly to skill components 190), a user recognition component 1195 (configured to process in a similar manner to that discussed herein with respect to the user recognition component 995 of the supporting device(s) 120), profile storage 1170 (configured to store similar profile data to that discussed herein with respect to the profile storage 970 of the supporting device(s) 120), or other components. In at least some embodiments, the profile storage 1170 may only store profile data for a user or group of users specifically associated with the user device 110. Similar to as described above with respect to skill component 190, a skill component 1190 may communicate with a skill system(s) 925. The user device 110 may also have its own language output component 1193 which may include NLG component 1179 and TTS component 1180. Language output component 1193 may operate similarly to language processing component 993, NLG component 1179 may operate similarly to NLG component 979 and TTS component 1180 may operate similarly to TTS component 980.

In at least some embodiments, the on-device language processing components may not have the same capabilities as the language processing components of the supporting device(s) 120. For example, the on-device language processing components may be configured to handle only a subset of the natural language user inputs that may be handled by the supporting device(s) 120. For example, such subset of natural language user inputs may correspond to local-type natural language user inputs, such as those controlling devices or components associated with a user's home. In such circumstances the on-device language processing components may be able to more quickly interpret and respond to a local-type natural language user input, for example, than processing that involves the supporting device(s) 120. If the user device 110 attempts to process a natural language user input for which the on-device language processing components are not necessarily best suited, the language processing results determined by the user device 110 may indicate a low confidence or other metric indicating that the processing by the user device 110 may not be as accurate as the processing done by the supporting device(s) 120.

The hybrid selector 1124, of the user device 110, may include a hybrid proxy (HP) 1126 configured to proxy traffic to/from the supporting device(s) 120. For example, the HP 1126 may be configured to send messages to/from a hybrid execution controller (HEC) 1127 of the hybrid selector 1124. For example, command/directive data received from the supporting device(s) 120 can be sent to the HEC 1127 using the HP 1126. The HP 1126 may also be configured to allow the audio data 911 to pass to the supporting device(s) 120 while also receiving (e.g., intercepting) this audio data 911 and sending the audio data 911 to the HEC 1127.

In at least some embodiments, the hybrid selector 1124 may further include a local request orchestrator (LRO) 1128 configured to notify the ASR component 1150 about the availability of new audio data 911 that represents user speech, and to otherwise initiate the operations of local language processing when new audio data 911 becomes available. In general, the hybrid selector 1124 may control execution of local language processing, such as by sending "execute" and "terminate" events/instructions. An "execute" event may instruct a component to continue any suspended execution (e.g., by instructing the component to execute on a pastly-determined intent in order to determine a directive). Meanwhile, a "terminate" event may instruct a component to terminate further execution, such as when the user device 110 receives directive data from the supporting device(s) 120 and chooses to use that remotely-determined directive data.

Thus, when the audio data 911 is received, the HP 1126 may allow the audio data 911 to pass through to the supporting device(s) 120 and the HP 1126 may also input the audio data 911 to the on-device ASR component 1150 by routing the audio data 911 through the HEC 1127 of the hybrid selector 1124, whereby the LRO 1128 notifies the ASR component 1150 of the audio data 911. At this point, the hybrid selector 1124 may wait for response data from either or both of the supporting device(s) 120 or the local language processing components. However, the disclosure is not limited thereto, and in some examples the hybrid selector 1124 may send the audio data 911 only to the local ASR component 1150 without departing from the disclosure. For example, the user device 110 may process the audio data 911 locally without sending the audio data 911 to the supporting device(s) 120.

The local ASR component 1150 is configured to receive the audio data 911 from the hybrid selector 1124, and to recognize speech in the audio data 911, and the local NLU component 1160 is configured to determine a user intent from the recognized speech, and to determine how to act on the user intent by generating NLU results data which may include directive data (e.g., instructing a component to perform an action). Such NLU results data may take a form similar to that as determined by the NLU component 160 of the supporting device(s) 120. In some cases, a directive may include a description of the intent (e.g., an intent to turn off {device A}). In some cases, a directive may include (e.g., encode) an identifier of a second device(s), such as kitchen lights, and an operation to be performed at the second device(s). Directive data may be formatted using Java, such as JavaScript syntax, or JavaScript-based syntax. This may include formatting the directive using JSON. In at least some embodiments, a device-determined directive may be serialized, much like how remotely-determined directives may be serialized for transmission in data packets over the network(s) 199. In at least some embodiments, a device-determined directive may be formatted as a programmatic application programming interface (API) call with a same logical operation as a remotely-determined directive. In other words, a device-determined directive may mimic a remotely-determined directive by using a same, or a similar, format as the remotely-determined directive.

An NLU hypothesis (output by the NLU component 1160) may be selected as usable to respond to a natural language user input, and local response data may be sent (e.g., local NLU results data, local knowledge base information, internet search results, and/or local directive data) to the hybrid selector 1124, such as a "ReadyToExecute" response. The hybrid selector 1124 may then determine whether to use directive data from the on-device components to respond to the natural language user input, to use directive data received from the supporting device(s) 120, assuming a remote response is even received (e.g., when the user device 110 is able to access the supporting device(s) 120 over the network(s) 199), or to determine output audio requesting additional information from the user 105.

The user device 110 and/or the supporting device(s) 120 may associate a unique identifier with each natural language user input. The user device 110 may include the unique identifier when sending the audio data 911 to the supporting device(s) 120, and the response data from the supporting device(s) 120 may include the unique identifier to identify which natural language user input the response data corresponds.

In at least some embodiments, the user device 110 may include, or be configured to use, one or more skill components 1190 that may work similarly to the skill component(s) 190 implemented by the supporting device(s) 120. The skill component(s) 1190 may correspond to one or more domains that are used in order to determine how to act on a spoken input in a particular way, such as by outputting a directive that corresponds to the determined intent, and which can be processed to implement the desired operation. The skill component(s) 1190 installed on the user device 110 may include, without limitation, a smart home skill component (or smart home domain) and/or a device control skill component (or device control domain) to execute in response to spoken inputs corresponding to an intent to control a second device(s) in an environment, a music skill component (or music domain) to execute in response to spoken inputs corresponding to a intent to play music, a navigation skill component (or a navigation domain) to execute in response to spoken input corresponding to an intent to get directions, a shopping skill component (or shopping domain) to execute in response to spoken inputs corresponding to an intent to buy an item from an electronic marketplace, and/or the like.

Additionally or alternatively, the user device 110 may be in communication with one or more skill systems 925. For example, a skill system 925 may be located in a remote environment (e.g., separate location) such that the user device 110 may only communicate with the skill system 925 via the network(s) 199. However, the disclosure is not limited thereto. For example, in at least some embodiments, a skill system 925 may be configured in a local environment (e.g., home server and/or the like) such that the user device 110 may communicate with the skill system 925 via a private network, such as a local area network (LAN).

As used herein, a "skill" may refer to a skill component 1190, a skill system 925, or a combination of a skill component 1190 and a corresponding skill system 925. Similar to the manner discussed with regard to FIG. 9, the user device 110 may be configured to recognize multiple different wakewords and/or perform different categories of tasks depending on the wakeword. Such different wakewords may invoke different processing components of user device 110 (not illustrated in FIG. 11). For example, detection of the wakeword "Alexa" by the wakeword detector 920 may result in sending audio data to certain language processing components 1192/skills 1190 for processing while detection of the wakeword "Computer" by the wakeword detector may result in sending audio data different language processing components 1192/skills 1190 for processing.

The user device 110 and/or the supporting device(s) 120 may include a user recognition component 995 that recognizes one or more users using a variety of data. As illustrated in FIG. 12, the user recognition component 995 may include one or more subcomponents including a vision component 1208, an audio component 1210, a biometric component 1212, a radio frequency (RF) component 1214, a machine learning (ML) component 1216, and a recognition confidence component 1218. In some instances, the user recognition component 995 may monitor data and determinations from one or more subcomponents to determine an identity of one or more users associated with data input to the user device 110 and/or the supporting device(s) 120. The user recognition component 995 may output user recognition data 1295, which may include a user identifier associated with a user the user recognition component 995 determines originated data input to the user device 110 and/or the supporting device(s) 120. The user recognition data 1295 may be used to inform processes performed by various components of the user device 110 and/or the supporting device(s) 120.

The vision component 1208 may receive data from one or more sensors capable of providing images (e.g., cameras) or sensors indicating motion (e.g., motion sensors). The vision component 1208 can perform facial recognition or image analysis to determine an identity of a user and to associate that identity with a user profile associated with the user. In some instances, when a user is facing a camera, the vision component 1208 may perform facial recognition and identify the user with a high degree of confidence. In other instances, the vision component 1208 may have a low degree of confidence of an identity of a user, and the user recognition component 995 may utilize determinations from additional components to determine an identity of a user. The vision component 1208 can be used in conjunction with other components to determine an identity of a user. For example, the user recognition component 995 may use data from the vision component 1208 with data from the audio component 1210 to identify what user's face appears to be speaking at the same time audio is captured by a user device 110 the user is facing for purposes of identifying a user who spoke an input to the user device 110 and/or the supporting device(s) 120.

The system of the present disclosure may include biometric sensors that transmit data to the biometric component 1212. For example, the biometric component 1212 may receive data corresponding to fingerprints, iris or retina scans, thermal scans, weights of users, a size of a user, pressure (e.g., within floor sensors), etc., and may determine a biometric profile corresponding to a user. The biometric component 1212 may distinguish between a user and sound from a television, for example. Thus, the biometric component 1212 may incorporate biometric information into a confidence level for determining an identity of a user. Biometric information output by the biometric component 1212 can be associated with specific user profile data such that the biometric information uniquely identifies a user profile of a user.

The radio frequency (RF) component 1214 may use RF localization to track devices that a user may carry or wear. For example, a user (and a user profile associated with the user) may be associated with a device. The device may emit RF signals (e.g., Wi-Fi, Bluetooth®, etc.). A device may detect the signal and indicate to the RF component 1214 the strength of the signal (e.g., as a received signal strength indication (RSSI)). The RF component 1214 may use the RSSI to determine an identity of a user (with an associated confidence level). In some instances, the RF component 1214 may determine that a received RF signal is associated with a mobile device that is associated with a particular user identifier.

In some instances, a personal device (such as a phone, tablet, wearable or other device) may include some RF or other detection processing capabilities so that a user who speaks an input may scan, tap, or otherwise acknowledge his/her personal device to the user device 110. In this manner, the user may "register" with the system 100 for purposes of the system 100 determining who spoke a particular input. Such a registration may occur prior to, during, or after speaking of an input.

The ML component 1216 may track the behavior of various users as a factor in determining a confidence level of the identity of the user. By way of example, a user may adhere to a regular schedule such that the user is at a first location during the day (e.g., at work or at school). In this example, the ML component 1216 would factor in past behavior and/or trends in determining the identity of the user that provided input to the user device 110 and/or the supporting device(s) 120. Thus, the ML component 1216 may use historical data and/or usage patterns over time to increase or decrease a confidence level of an identity of a user.

In at least some instances, the recognition confidence component 1218 receives determinations from the various components 1208, 1210, 1212, 1214, and 1216, and may determine a final confidence level associated with the identity of a user. In some instances, the confidence level may determine whether an action is performed in response to a user input. For example, if a user input includes a request to unlock a door, a confidence level may need to be above a threshold that may be higher than a threshold confidence level needed to perform a user request associated with playing a playlist or sending a message. The confidence level or other score data may be included in the user recognition data 1295.

The audio component 1210 may receive data from one or more sensors capable of providing an audio signal (e.g., one or more microphones) to facilitate recognition of a user. The audio component 1210 may perform audio recognition on an audio signal to determine an identity of the user and associated user identifier. In some instances, aspects of user device 110 and/or the supporting device(s) 120 may be configured at a computing device (e.g., a local server). Thus, in some instances, the audio component 1210 operating on a computing device may analyze all sound to facilitate recognition of a user. In some instances, the audio component 1210 may perform voice recognition to determine an identity of a user.

The audio component 1210 may also perform user identification based on audio data 911 input into the user device 110 and/or the supporting device(s) 120 for speech processing. The audio component 1210 may determine scores indicating whether speech in the audio data 911 originated from particular users. For example, a first score may indicate a likelihood that speech in the audio data 911 originated from a first user associated with a first user identifier, a second score may indicate a likelihood that speech in the audio data 911 originated from a second user associated with a second user identifier, etc. The audio component 1210 may perform user recognition by comparing speech characteristics represented in the audio data 911 to stored speech characteristics of users (e.g., stored voice profiles associated with the user device 110 that captured the spoken user input).

Figure 13:
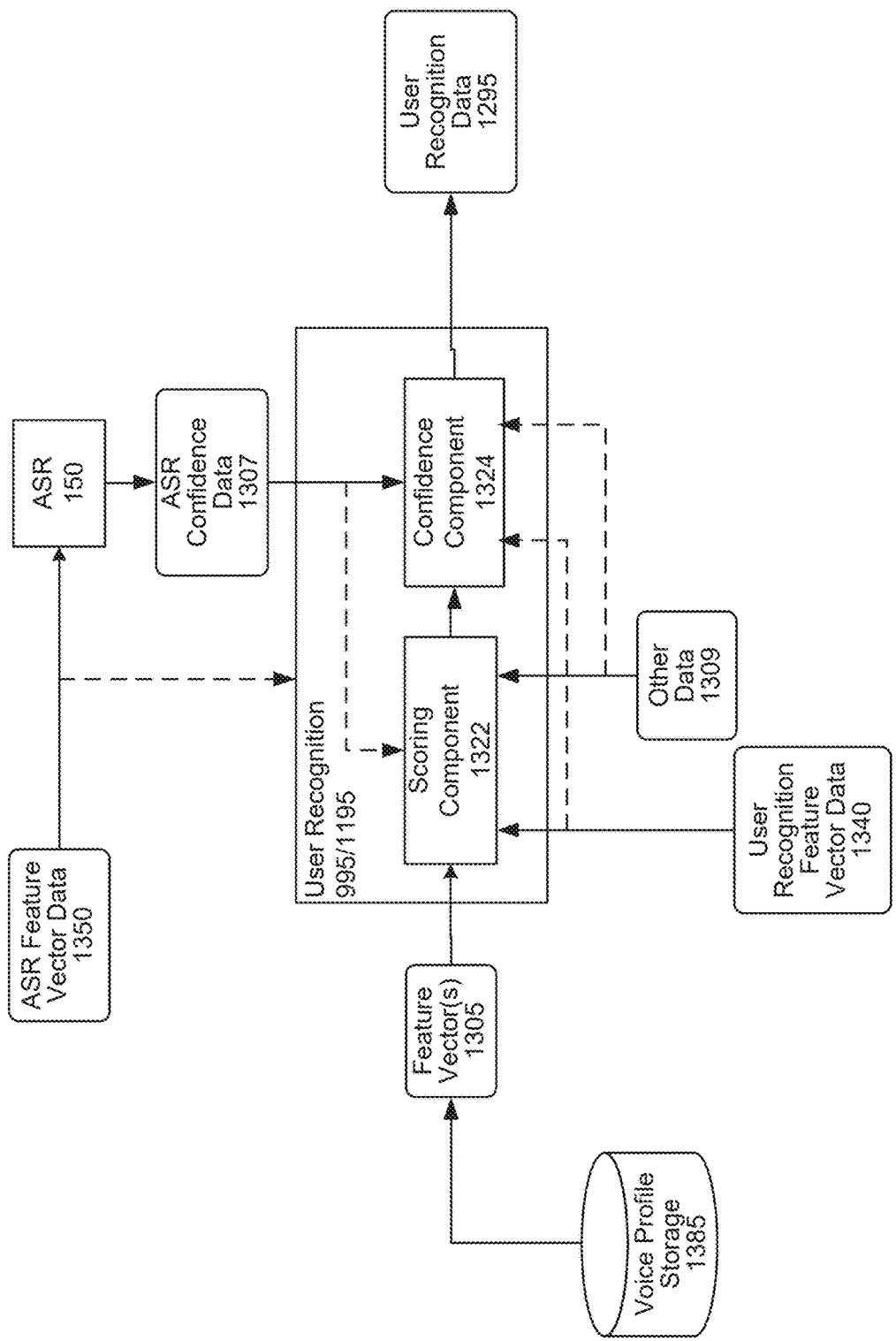
FIG. 13 is a system flow diagram illustrating example user recognition processing, according to embodiments of the present disclosure.

FIG. 13 illustrates user recognition processing as may be performed by the user recognition component 995. The ASR component 150 performs ASR processing on ASR feature vector data 1350. ASR confidence data 1307 may be passed to the user recognition component 995.

The user recognition component 995 performs user recognition using various data including the user recognition feature vector data 1340, feature vectors 1305 representing voice profiles of users of the system 100, the ASR confidence data 1307, and other data 1309. The user recognition component 995 may output the user recognition data 1295, which reflects a certain confidence that the user input was spoken by one or more particular users. The user recognition data 1295 may include one or more user identifiers (e.g., corresponding to one or more voice profiles). Each user identifier in the user recognition data 1295 may be associated with a respective confidence value, representing a likelihood that the user input corresponds to the user identifier. A confidence value may be a numeric or binned value.

The feature vector(s) 1305 input to the user recognition component 995 may correspond to one or more voice profiles. The user recognition component 995 may use the feature vector(s) 1305 to compare against the user recognition feature vector 1340, representing the present user input, to determine whether the user recognition feature vector 1340 corresponds to one or more of the feature vectors 1305 of the voice profiles. Each feature vector 1305 may be the same size as the user recognition feature vector 1340.

To perform user recognition, the user recognition component 995 may determine the user device 110 from which the audio data 911 originated. For example, the audio data 911 may be associated with metadata including a device identifier representing the user device 110. Either the user device 110 or the supporting device(s) 120 may generate the metadata. The system 100 may determine a group profile identifier associated with the device identifier, may determine user identifiers associated with the group profile identifier, and may include the group profile identifier and/or the user identifiers in the metadata. The system 100 may associate the metadata with the user recognition feature vector 1340 produced from the audio data 911. The user recognition component 995 may send a signal to voice profile storage 1385, with the signal requesting only audio data and/or feature vectors 1305 (depending on whether audio data and/or corresponding feature vectors are stored) associated with the device identifier, the group profile identifier, and/or the user identifiers represented in the metadata. This limits the universe of possible feature vectors 1305 the user recognition component 995 considers at runtime and thus decreases the amount of time to perform user recognition processing by decreasing the amount of feature vectors 1305 needed to be processed. Alternatively, the user recognition component 995 may access all (or some other subset of) the audio data and/or feature vectors 1305 available to the user recognition component 995. However, accessing all audio data and/or feature vectors 1305 will likely increase the amount of time needed to perform user recognition processing based on the magnitude of audio data and/or feature vectors 1305 to be processed.

If the user recognition component 995 receives audio data from the voice profile storage 1385, the user recognition component 995 may generate one or more feature vectors 1305 corresponding to the received audio data.

The user recognition component 995 may attempt to identify the user that spoke the speech represented in the audio data 911 by comparing the user recognition feature vector 1340 to the feature vector(s) 1305. The user recognition component 995 may include a scoring component 1322 that determines respective scores indicating whether the user input (represented by the user recognition feature vector 1340) was spoken by one or more particular users (represented by the feature vector(s) 1305). The user recognition component 995 may also include a confidence component 1324 that determines an overall accuracy of user recognition processing (such as those of the scoring component 1322) and/or an individual confidence value with respect to each user potentially identified by the scoring component 1322. The output from the scoring component 1322 may include a different confidence value for each received feature vector 1305. For example, the output may include a first confidence value for a first feature vector 1305*a* (representing a first voice profile), a second confidence value for a second feature vector 1305*b* (representing a second voice profile), etc. Although illustrated as two separate components, the scoring component 1322 and the confidence component 1324 may be combined into a single component or may be separated into more than two components.

The scoring component 1322 and the confidence component 1324 may implement one or more trained machine learning models (such as neural networks, classifiers, etc.) as known in the art. For example, the scoring component 1322 may use probabilistic linear discriminant analysis (PLDA) techniques. PLDA scoring determines how likely it is that the user recognition feature vector 1340 corresponds to a particular feature vector 1305. The PLDA scoring may generate a confidence value for each feature vector 1305 considered and may output a list of confidence values associated with respective user identifiers. The scoring component 1322 may also use other techniques, such as GMMs, generative Bayesian models, or the like, to determine confidence values.

The confidence component 1324 may input various data including information about the ASR confidence 1307, speech length (e.g., number of frames or other measured length of the user input), audio condition/quality data (such as signal-to-interference data or other metric data), fingerprint data, image data, or other factors to consider how confident the user recognition component 995 is with regard to the confidence values linking users to the user input. The confidence component 1324 may also consider the confidence values and associated identifiers output by the scoring component 1322. For example, the confidence component 1324 may determine that a lower ASR confidence 1307, or poor audio quality, or other factors, may result in a lower confidence of the user recognition component 995. Whereas a higher ASR confidence 1307, or better audio quality, or other factors, may result in a higher confidence of the user recognition component 995. Precise determination of the confidence may depend on configuration and training of the confidence component 1324 and the model(s) implemented thereby. The confidence component 1324 may operate using a number of different machine learning models/techniques such as GMM, neural networks, etc. For example, the confidence component 1324 may be a classifier configured to map a score output by the scoring component 1322 to a confidence value.

The user recognition component 995 may output user recognition data 1295 specific to a one or more user identifiers. For example, the user recognition component 995 may output user recognition data 1295 with respect to each received feature vector 1305. The user recognition data 1295 may include numeric confidence values (e.g., 0.0-1.0, 0-1000, or whatever scale the system is configured to operate). Thus, the user recognition data 1295 may output an n-best list of potential users with numeric confidence values (e.g., user identifier 123-0.2, user identifier 234-0.8). Alternatively or in addition, the user recognition data 1295 may include binned confidence values. For example, a computed recognition score of a first range (e.g., 0.0-0.33) may be output as "low," a computed recognition score of a second range (e.g., 0.34-0.66) may be output as "medium," and a computed recognition score of a third range (e.g., 0.67-1.0) may be output as "high." The user recognition component 995 may output an n-best list of user identifiers with binned confidence values (e.g., user identifier 123—low, user identifier 234—high). Combined binned and numeric confidence value outputs are also possible. Rather than a list of identifiers and their respective confidence values, the user recognition data 1295 may only include information related to the top scoring identifier as determined by the user recognition component 995. The user recognition component 995 may also output an overall confidence value that the individual confidence values are correct, where the overall confidence value indicates how confident the user recognition component 995 is in the output results. The confidence component 1324 may determine the overall confidence value.

The confidence component 1324 may determine differences between individual confidence values when determining the user recognition data 1295. For example, if a difference between a first confidence value and a second confidence value is large, and the first confidence value is above a threshold confidence value, then the user recognition component 995 is able to recognize a first user (associated with the feature vector 1305 associated with the first confidence value) as the user that spoke the user input with a higher confidence than if the difference between the confidence values were smaller.

The user recognition component 995 may perform thresholding to avoid incorrect user recognition data 1295 being output. For example, the user recognition component 995 may compare a confidence value output by the confidence component 1324 to a threshold confidence value. If the confidence value does not satisfy (e.g., does not meet or exceed) the threshold confidence value, the user recognition component 995 may not output user recognition data 1295, or may only include in that data 1295 an indicator that a user that spoke the user input could not be recognized. Further, the user recognition component 995 may not output user recognition data 1295 until enough user recognition feature vector data 1340 is accumulated and processed to verify a user above a threshold confidence value. Thus, the user recognition component 995 may wait until a sufficient threshold quantity of audio data of the user input has been processed before outputting user recognition data 1295. The quantity of received audio data may also be considered by the confidence component 1324.

The user recognition component 995 may be defaulted to output binned (e.g., low, medium, high) user recognition confidence values. However, such may be problematic in certain situations. For example, if the user recognition component 995 computes a single binned confidence value for multiple feature vectors 1305, the system may not be able to determine which particular user originated the user input. In this situation, the user recognition component 995 may override its default setting and output numeric confidence values. This enables the system to determine a user, associated with the highest numeric confidence value, originated the user input.

The user recognition component 995 may use other data 1309 to inform user recognition processing. A trained model(s) or other component of the user recognition component 995 may be trained to take other data 1309 as an input feature when performing user recognition processing. Other data 1309 may include a variety of data types depending on system configuration and may be made available from other sensors, devices, or storage. The other data 1309 may include a time of day at which the audio data 911 was generated by the user device 110 or received from the user device 110, a day of a week in which the audio data audio data 911 was generated by the user device 110 or received from the user device 110, etc.

The other data 1309 may include image data or video data. For example, facial recognition may be performed on image data or video data received from the user device 110 from which the audio data 911 was received (or another device). Facial recognition may be performed by the user recognition component 995. The output of facial recognition processing may be used by the user recognition component 995. That is, facial recognition output data may be used in conjunction with the comparison of the user recognition feature vector 1340 and one or more feature vectors 1305 to perform more accurate user recognition processing.

The other data 1309 may include location data of the user device 110. The location data may be specific to a building within which the user device 110 is located. For example, if the user device 110 is located in user A's bedroom, such location may increase a user recognition confidence value associated with user A and/or decrease a user recognition confidence value associated with user B.

The other data 1309 may include data indicating a type of the user device 110. Different types of devices may include, for example, a smart watch, a smart phone, a tablet, and a vehicle. The type of the user device 110 may be indicated in a profile associated with the user device 110. For example, if the user device 110 from which the audio data 911 was received is a smart watch or vehicle belonging to a user A, the fact that the user device 110 belongs to user A may increase a user recognition confidence value associated with user A and/or decrease a user recognition confidence value associated with user B.

The other data 1309 may include geographic coordinate data associated with the user device 110. For example, a group profile associated with a vehicle may indicate multiple users (e.g., user A and user B). The vehicle may include a global positioning system (GPS) indicating latitude and longitude coordinates of the vehicle when the vehicle generated the audio data 911. As such, if the vehicle is located at a coordinate corresponding to a work location/building of user A, such may increase a user recognition confidence value associated with user A and/or decrease user recognition confidence values of all other users indicated in a group profile associated with the vehicle. A profile associated with the user device 110 may indicate global coordinates and associated locations (e.g., work, home, etc.). One or more user profiles may also or alternatively indicate the global coordinates.

The other data 1309 may include data representing activity of a particular user that may be useful in performing user recognition processing. For example, a user may have recently entered a code to disable a home security alarm. A user device 110, represented in a group profile associated with the home, may have generated the audio data 911. The other data 1309 may reflect signals from the home security alarm about the disabling user, time of disabling, etc. If a mobile device (such as a smart phone, Tile, dongle, or other device) known to be associated with a particular user is detected proximate to (for example physically close to, connected to the same Wi-Fi network as, or otherwise nearby) the user device 110, this may be reflected in the other data 1309 and considered by the user recognition component 995.

Depending on system configuration, the other data 1309 may be configured to be included in the user recognition feature vector data 1340 so that all the data relating to the user input to be processed by the scoring component 1322 may be included in a single feature vector. Alternatively, the other data 1309 may be reflected in one or more different data structures to be processed by the scoring component 1322.

Figure 14:
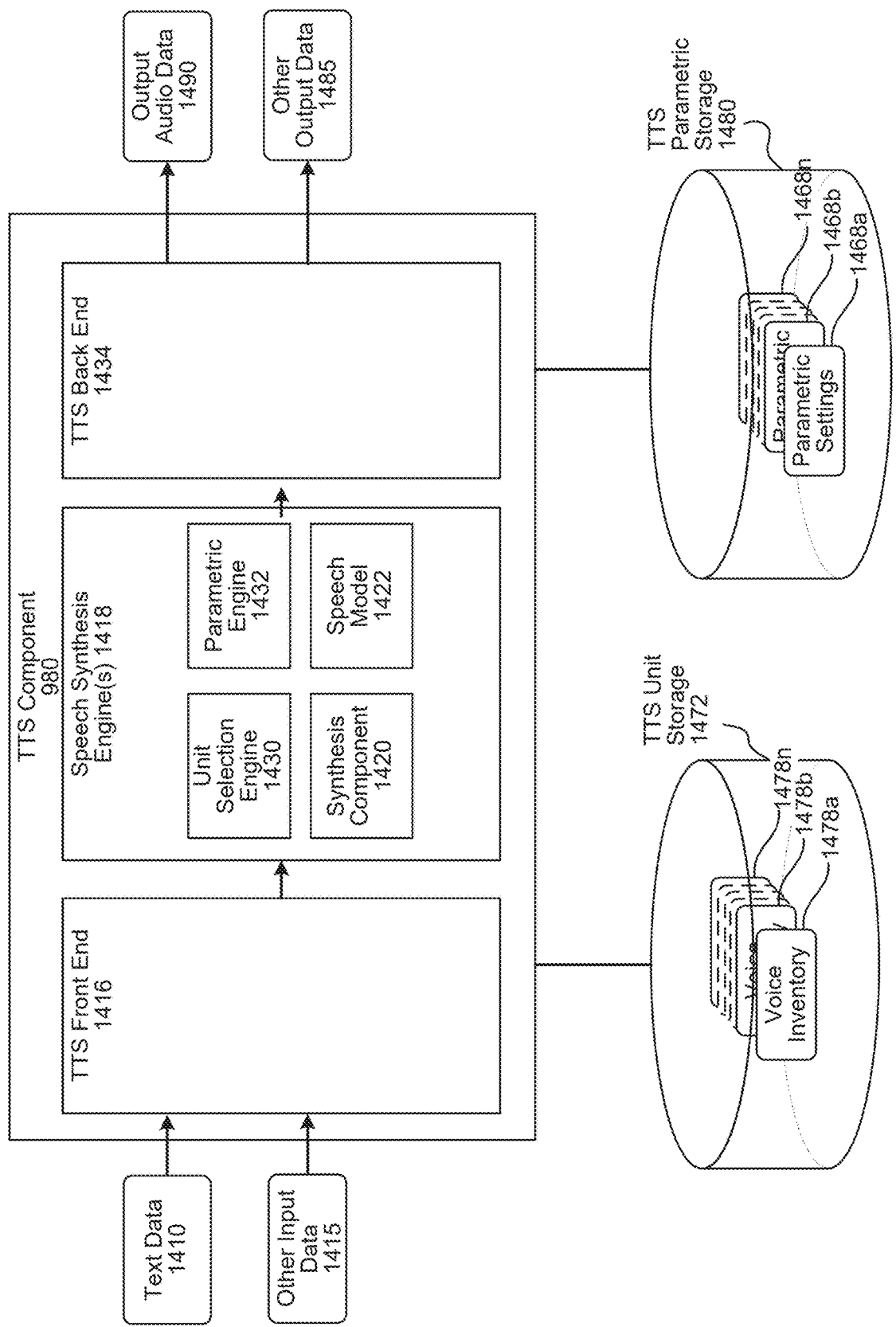
FIG. 14 is a conceptual diagram of example text-to-speech (TTS) processing, according to embodiments of the present disclosure.

Components of a system that may be used to perform unit selection, parametric TTS processing, and/or model-based audio synthesis are shown in FIG. 14. As shown in FIG. 14, the TTS component/processor 980 may include a TTS front end 1416, a speech synthesis engine 1418, TTS unit storage 1472, TTS parametric storage 1480, and a TTS back end 1434. The TTS unit storage 1472 may include, among other things, voice inventories 1478a-1478n that may include pre-recorded audio segments (called units) to be used by the unit selection engine 1430 when performing unit selection synthesis as described below. The TTS parametric storage 1480 may include, among other things, parametric settings 1468a-1468n that may be used by the parametric synthesis engine 1432 when performing parametric synthesis as described below. A particular set of parametric settings 1468 may correspond to a particular voice profile (e.g., whispered speech, excited speech, etc.).

In various embodiments of the present disclosure, model-based synthesis of audio data may be performed using by a speech model 1422 and a TTS front end 1416. The TTS front end 1416 may be the same as front ends used in traditional unit selection or parametric systems. In other embodiments, some or all of the components of the TTS front end 1416 are based on other trained models. The present disclosure is not, however, limited to any particular type of TTS front end 1416. The speech model 1422 may be used to synthesize speech without requiring the TTS unit storage 1472 or the TTS parametric storage 1480, as described in greater detail below.

TTS component receives text data 1410. Although the text data 1410 in FIG. 14 is input into the TTS component 980, it may be output by other component(s) (such as a skill component 190, NLU component 160, NLG component 979 or other component) and may be intended for output by the system. Thus in certain instances text data 1410 may be referred to as "output text data." Further, the data 1410 may not necessarily be text, but may include other data (such as symbols, code, other data, etc.) that may reference text (such as an indicator of a word) that is to be synthesized. Thus data 1410 may come in a variety of forms. The TTS front end 1416 transforms the data 1410 (from, for example, an application, user, device, or other data source) into a symbolic linguistic representation, which may include linguistic context features such as phoneme data, punctuation data, syllable-level features, word-level features, and/or emotion, speaker, accent, or other features for processing by the speech synthesis engine 1418. The syllable-level features may include syllable emphasis, syllable speech rate, syllable inflection, or other such syllable-level features; the word-level features may include word emphasis, word speech rate, word inflection, or other such word-level features. The emotion features may include data corresponding to an emotion associated with the text data 1410, such as surprise, anger, or fear. The speaker features may include data corresponding to a type of speaker, such as sex, age, or profession. The accent features may include data corresponding to an accent associated with the speaker, such as Southern, Boston, English, French, or other such accent.

The TTS front end 1416 may also process other input data 1415, such as text tags or text metadata, that may indicate, for example, how specific words should be pronounced, for example by indicating the desired output speech quality in tags formatted according to the speech synthesis markup language (SSML) or in some other form. For example, a first text tag may be included with text marking the beginning of when text should be whispered (e.g., <begin whisper>) and a second tag may be included with text marking the end of when text should be whispered (e.g., <end whisper>). The tags may be included in the text data 1410 and/or the text for a TTS request may be accompanied by separate metadata indicating what text should be whispered (or have some other indicated audio characteristic). The speech synthesis engine 1418 may compare the annotated phonetic units models and information stored in the TTS unit storage 1472 and/or TTS parametric storage 1480 for converting the input text into speech. The TTS front end 1416 and speech synthesis engine 1418 may include their own controller(s)/processor(s) and memory or they may use the controller/processor and memory of the supporting device(s) 120, user device 110, or other device, for example. Similarly, the instructions for operating the TTS front end 1416 and speech synthesis engine 1418 may be located within the TTS component 980, within the memory and/or storage of the supporting device(s) 120, user device 110, or within an external device.

Text data 1410 input into the TTS component 980 may be sent to the TTS front end 1416 for processing. The front end 1416 may include components for performing text normalization, linguistic analysis, linguistic prosody generation, or other such components. During text normalization, the TTS front end 1416 may first process the text input and generate standard text, converting such things as numbers, abbreviations (such as Apt., St., etc.), symbols ($, %, etc.) into the equivalent of written out words.

During linguistic analysis, the TTS front end 1416 may analyze the language in the normalized text to generate a sequence of phonetic units corresponding to the input text. This process may be referred to as grapheme-to-phoneme conversion. Phonetic units include symbolic representations of sound units to be eventually combined and output by the system as speech. Various sound units may be used for dividing text for purposes of speech synthesis. The TTS component 980 may process speech based on phonemes (individual sounds), half-phonemes, di-phones (the last half of one phoneme coupled with the first half of the adjacent phoneme), bi-phones (two consecutive phonemes), syllables, words, phrases, sentences, or other units. Each word may be mapped to one or more phonetic units. Such mapping may be performed using a language dictionary stored by the system, for example in the TTS unit storage 1472. The linguistic analysis performed by the TTS front end 1416 may also identify different grammatical components such as prefixes, suffixes, phrases, punctuation, syntactic boundaries, or the like. Such grammatical components may be used by the TTS component 980 to craft a natural-sounding audio waveform output. The language dictionary may also include letter-to-sound rules and other tools that may be used to pronounce pastly unidentified words or letter combinations that may be encountered by the TTS component 980. Generally, the more information included in the language dictionary, the higher quality the speech output.

Based on the linguistic analysis the TTS front end 1416 may then perform linguistic prosody generation where the phonetic units are annotated with desired prosodic characteristics, also called acoustic features, which indicate how the desired phonetic units are to be pronounced in the eventual output speech. During this stage the TTS front end 1416 may consider and incorporate any prosodic annotations that accompanied the text input to the TTS component 980. Such acoustic features may include syllable-level features, word-level features, emotion, speaker, accent, language, pitch, energy, duration, and the like. Application of acoustic features may be based on prosodic models available to the TTS component 980. Such prosodic models indicate how specific phonetic units are to be pronounced in certain circumstances. A prosodic model may consider, for example, a phoneme's position in a syllable, a syllable's position in a word, a word's position in a sentence or phrase, neighboring phonetic units, etc. As with the language dictionary, a prosodic model with more information may result in higher quality speech output than prosodic models with less information. Further, a prosodic model and/or phonetic units may be used to indicate particular speech qualities of the speech to be synthesized, where those speech qualities may match the speech qualities of input speech (for example, the phonetic units may indicate prosodic characteristics to make the ultimately synthesized speech sound like a whisper based on the input speech being whispered).

The output of the TTS front end 1416, which may be referred to as a symbolic linguistic representation, may include a sequence of phonetic units annotated with prosodic characteristics. This symbolic linguistic representation may be sent to the speech synthesis engine 1418, which may also be known as a synthesizer, for conversion into an audio waveform of speech for output to an audio output device and eventually to a user. The speech synthesis engine 1418 may be configured to convert the input text into high-quality natural-sounding speech in an efficient manner. Such high-quality speech may be configured to sound as much like a human speaker as possible, or may be configured to be understandable to a listener without attempts to mimic a precise human voice.

The speech synthesis engine 1418 may perform speech synthesis using one or more different methods. In one method of synthesis called unit selection, described further below, a unit selection engine 1430 matches the symbolic linguistic representation created by the TTS front end 1416 against a database of recorded speech, such as a database (e.g., TTS unit storage 1472) storing information regarding one or more voice corpuses (e.g., voice inventories 1478a-n). Each voice inventory may correspond to various segments of audio that was recorded by a speaking human, such as a voice actor, where the segments are stored in an individual inventory 1478 as acoustic units (e.g., phonemes, diphones, etc.). Each stored unit of audio may also be associated with an index listing various acoustic properties or other descriptive information about the unit. Each unit includes an audio waveform corresponding with a phonetic unit, such as a short wav file of the specific sound, along with a description of various features associated with the audio waveform. For example, an index entry for a particular unit may include information such as a particular unit's pitch, energy, duration, harmonics, center frequency, where the phonetic unit appears in a word, sentence, or phrase, the neighboring phonetic units, or the like. The unit selection engine 1430 may then use the information about each unit to select units to be joined together to form the speech output.

The unit selection engine 1430 matches the symbolic linguistic representation against information about the spoken audio units in the database. The unit database may include multiple examples of phonetic units to provide the system with many different options for concatenating units into speech. Matching units which are determined to have the desired acoustic qualities to create the desired output audio are selected and concatenated together (for example by a synthesis component 1420) to form output audio data 1490 representing synthesized speech. Using all the information in the unit database, a unit selection engine 1430 may match units to the input text to select units that can form a natural sounding waveform. One benefit of unit selection is that, depending on the size of the database, a natural sounding speech output may be generated. As described above, the larger the unit database of the voice corpus, the more likely the system will be able to construct natural sounding speech.

In another method of synthesis-called parametric synthesis-parameters such as frequency, volume, noise, are varied by a parametric synthesis engine 1432, digital signal processor or other audio generation device to create an artificial speech waveform output. Parametric synthesis uses a computerized voice generator, sometimes called a vocoder. Parametric synthesis may use an acoustic model and various statistical techniques to match a symbolic linguistic representation with desired output speech parameters. Using parametric synthesis, a computing system (for example, a synthesis component 1420) can generate audio waveforms having the desired acoustic properties. Parametric synthesis may include the ability to be accurate at high processing speeds, as well as the ability to process speech without large databases associated with unit selection, but also may produce an output speech quality that may not match that of unit selection. Unit selection and parametric techniques may be performed individually or combined together and/or combined with other synthesis techniques to produce speech audio output.

The TTS component 980 may be configured to perform TTS processing in multiple languages. For each language, the TTS component 980 may include specially configured data, instructions and/or components to synthesize speech in the desired language(s). To improve performance, the TTS component 980 may revise/update the contents of the TTS unit storage 1472 based on feedback of the results of TTS processing, thus enabling the TTS component 980 to improve speech synthesis.

The TTS unit storage 1472 may be customized for an individual user based on his/her individualized desired speech output. In particular, the speech unit stored in a unit database may be taken from input audio data of the user speaking. For example, to create the customized speech output of the system, the system may be configured with multiple voice inventories 1478a-1478n, where each unit database is configured with a different "voice" to match desired speech qualities. Such voice inventories may also be linked to user accounts. The voice selected by the TTS component 980 may be used to synthesize the speech. For example, one voice corpus may be stored to be used to synthesize whispered speech (or speech approximating whispered speech), another may be stored to be used to synthesize excited speech (or speech approximating excited speech), and so on. To create the different voice corpuses a multitude of TTS training utterances may be spoken by an individual (such as a voice actor) and recorded by the system. The audio associated with the TTS training utterances may then be split into small audio segments and stored as part of a voice corpus. The individual speaking the TTS training utterances may speak in different voice qualities to create the customized voice corpuses, for example the individual may whisper the training utterances, say them in an excited voice, and so on. Thus the audio of each customized voice corpus may match the respective desired speech quality. The customized voice inventory 1478 may then be used during runtime to perform unit selection to synthesize speech having a speech quality corresponding to the input speech quality.

Additionally, parametric synthesis may be used to synthesize speech with the desired speech quality. For parametric synthesis, parametric features may be configured that match the desired speech quality. If simulated excited speech was desired, parametric features may indicate an increased speech rate and/or pitch for the resulting speech. Many other examples are possible. The desired parametric features for particular speech qualities may be stored in a "voice" profile (e.g., parametric settings 1468) and used for speech synthesis when the specific speech quality is desired. Customized voices may be created based on multiple desired speech qualities combined (for either unit selection or parametric synthesis). For example, one voice may be "shouted" while another voice may be "shouted and emphasized." Many such combinations are possible.

Unit selection speech synthesis may be performed as follows. Unit selection includes a two-step process. First a unit selection engine 1430 determines what speech units to use and then it combines them so that the particular combined units match the desired phonemes and acoustic features and create the desired speech output. Units may be selected based on a cost function which represents how well particular units fit the speech segments to be synthesized. The cost function may represent a combination of different costs representing different aspects of how well a particular speech unit may work for a particular speech segment. For example, a target cost indicates how well an individual given speech unit matches the features of a desired speech output (e.g., pitch, prosody, etc.). A join cost represents how well a particular speech unit matches an adjacent speech unit (e.g., a speech unit appearing directly before or directly after the particular speech unit) for purposes of concatenating the speech units together in the eventual synthesized speech. The overall cost function is a combination of target cost, join cost, and other costs that may be determined by the unit selection engine 1430. As part of unit selection, the unit selection engine 1430 chooses the speech unit with the lowest overall combined cost. For example, a speech unit with a very low target cost may not necessarily be selected if its join cost is high.

The system may be configured with one or more voice corpuses for unit selection. Each voice corpus may include a speech unit database. The speech unit database may be stored in TTS unit storage 1472 or in another storage component. For example, different unit selection databases may be stored in TTS unit storage 1472. Each speech unit database (e.g., voice inventory) includes recorded speech utterances with the utterances' corresponding text aligned to the utterances. A speech unit database may include many hours of recorded speech (in the form of audio waveforms, feature vectors, or other formats), which may occupy a significant amount of storage. The unit samples in the speech unit database may be classified in a variety of ways including by phonetic unit (phoneme, diphone, word, etc.), linguistic prosodic label, acoustic feature sequence, speaker identity, etc. The sample utterances may be used to create mathematical models corresponding to desired audio output for particular speech units. When matching a symbolic linguistic representation the speech synthesis engine 1418 may attempt to select a unit in the speech unit database that most closely matches the input text (including both phonetic units and prosodic annotations). Generally the larger the voice corpus/speech unit database the better the speech synthesis may be achieved by virtue of the greater number of unit samples that may be selected to form the precise desired speech output.

Vocoder-based parametric speech synthesis may be performed as follows. A TTS component 980 may include an acoustic model, or other models, which may convert a symbolic linguistic representation into a synthetic acoustic waveform of the text input based on audio signal manipulation. The acoustic model includes rules which may be used by the parametric synthesis engine 1432 to assign specific audio waveform parameters to input phonetic units and/or prosodic annotations. The rules may be used to calculate a score representing a likelihood that a particular audio output parameter(s) (such as frequency, volume, etc.) corresponds to the portion of the input symbolic linguistic representation from the TTS front end 1416.

The parametric synthesis engine 1432 may use a number of techniques to match speech to be synthesized with input phonetic units and/or prosodic annotations. One common technique is using Hidden Markov Models (HMMs). HMMs may be used to determine probabilities that audio output should match textual input. HMMs may be used to translate from parameters from the linguistic and acoustic space to the parameters to be used by a vocoder (the digital voice encoder) to artificially synthesize the desired speech. Using HMMs, a number of states are presented, in which the states together represent one or more potential acoustic parameters to be output to the vocoder and each state is associated with a model, such as a Gaussian mixture model. Transitions between states may also have an associated probability, representing a likelihood that a current state may be reached from a past state. Sounds to be output may be represented as paths between states of the HMM and multiple paths may represent multiple possible audio matches for the same input text. Each portion of text may be represented by multiple potential states corresponding to different known pronunciations of phonemes and their parts (such as the phoneme identity, stress, accent, position, etc.). An initial determination of a probability of a potential phoneme may be associated with one state. As new text is processed by the speech synthesis engine 1418, the state may change or stay the same, based on the processing of the new text. For example, the pronunciation of a pastly processed word might change based on later processed words. A Viterbi algorithm may be used to find the most likely sequence of states based on the processed text. The HMMs may generate speech in parameterized form including parameters such as fundamental frequency (f0), noise envelope, spectral envelope, etc. that are translated by a vocoder into audio segments. The output parameters may be configured for particular vocoders such as a STRAIGHT vocoder, TANDEM-STRAIGHT vocoder, WORLD vocoder, HNM (harmonic plus noise) based vocoders, CELP (code-excited linear prediction) vocoders, GlottHMM vocoders, HSM (harmonic/stochastic model) vocoders, or others.

In addition to calculating potential states for one audio waveform as a potential match to a phonetic unit, the parametric synthesis engine 1432 may also calculate potential states for other potential audio outputs (such as various ways of pronouncing a particular phoneme or diphone) as potential acoustic matches for the acoustic unit. In this manner multiple states and state transition probabilities may be calculated.

The probable states and probable state transitions calculated by the parametric synthesis engine 1432 may lead to a number of potential audio output sequences. Based on the acoustic model and other potential models, the potential audio output sequences may be scored according to a confidence level of the parametric synthesis engine 1432. The highest scoring audio output sequence, including a stream of parameters to be synthesized, may be chosen and digital signal processing may be performed by a vocoder or similar component to create an audio output including synthesized speech waveforms corresponding to the parameters of the highest scoring audio output sequence and, if the proper sequence was selected, also corresponding to the input text. The different parametric settings 1468, which may represent acoustic settings matching a particular parametric "voice", may be used by the synthesis component 1420 to ultimately create the output audio data 1490.

When performing unit selection, after a unit is selected by the unit selection engine 1430, the audio data corresponding to the unit may be passed to the synthesis component 1420. The synthesis component 1420 may then process the audio data of the unit to create modified audio data where the modified audio data reflects a desired audio quality. The synthesis component 1420 may store a variety of operations that can convert unit audio data into modified audio data where different operations may be performed based on the desired audio effect (e.g., whispering, shouting, etc.).

As an example, input text may be received along with metadata, such as SSML tags, indicating that a selected portion of the input text should be whispered when output by the TTS module 980. For each unit that corresponds to the selected portion, the synthesis component 1420 may process the audio data for that unit to create a modified unit audio data. The modified unit audio data may then be concatenated to form the output audio data 1490. The modified unit audio data may also be concatenated with non-modified audio data depending on when the desired whispered speech starts and/or ends. While the modified audio data may be sufficient to imbue the output audio data with the desired audio qualities, other factors may also impact the ultimate output of audio such as playback speed, background effects, or the like, that may be outside the control of the TTS module 980. In that case, other output data 1485 may be output along with the output audio data 1490 so that an ultimate playback device (e.g., user device 110) receives instructions for playback that can assist in creating the desired output audio. Thus, the other output data 1485 may include instructions or other data indicating playback device settings (such as volume, playback rate, etc.) or other data indicating how output audio data including synthesized speech should be output. For example, for whispered speech, the output audio data 1490 may include other output data 1485 that may include a prosody tag or other indicator that instructs the user device 110 to slow down the playback of the output audio data 1490, thus making the ultimate audio sound more like whispered speech, which is typically slower than normal speech. In another example, the other output data 1485 may include a volume tag that instructs the user device 110 to output the speech at a volume level less than a current volume setting of the user device 110, thus improving the quiet whisper effect.

Various machine learning techniques may be used to train and operate models to perform various steps described herein, such as user recognition, tone detection, image processing, dialog management, etc. Models may be trained and operated according to various machine learning techniques. Such techniques may include, for example, neural networks (such as deep neural networks and/or recurrent neural networks), inference engines, trained classifiers, etc. Examples of trained classifiers include Support Vector Machines (SVMs), neural networks, decision trees, AdaBoost (short for "Adaptive Boosting") combined with decision trees, and random forests. Focusing on SVM as an example, SVM is a supervised learning model with associated learning algorithms that analyze data and recognize patterns in the data, and which are commonly used for classification and regression analysis. Given a set of training examples, each marked as belonging to one of two categories, an SVM training algorithm builds a model that assigns new examples into one category or the other, making it a non-probabilistic binary linear classifier. More complex SVM models may be built with the training set identifying more than two categories, with the SVM determining which category is most similar to input data. An SVM model may be mapped so that the examples of the separate categories are divided by clear gaps. New examples are then mapped into that same space and predicted to belong to a category based on which side of the gaps they fall on. Classifiers may issue a "score" indicating which category the data most closely matches. The score may provide an indication of how closely the data matches the category.

In order to apply the machine learning techniques, the machine learning processes themselves need to be trained. Training a machine learning component such as, in this case, one of the first or second models, requires establishing a "ground truth" for the training examples. In machine learning, the term "ground truth" refers to the accuracy of a training set's classification for supervised learning techniques. Various techniques may be used to train the models including backpropagation, statistical learning, supervised learning, semi-supervised learning, stochastic learning, or other known techniques.

Figure 15:
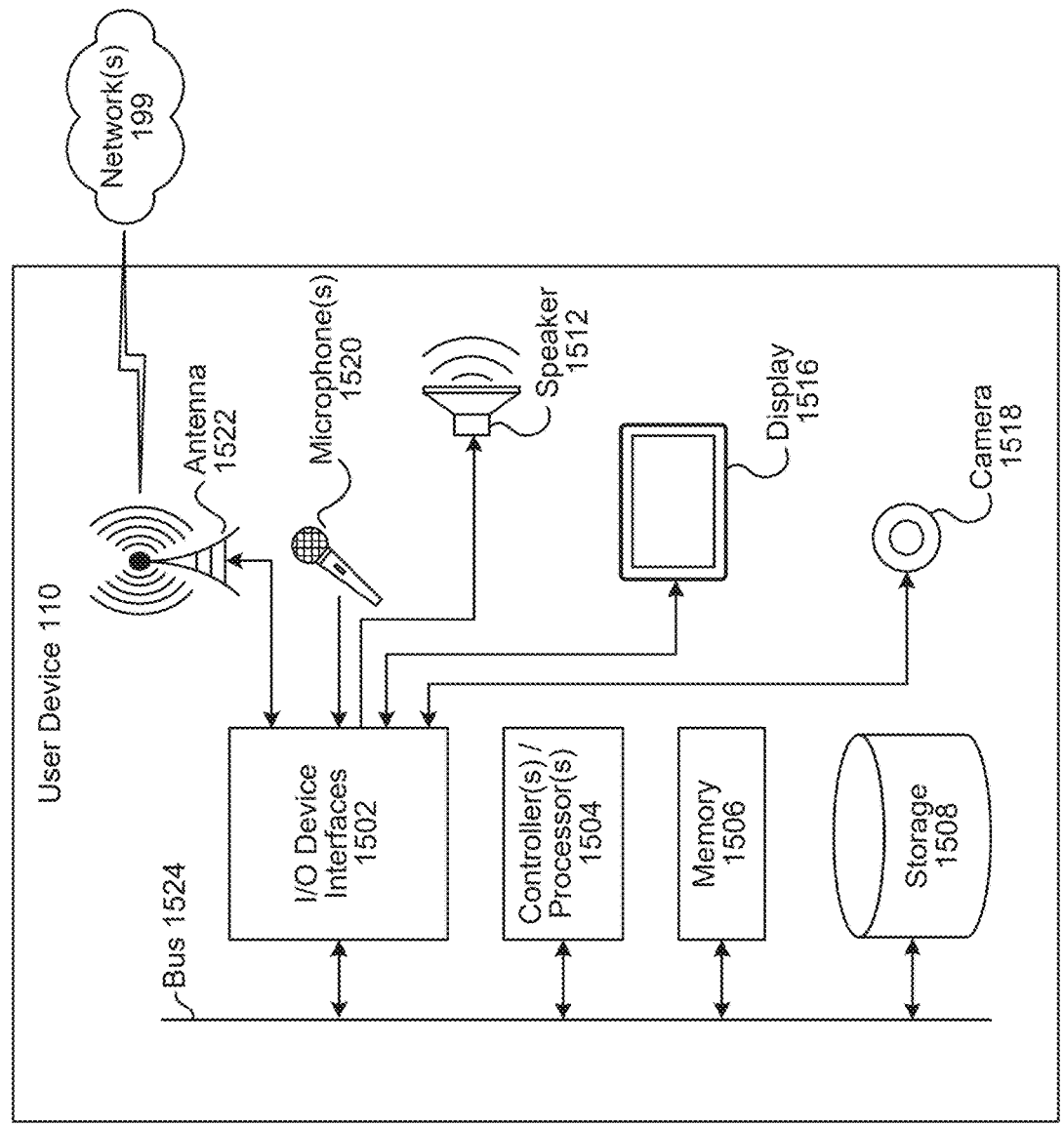
FIG. 15 is a block diagram conceptually illustrating example components of a user device, according to embodiments of the present disclosure.
Figure 16:
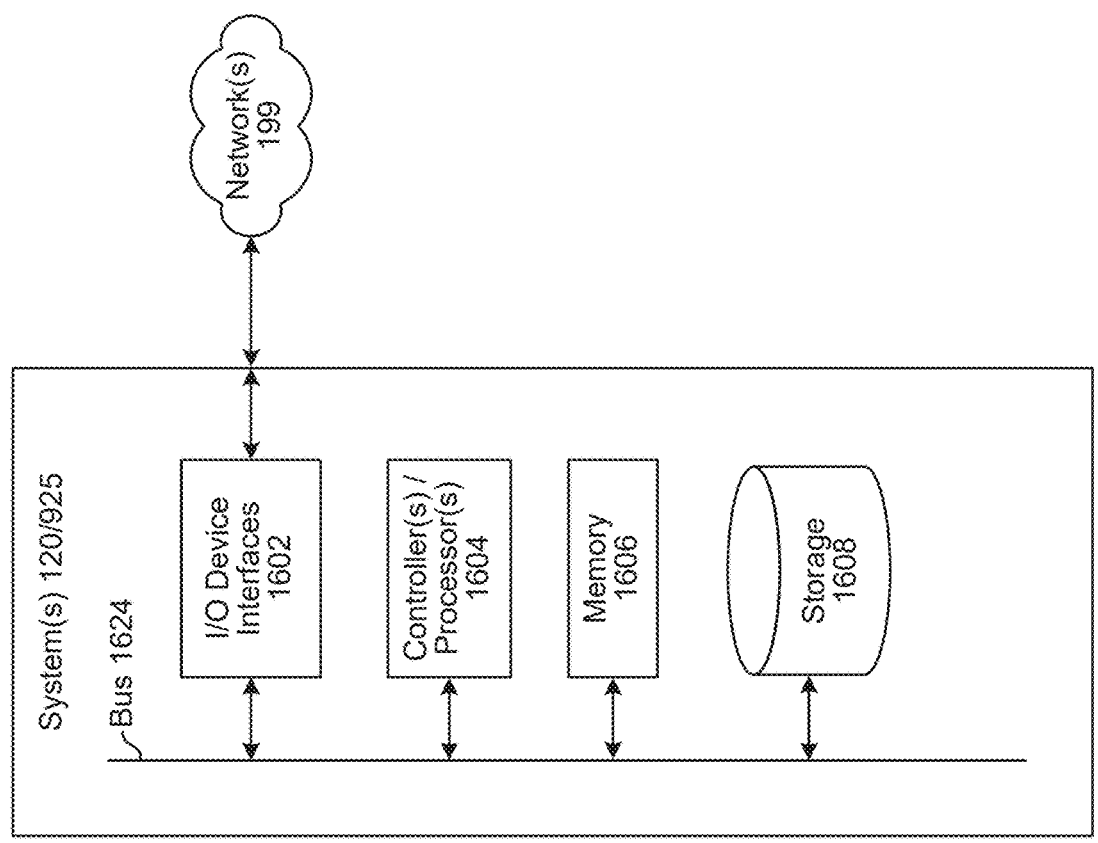
FIG. 16 is a block diagram conceptually illustrating example components of a supporting device/system, according to embodiments of the present disclosure.

FIG. 15 is a block diagram conceptually illustrating a user device 110 that may be used with the system. FIG. 16 is a block diagram conceptually illustrating example components of a remote device, such as the natural language command processing supporting device(s) 120, which may assist with ASR processing, NLU processing, etc., and a skill system 925. A system (120/925) may include one or more servers. A "server" as used herein may refer to a traditional server as understood in a server/client computing structure but may also refer to a number of different computing components that may assist with the operations discussed herein. For example, a server may include one or more physical computing components (such as a rack server) that are connected to other devices/components either physically and/or over a network and is capable of performing computing operations. A server may also include one or more virtual machines that emulates a computer system and is run on one or across multiple devices. A server may also include other combinations of hardware, software, firmware, or the like to perform operations discussed herein. The server(s) may be configured to operate using one or more of a client-server model, a computer bureau model, grid computing techniques, fog computing techniques, mainframe techniques, utility computing techniques, a peer-to-peer model, sandbox techniques, or other computing techniques.

While the user device 110 may operate locally to a user (e.g., within a same environment so the device may receive inputs and playback outputs for the user) he server/supporting device(s) 120 may be located remotely from the user device 110 as its operations may not require proximity to the user. The server/supporting device(s) 120 may be located in an entirely different location from the user device 110 (for example, as part of a cloud computing system or the like) or may be located in a same environment as the user device 110 but physically separated therefrom (for example a home server or similar device that resides in a user's home or business but perhaps in a closet, basement, attic, or the like). One benefit to the server/supporting device(s) 120 being in a user's home/business is that data used to process a command/return a response may be kept within the user's home, thus reducing potential privacy concerns.

Multiple systems (120/925) may be included in the system 100 of the present disclosure, such as one or more of the supporting device(s) 120, one or more skill systems 925, etc. In operation, each of these systems may include computer-readable and computer-executable instructions that reside on the respective device (120/925), as will be discussed further below.

Each of these devices (110/120/925) may include one or more controllers/processors (1504/1604), which may each include a central processing unit (CPU) for processing data and computer-readable instructions, and a memory (1506/1606) for storing data and instructions of the respective device. The memories (1506/1606) may individually include volatile random access memory (RAM), non-volatile read only memory (ROM), non-volatile magnetoresistive memory (MRAM), and/or other types of memory. Each device (110/120/925) may also include a data storage component (1508/1608) for storing data and controller/processor-executable instructions. Each data storage component (1508/1608) may individually include one or more non-volatile storage types such as magnetic storage, optical storage, solid-state storage, etc. Each device (110/120/925) may also be connected to removable or external non-volatile memory and/or storage (such as a removable memory card, memory key drive, networked storage, etc.) through respective input/output device interfaces (1502/1602).

Computer instructions for operating each device (110/120/925) and its various components may be executed by the respective device's controller(s)/processor(s) (1504/1604), using the memory (1506/1606) as temporary "working" storage at runtime. A device's computer instructions may be stored in a non-transitory manner in non-volatile memory (1506/1606), storage (1508/1608), or an external device(s). Alternatively, some or all of the executable instructions may be embedded in hardware or firmware on the respective device in addition to or instead of software.

Each device (110/120/925) includes input/output device interfaces (1502/1602). A variety of components may be connected through the input/output device interfaces (1502/1602), as will be discussed further below. Additionally, each device (110/120/925) may include an address/data bus (1524/1624) for conveying data among components of the respective device. Each component within a device (110/120/925) may also be directly connected to other components in addition to (or instead of) being connected to other components across the bus (1524/1624).

Referring to FIG. 15, the user device 110 may include input/output device interfaces 1502 that connect to a variety of components such as an audio output component such as a speaker 1512, a wired headset or a wireless headset (not illustrated), or other component capable of outputting audio. The user device 110 may also include an audio capture component. The audio capture component may be, for example, a microphone 1520 or array of microphones, a wired headset or a wireless headset (not illustrated), etc. If an array of microphones is included, approximate distance to a sound's point of origin may be determined by acoustic localization based on time and amplitude differences between sounds captured by different microphones of the array. The user device 110 may additionally include a display 1516 for displaying content. The user device 110 may further include a camera 1518.

Via antenna(s) 1522, the input/output device interfaces 1502 may connect to one or more networks 199 via a wireless local area network (WLAN) (such as Wi-Fi) radio, Bluetooth, and/or wireless network radio, such as a radio capable of communication with a wireless communication network such as a Long Term Evolution (LTE) network, WiMAX network, 3G network, 4G network, 5G network, etc. A wired connection such as Ethernet may also be supported. Through the network(s) 199, the system may be distributed across a networked environment. The I/O device interface (1502/1602) may also include communication components that allow data to be exchanged between devices such as different physical servers in a collection of servers or other components.

The components of the user device 110, the natural language command processing supporting device(s) 120, or a skill system 925 may include their own dedicated processors, memory, and/or storage. Alternatively, one or more of the components of the user device 110, the natural language command processing supporting device(s) 120, or a skill system 925 may utilize the I/O interfaces (1502/1602), processor(s) (1504/1604), memory (1506/1606), and/or storage (1508/1608) of the user device 110, natural language command processing supporting device(s) 120, or the skill system 925, respectively. Thus, the ASR component 150 may have its own I/O interface(s), processor(s), memory, and/or storage; the NLU component 160 may have its own I/O interface(s), processor(s), memory, and/or storage; and so forth for the various components discussed herein.

As noted above, multiple devices may be employed in a single system. In such a multi-device system, each of the devices may include different components for performing different aspects of the system's processing. The multiple devices may include overlapping components. The components of the user device 110, the natural language command processing supporting device(s) 120, and a skill system 925, as described herein, are illustrative, and may be located as a stand-alone device or may be included, in whole or in part, as a component of a larger device or system. As can be appreciated, a number of components may exist either on a supporting device(s) 120 and/or on user device 110. For example, language processing 992/1192 (which may include ASR 150/1150), language output 993/1193 (which may include NLG 979/1179 and TTS 980/1180), etc., for example as illustrated in FIGS. 9 and 11. Unless expressly noted otherwise, the system version of such components may operate similarly to the device version of such components and thus the description of one version (e.g., the system version or the local version) applies to the description of the other version (e.g., the local version or system version) and vice-versa.

Figure 17:
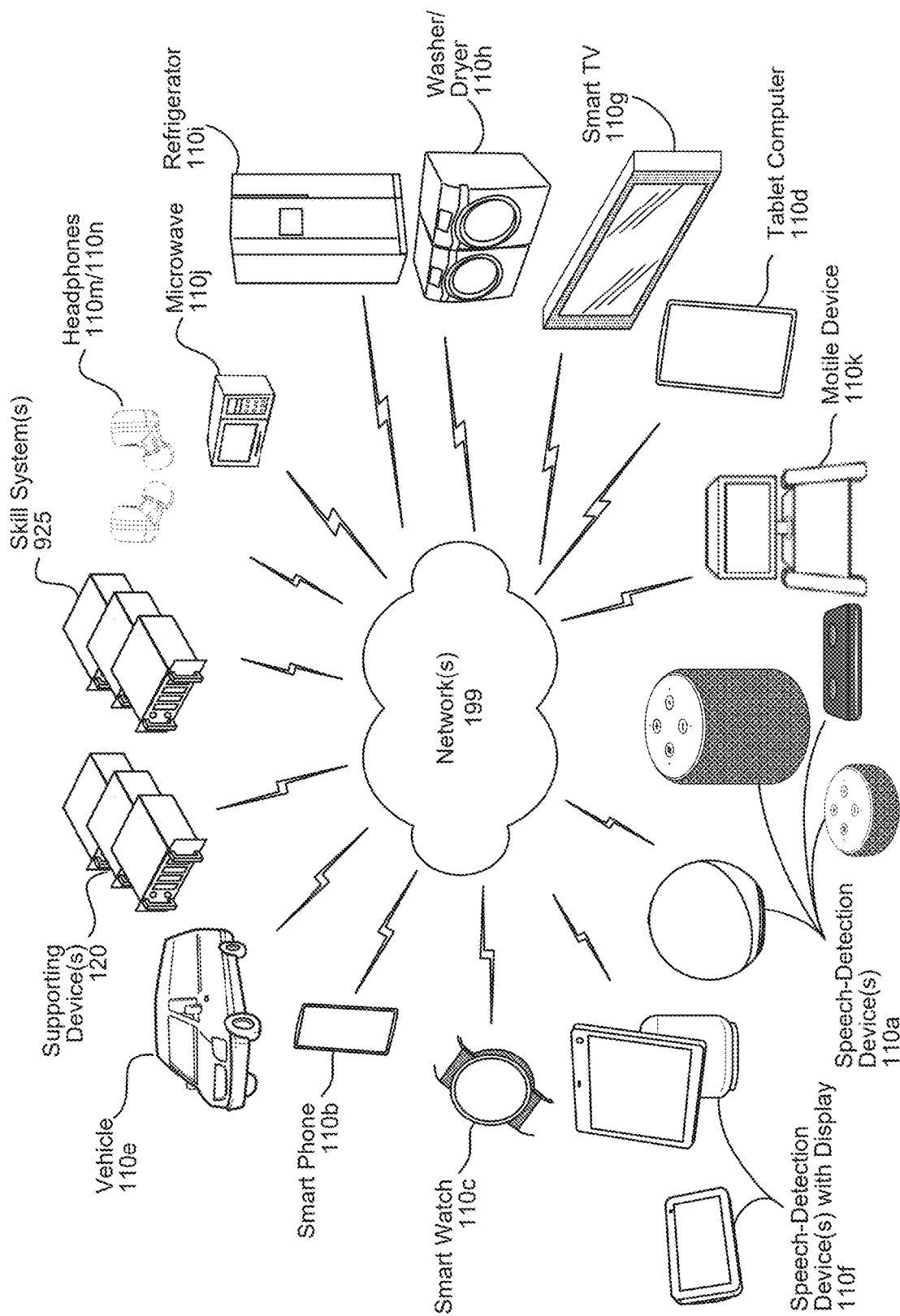
FIG. 17 illustrates an example of a computer network for use with the system, according to embodiments of the present disclosure.

As illustrated in FIG. 17, multiple devices (110a-110n, 120, 925) may contain components of the system and the devices may be connected over a network(s) 199. The network(s) 199 may include a local or private network or may include a wide network such as the Internet. Devices may be connected to the network(s) 199 through either wired or wireless connections. For example, a speech-detection user device 110a, a smart phone 110b, a smart watch 110c, a tablet computer 110d, a vehicle 110e, a speech-detection device with display 110f, a display/smart television 110g, a washer/dryer 110h, a refrigerator 110i, a microwave 110j, autonomously motile user device 110k (e.g., a robot), etc. (e.g., a device such as a FireTV stick, Echo Auto or the like) may be connected to the network(s) 199 through a wireless service provider, over a Wi-Fi or cellular network connection, or the like. Other devices are included as network-connected support devices, such as the natural language command processing supporting device(s) 120, the skill system(s) 925, and/or others. The support devices may connect to the network(s) 199 through a wired connection or wireless connection. Networked devices may capture audio using one-or-more built-in or connected microphones or other audio capture devices, with processing performed by ASR components, NLU components, or other components of the same device or another device connected via the network(s) 199, such as the ASR component 150, the NLU component 160, etc. of the natural language command processing supporting device(s) 120.

The concepts disclosed herein may be applied within a number of different devices and computer systems, including, for example, general-purpose computing systems, speech processing systems, and distributed computing environments.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers and speech processing should recognize that components and process steps described herein may be interchangeable with other components or steps, or combinations of components or steps, and still achieve the benefits and advantages of the present disclosure. Moreover, it should be apparent to one skilled in the art, that the disclosure may be practiced without some or all of the specific details and steps disclosed herein. Further, unless expressly stated to the contrary, features/operations/components, etc. from one embodiment discussed herein may be combined with features/operations/components, etc. from another embodiment discussed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage medium may be implemented by a volatile computer memory, non-volatile computer memory, hard drive, solid-state memory, flash drive, removable disk, and/or other media. In addition, components of system may be implemented as in firmware or hardware.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without other input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

As used in this disclosure, the term "a" or "one" may include one or more items unless specifically stated otherwise. Further, the phrase "based on" is intended to mean "based at least in part on" unless specifically stated otherwise.

What is claimed is:

1. A computer-implemented method comprising:
   receiving, from a device, first input audio data corresponding to a first spoken natural language user input, wherein the first input audio data is associated with user profile data;
   using the first input audio data, performing speech processing to determine the first spoken natural language user input is to be responded to using a speech-based conversational assessment component;
   generating first output data including a first question related to a speech-based conversational assessment;
   sending the first output data to the device for presentation;
   after sending the first output data, receiving, from the device, second input audio data corresponding to a second spoken natural language user input responsive to the first question;
   using the second input audio data, performing automatic speech recognition (ASR) processing to generate ASR results data corresponding to the second spoken natural language user input;
   processing the ASR results data to generate lexical embedding data corresponding to the second spoken natural language user input;

processing the second input audio data to determine tone data representing a tone of the second spoken natural language user input;

processing the ASR results data to determine first topic data representing a first topic of the second spoken natural language user input;

generating state data using the ASR results data, the lexical embedding data, the tone data, and the first topic data;

determining past state data associated with the user profile data, wherein the past state data corresponds to one or more speech-based conversational assessments;

processing the state data and the past state data using a first trained machine learning model to determine a first type of response to the second spoken natural language user input;

processing the state data and the past state data using a second trained machine learning model to determine a second type of response to the second spoken natural language user input;

based on at least one of the first type of response and the second type of response, generating second output data including a second question related to the speech-based conversational assessment; and sending the second output data to the device for presentation.

2. The computer-implemented method of claim 1, further comprising:

receiving a set of questions corresponding to a survey, wherein the set of questions comprise a third question corresponding to a second topic and a fourth question corresponding to a third topic; and generating the second question to correspond to the third question based on the first topic data corresponding to the first topic.

3. The computer-implemented method of claim 1, further comprising:

processing the state data to determine second topic data of the state data;

processing the past state data to determine third topic data of the past state data; and determining a difference between the second topic data and the third topic data, wherein, in response to determining the difference, the second question requests a confirmation of the lexical embedding data.

4. The computer-implemented method of claim 1, further comprising:

processing the state data and the past state data using the first trained machine learning model to determine the first type of response to correspond to an empathetic phrase;

processing the state data and the past state data using the second trained machine learning model to determine the second type of response to correspond to a question to confirm the ASR results data correctly represent the second spoken natural language user input; and processing the state data and the past state data using a third trained machine learning model to determine a third type of response configured to elicit further information.

5. A computer-implemented method comprising:

receiving input audio data representing a spoken natural language user input of a present session, the input audio data being associated with user profile data;

using the input audio data, performing automatic speech recognition (ASR) processing to generate ASR results data corresponding to the spoken natural language user input;

determining state data for the present session, wherein the state data includes the ASR results data and indicates at least one of:

a first topic of the spoken natural language user input; and a user state associated with the spoken natural language user input;

determining past state data associated with the user profile data, wherein the past state data corresponds to one or more past sessions;

processing the state data and the past state data using a first trained machine learning model to determine a first type of response to the spoken natural language user input;

processing the state data and the past state data using a second trained machine learning model to determine a second type of response to the spoken natural language user input;

generating first output data based on at least one of the first type of response and the second type of response; and sending the first output data to a device for presentation.

6. The computer-implemented method of claim 5, further comprising:

using the ASR results data, generating lexical embedding data representing the spoken natural language user input; and determining the state data to further include the lexical embedding data.

7. The computer-implemented method of claim 5, further comprising:

determining the state data to indicate a second topic of a past natural language user input of the present session;

processing the state data to determine a difference between the first topic and the second topic; and generating the first output data based at least in part on the difference.

8. The computer-implemented method of claim 5, further comprising:

processing the input audio data to determine a tone corresponding to the spoken natural language user input; and determining the state data to further indicate the tone.

9. The computer-implemented method of claim 5, further comprising:

processing the state data and the past state data using the first trained machine learning model to determine the first type of response to correspond to an empathetic phrase;

processing the state data and the past state data using the second trained machine learning model to determine the second type of response to correspond to a question to confirm the ASR results data correctly represent the spoken natural language user input; and processing the state data and the past state data using a third trained machine learning model to determine a third type of response configured to elicit further information.

10. The computer-implemented method of claim 5, further comprising:
   determining the user state satisfies a condition; and
   generating the first output data based on the user state satisfying the condition, wherein the first output data recommends an assistance provider being contacted.

11. The computer-implemented method of claim 5, further comprising:
   receiving a set of questions for obtaining information related to the present session; and
   based on the first topic of the spoken natural language user input, determining the first output data from among the set of questions.

12. The computer-implemented method of claim 5, further comprising:
   generating acoustic embedding data corresponding to the input audio data; and
   determining the state data to further include the acoustic embedding data.

13. A computing system comprising:
   at least one processor; and
   at least one memory comprising instructions that, when executed by the at least one processor, cause the computing system to:
      receive input audio data representing a spoken natural language user input of a present session, the input audio data being associated with user profile data;
      using the input audio data, perform automatic speech recognition (ASR) processing to generate ASR results data corresponding to the spoken natural language user input;
      determine state data for the present session, wherein the state data includes the ASR results data and indicates at least one of:
         a first topic of the spoken natural language user input; and
         a user state associated with the spoken natural language user input;
      determine past state data associated with the user profile data, wherein the past state data corresponds to one or more past sessions;
      process the state data and the past state data using a first trained machine learning model to determine a first type of response to the spoken natural language user input;
      process the state data and the past state data using a second trained machine learning model to determine a second type of response to the spoken natural language user input;
      generate first output data based on at least one of the first type of response and the second type of response; and
      send the first output data to a device for presentation.

14. The computing system of claim 13, wherein the at least one memory further comprises instructions that, when executed by the at least one processor, further cause the computing system to:
   using the ASR results data, generate lexical embedding data representing the spoken natural language user input; and
   determine the state data to further include the lexical embedding data.

15. The computing system of claim 13, wherein the at least one memory further comprises instructions that, when executed by the at least one processor, further cause the computing system to:
   determine the state data to indicate a second topic of a past natural language user input of the present session;
   process the state data to determine a difference between the first topic and the second topic; and
   generate the first output data based at least in part on the difference.

16. The computing system of claim 13, wherein the instructions that cause the computing system to generate the first output data further comprise instructions that, when executed by the at least one processor, further cause the computing system to:
   process the input audio data to determine a tone corresponding to the spoken natural language user input; and
   determine the state data to further indicate the tone.

17. The computing system of claim 13, wherein the at least one memory further comprises instructions that, when executed by the at least one processor, further cause the computing system to:
   process the state data and the past state data using the first trained machine learning model to determine the first type of response to correspond to an empathetic phrase;
   process the state data and the past state data using the second trained machine learning model to determine the second type of response to correspond to a question to confirm the ASR results data correctly represent the spoken natural language user input; and
   process the state data and the past state data using a third one trained machine learning model to determine a third type of response configured to elicit further information.

18. The computing system of claim 13, wherein the at least one memory further comprises instructions that, when executed by the at least one processor, further cause the computing system to:
   determine the user state satisfies a condition; and
   generate the first output data based on the user state satisfying the condition, wherein the first output data recommends an assistance provider being contacted.

19. The computing system of claim 13, wherein the at least one memory further comprises instructions that, when executed by the at least one processor, further cause the computing system to:
   receive a set of questions for obtaining information related to the present session; and
   based on the first topic of the spoken natural language user input, determine the first output data from among the set of questions.

20. The computing system of claim 13, wherein the at least one memory further comprises instructions that, when executed by the at least one processor, further cause the computing system to:
   generate acoustic embedding data corresponding to the input audio data; and
   determine the state data to further include the acoustic embedding data.

\* \* \* \* \*